(12) United States Patent
Trotta

(10) Patent No.: US 7,939,468 B2
(45) Date of Patent: *May 10, 2011

(54) METHODS OF IDENTIFYING COMPOUNDS THAT TARGET TRNA SPLICING ENDONUCLEASE AND USES OF SAID COMPOUNDS AS ANTI-PROLIFERATIVE AGENTS

(75) Inventor: Christopher R. Trotta, Somerset, NJ (US)

(73) Assignee: PTC Therapeutics, Inc., South Plainfield, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 12/756,786

(22) Filed: Apr. 8, 2010

(65) Prior Publication Data

US 2010/0267035 A1    Oct. 21, 2010

Related U.S. Application Data

(63) Continuation of application No. 10/551,301, filed as application No. PCT/US2004/009572 on Mar. 26, 2004, now abandoned.

(60) Provisional application No. 60/458,079, filed on Mar. 27, 2003.

(51) Int. Cl.
   *C12Q 1/68* (2006.01)
   *C40B 30/06* (2006.01)
   *C40B 40/08* (2006.01)
   *A61K 31/00* (2006.01)

(52) U.S. Cl. .............................................. 506/10; 435/6

(58) Field of Classification Search ........................ None
   See application file for complete search history.

(56) References Cited

U.S. PATENT DOCUMENTS

| | | |
|---|---|---|
| 4,987,071 A | 1/1991 | Cech et al. |
| 5,093,246 A | 3/1992 | Cech et al. |
| 5,310,664 A | 5/1994 | Butow et al. |
| 5,354,855 A | 10/1994 | Cech et al. |
| 5,439,797 A | 8/1995 | Tsien et al. |
| 5,591,610 A | 1/1997 | Cech et al. |
| 5,726,195 A | 3/1998 | Hill et al. |
| 5,776,738 A | 7/1998 | Dell'Orco, Sr. |
| 5,939,288 A | 8/1999 | Thornburg |
| 5,994,124 A | 11/1999 | Bozzoni |
| 6,025,167 A | 2/2000 | Cech et al. |
| 6,180,399 B1 | 1/2001 | Cech et al. |
| 6,214,563 B1 | 4/2001 | Negulescu et al. |
| 6,221,587 B1 | 4/2001 | Ecker et al. |

(Continued)

FOREIGN PATENT DOCUMENTS

CA    1340280    12/1998

(Continued)

OTHER PUBLICATIONS

U.S. Appl. No. 12/753,590, filed Apr. 2, 2010, Trotta.

(Continued)

*Primary Examiner* — Jeffrey S. Lundgren
*Assistant Examiner* — Christian Boesen
(74) *Attorney, Agent, or Firm* — Jones Day

(57) ABSTRACT

The present invention relates to a method for screening and identifying compounds that modulate the activity tRNA splicing endonuclease. In particular, the invention provides assays for the identification of compounds that inhibit animalia tRNA splicing endonuclease. The methods of the present invention provide a simple, sensitive assay for high-throughput screening of libraries of compounds to identify pharmaceutical leads useful for treating and/or preventing cancer.

12 Claims, 2 Drawing Sheets

U.S. PATENT DOCUMENTS

Figure 1:
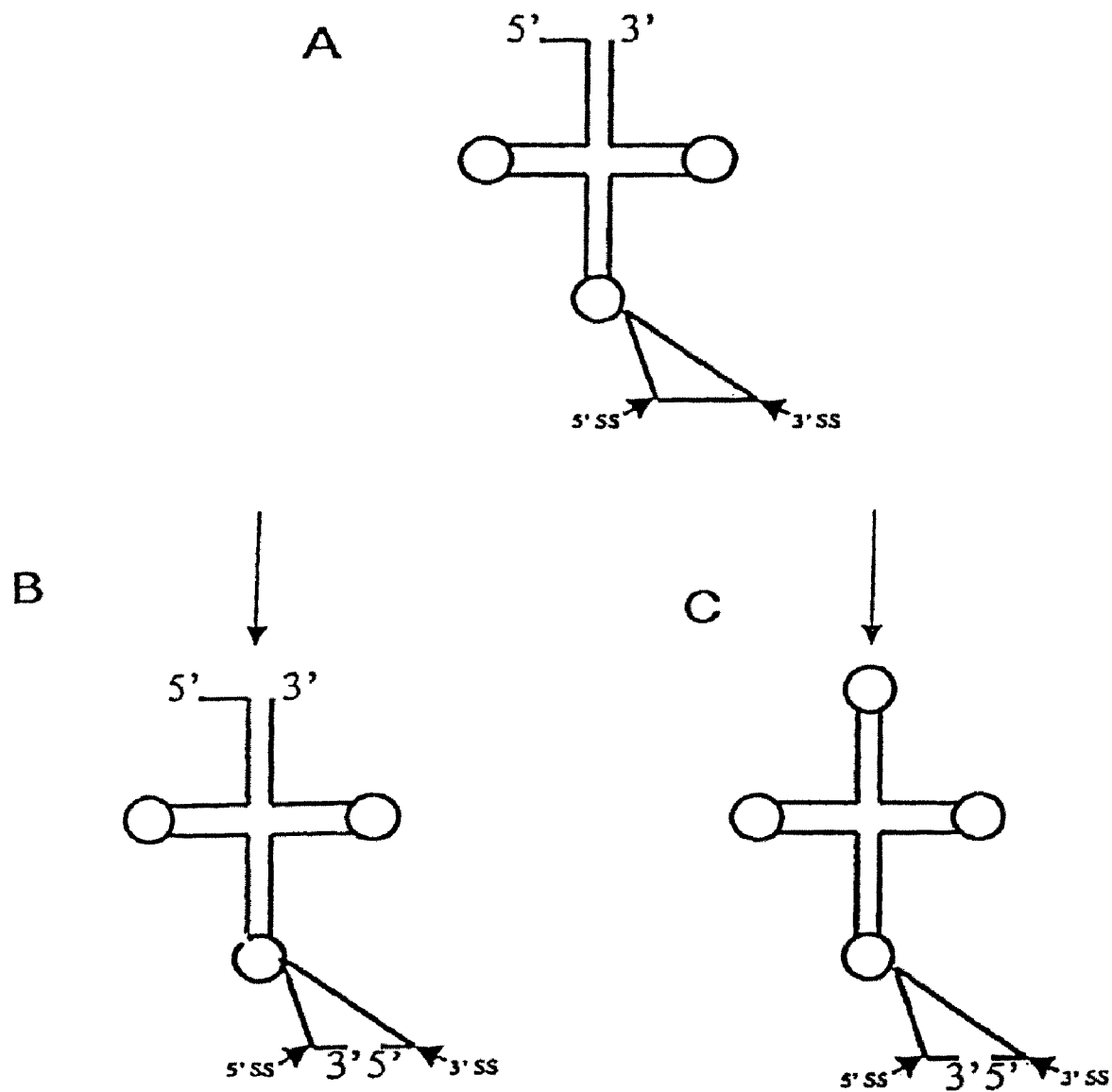

| | | | |
|---|---|---|---|
| 6,221,612 B1 | 4/2001 | Knapp et al. |
| 6,232,070 B1 | 5/2001 | Shuman |
| 6,446,032 B1 | 9/2002 | Schimmel |
| 6,503,713 B1 | 1/2003 | Rana et al. |
| 6,583,309 B1 | 6/2003 | Rana et al. |
| 6,875,736 B2 | 4/2005 | Rana et al. |
| 2004/0023239 A1 | 2/2004 | Tocchini-Valentini et al. |
| 2004/0219545 A1 | 11/2004 | Rando et al. |
| 2005/0053985 A1 | 3/2005 | Trotta et al. |
| 2005/0142545 A1 | 6/2005 | Conn et al. |
| 2005/0221368 A1 | 10/2005 | Rana et al. |
| 2006/0194234 A1 | 8/2006 | Conn et al. |
| 2006/0228730 A1 | 10/2006 | Rando et al. |
| 2006/0269923 A1 | 11/2006 | Trotta |
| 2007/0020630 A1 | 1/2007 | Trotta |
| 2007/0178456 A1 | 8/2007 | Trotta |
| 2010/0136710 A1 | 6/2010 | Trotta et al. |

FOREIGN PATENT DOCUMENTS

| | | |
|---|---|---|
| CN | 1328156 | 12/2001 |
| DE | 3436818 | 4/1989 |
| EP | 0177827 B1 | 11/1993 |
| WO | WO 91/09942 | 7/1991 |
| WO | WO 98/49274 | 11/1998 |
| WO | WO 99/20795 | 4/1999 |
| WO | WO 00/67580 | 11/2000 |
| WO | WO 01/12820 | 2/2001 |
| WO | WO 01/25486 | 4/2001 |
| WO | WO 01/53455 | 7/2001 |
| WO | WO 01/92463 | 12/2001 |
| WO | WO 02/40685 | 5/2002 |
| WO | WO 02/42326 | 5/2002 |
| WO | WO 02/083837 | 10/2002 |
| WO | WO 02/083953 | 10/2002 |
| WO | WO 04/001010 | 12/2003 |
| WO | WO 2004/087069 | 10/2004 |
| WO | WO 2004/087070 | 10/2004 |
| WO | WO 2004/087884 | 10/2004 |
| WO | WO 2005/003316 | 1/2005 |

OTHER PUBLICATIONS

Abelson et al.,1998, "tRNA splicing." Journal of Biological Chemistry 273(21):12685-12688.
Adams et al., 1991, "Fluorescence ratio imaging of cyclic AMP in single cells." Nature 349:694-697.
Baldi et al., 1992, "Participation of the intron in the reaction catalyzed by the Xenopus tRNA splicing endonuclease." Science 255:1404-1408.
Barbino & Kelller, 1999, "Last but not least: regulated poly(A) tail formation." Cell 99(1):9-11.
Belford et al., 1993, "Multiple nucleotide cofactor use by yeast ligase in tRNA splicing. Evidence for independent ATP- and GTP-binding sites" J. Biol. Chem. 268(4):2444-2450.
Belfort, M., & Weiner, A., 1997, "Another bridge between kingdoms: tRNA splicing in archaea and eukaryotes." Cell 89(7):1003-1006.
Bjork, G., 1995, "Biosynthesis and Function of Modified Nucleosides, in tRNA: Structure, Biosynthesis and Function." D. Soll & U. RajBhandary (eds.), American Society for Microbiology, Washington DC: pp. 165-205.
Bujnicki, J.M., & Rychlewski, L., 2000, "Prediction of a common fold for all four subunits of the yeast tRNA splicing endonuclease: implications for the evolution of the EndA/Sen family." FEBS Lett 486: 328-329.
Buvoli et al, 2000, "Suppression of nonsense mutations in cell culture and mice by multimerized suppressor tRNA genes" Molecular and Cellular Biology 20(9):3116-3124.
Calvo, O., and Manley, J.L., 2003, "Strange bedfellows: polyadenylation factors at the promoter." Genes Dev 17(11):1321-1327.
Choi and Dreyfuss, 1984, "Monoclonal antibody characterization of the C proteins of heterogeneous nuclear ribonucleoprotein complexes in vertebrate cells." J. Cell. Biol. 99(6):1997-2004.
Culver et al., 1997, "A 2'-phosphotransferase implicated in tRNA splicing is essential in *Saccharomyces cerevisiae*." J Biol Chem 272:13203-13210.

De Vries, H. et al., 2000, "Human pre-mRNA cleavage factor II(m) contains homologs of yeast proteins and bridges two other cleavage factors." EMBO J 19:5895-5904.
Deutscher, M.P. , 1995 "tRNA Processing Nucleases, in tRNA:Structure, Biosynthesis and Function," D. Soll and U. RjaBhandary (eds.), American Society for Microbiology, Washington DC: pp. 51-65.
Diener & Moore, 1998, "Solution Structure of a Substrate for the Archael Pre-tRNA Splicing Endonucleases: The Bulge-Helix-Bulge Motif." Mol. Cell. 1:883-894.
Fabbri, S et al., 1998, "Conservation of substrate recognition mechanisms by tRNA splicing endonucleases." Science 280, 284-286.
Frank & Pace, 1998, "Ribonuclease P: unity and diversity in a tRNA processing ribozyme." Annu Rev Biochem 67, 153-180.
Fruscoloni et al., 2001, "Cleavage of non-tRNA substrates by eukaryal tRNA splicing endonucleases." EMBO Rep 2(3):217-221.
Gandini-Attardi, et al., 1990, "Transfer RNA splicing endonuclease from *Xenopus laevis*." Methods Enzymol 181:510-517.
Gomes et al., 1997, "RNA splicing ligase activity in the archaeon Haloferax volcanii" Biochem & Biophys. Res. Comm. 237:588-94.
Greer et al., 1982, "Mechanism of action of a yeast RNA ligase in tRNA splicing" Cell 32:537-546.
Greer., 1986, "Assembly of tRNA Splicing Complex: Evidence for Concerted Excision and Joining Steps in Splicing in Vitro." Mol. and Cellular. Bio., 6(2):638-642.
Hirose and Manley, 2000, "RNA polymerase II and the integration of nuclear events." Genes Dev., 14(12):1415-1429.
Hopper, A.K., and Phizicky, E.M., 2003, "tRNA transfers to the limelight." Genes Dev 17(2):162-180.
Huh, et al., 2003, "Global analysis of protein localization in budding yeast." Nature 425:686-691.
Hyde-Deruyscher et al., 2000, "Detection of Small-Molecule Enzyme Inhibitors with Peptides Isolated from Phage-Displayed Combinatorial Peptide Libraries." Chem. & Biol. 7:17-25.
Ikemura, 1985, "Codon Usage and tRNA Content in Unicellular and Multicellular Organisms." Mol. Biol. Evol., 2(1):13-34.
Ikemura, T. and Okeki, H., 1983, "Codon usage and transfer RNA contents: organism-specific codon-choice patterns in reference to the isoacceptor contents." Cold Spring Harbor Symp. Quant. Biol. 47:1087-1097.
Jacobson et al., 1997, "Nuclear domains of the RNA subunit of RNase P." J Cell Sci. 110 ( Pt 7):829-837.
Kleman-Leyer et al., 1997, "Properties of H. volcanii tRNA Intron Endonuclease Reveal a Relationship between the Archaeal and Eucaryal tRNA Intron Processing Systems." Cell., 89:839-847.
Laski, F.A. et al., 1983, "Characterization of tRNA precursor splicing in mammalian extracts." J Biol. Chem. 258(19):11974-11980.
Li & Abelson, 2000, "Crystal Structure of a Dimeric Archaeal Splicing Endonuclease." J. Mol. Biol. 302:639-648.
Li et al., 1998, "Crystal structure and evolution of a transfer RNA splicing enzyme" Science 280(5361):279-284.
Lykke-Andersen, J. & Garrett, R.A., 1997, "RNA-protein interactions of an archaeal homotetrameric splicing endoribonuclease with an exceptional evolutionary history." EMBO J 16(20):6290-6300.
Minvielle-Sebastia, L. & Keller, W., 1999, "mRNA polyadenylation and its coupling to other RNA processing reactions and to transcription." Curr. Opin. Cell. Biol. 11:352-357.
O'Connor, J.P., & Peebles, C.L., 1992, "PTA1, an essential gene of *Saccharomyces cerevisiae* affecting pre-tRNA processing." Mol Cell Biol 12:3843-3856.
Otsuka, et al., 1981, "Ribonuclease 'Xlal' an activity from *Xenopus laevis* oocytes that excises intervening sequences from yeast transfer ribonucleic acid precursors." Mol Cell Biol 1:269-280.
Park & Bhandary, 1998, "Tetracycline-regulated suppression of amber codons in mammalian cells." Mol. & Cell. Biol. 18:4418-4425.
Phizicky et al., 1986, "*Saccharomyces cerevisiae* tRNA ligase. Purification of the protein and isolation of the structural gene" J. of Biol. Chem. 261(6):2978-2986.
Preker et al., 1997, "A multisubunit 3'-end processing factor from yeast containing poly(A) polymerase and homologues of the subunits of mammalian cleavage and polyadenylation specificity factor." EMBO J 16:4727-4737.

Proudfoot, 2000, "Connecting transcription to messenger RNA processing." Trends Biochem Sci. Jun. 2000;25(6):290-3. Review.

Qin & Pyle, 1999, "Site-specific labeling of RNA with fluorophores and other structural probes." Methods 18(1):60-70.

Rauhut et al., 1990, "Yeast tRNA-splicing endonuclease is a heterotrimeric enzyme." J Biol. Chem. 265(30): 18180-18184.

Reyes & Abelson 1988, "Substrate Recognition and Splice Site Determination in Yeast tRNA Splicing." Cell, 55:719-730.

Sarkar & Hopper., 1998, "tRNA Nuclear Export in *Saccharomyces cerevisiae*: In Situ Hybridization Analysis." Mol. Biol. of the Cell., 9:3041-3055.

Saxena et al., 1992, "Angiogenin is a Cytotoxic, tRNA-specific Ribonuclease in the RNase A Superfamily." J. of Biol. Chem. 267(30):21982-21986.

Standring et al., 1981, "Yeast tRNA3Leu gene transcribed and spliced in a HeLa cell extract." Proc. Natl. Acad. Sci. USA 78(10):5963-5967.

Takagaki et al., 2000, "Complex protein interactions within the human polyadenylation machinery identify a novel component." Mol. Cell. Biol. 20:1515-1525.

Takaku et al., 2003, "A candidate prostate cancer susceptibility gene encodes tRNA 3' processing endoribonuclease." Nucleic Acids Res 31(9):2272-2278.

Trotta et al., 1997, "The yeast tRNA splicing endonuclease: a tetrameric enzyme with two active site subunits homologous to the archaeal tRNA endonucleases." Cell 89:849-858.

Trotta, C.R. and Abelson, J.N., 1999, "tRNA Splicing: An RNA World Add-On or an Ancient Reaction? In RNA World II" Tom Cech, Ray Gesteland and John Atkins (eds.), Cold Spring Harbor Laboratory Press, 561-584.

Trotta., 1999, "The Composition, Function and Evolution of the tRNA Splicing Endonuclease." Thesis, California Institute of Technology, pp. 1-147.

Tsien et al., 1993, "FRET for studying intracellular signaling." Trends in Cell. Bio. 3(7): 242-245.

Vaughn et al., 2002, "Methonine In and Out of Proteins: Targets for Drug Design." Curr. Med. Chem. 9(3):385-409.

Volarevic et al., 2000, "Proliferation, But not Growth Blocked by Conditional Deletion of 40S Ribosomal Protein S6." Science 288:2045-2047.

Wahle & Ruegsegger, 1999, "3'-End processing of pre-mRNA in eukaryotes." FEMS Micro Rev., 23(3 ):277-295.

Wallace et al., 1999, "Two distinct forms of the 64,000 Mr protein of the cleavage stimulation factor are expressed in mouse male germ cells." Proc. Natl. Acad. Sci. 96(12):6763-6768.

Wang et al., 1990, "Substrate Masking: Binding of RNA by EGTA-Inactivated Micrococcal Nuclease Resutls in Artifactual Inhibition of RNA Processing Reactions." Nuc. Acids Res. 18(22):6625-6626.

Winter et al., 2000, "RNA polymerase III transcription factor TFIIIC2 is overexpressed in ovarian tumors." Proc. Natl. Acad. Sci., 97(23):12619-12624.

Xiao et al., 2002, "Eukaryotic ribonuclease P: a plurality of ribonucleoprotein enzymes." Annu Rev Biochem 71, 165-189.

Xu et al., 1990, "Purification of yeast transfer RNA ligase." Meth. in Enzymol. 181:463-471.

Yoshihisa et al., 2003, "Possibility of cytoplasmic pre-tRNA splicing: the yeast tRNA splicing endonuclease mainly localizes on the mitochondria." Mol Biol Cell 14(8):3266-3279.

Zhang et al., 1997, "Gene Expression Profiles in Normal and Cancer Cells." Science 276:1268-1272.

Zhao, 1999 "Formation of mRNA 3' ends in eukaryotes: mechanism, regulation, and interrelationships with other steps in mRNA synthesis." Microbiol. Mol. Biol. Rev. 63:405-445.

Reyes et al., 1987, "A synthetic substrate for tRNA splicing." Anal. Biochem. 166(1):90-106.

Greer et al., 1987, "Substrate recognition and identification of splice sites by the tRNA-splicing endonuclease and ligase from *Saccharomyces cerevisiae*." Mol. & Cell. Biol. 7(1): 76-84.

Miao et al.;, 1993, "Yeast tRNA-splicing endonuclease cleaves precurson tRNA in a random pathway." J. Biol. Chem. 268(1): 672-677.

Phizicky et al., 1992, "Yeast tRNA Ligase Mutants are Nonviable and Accumulate tRNA Splicing Intermediates." J. Biol. Chem. 267(7):4577-4582.

Zillman et al., 1991, "Conserved mechanism of tRNA splicing in eukaryotes." Mol. & Cell. Biol. 11(11):5410-5416.

Branden et al., 1991, Chapter 16: Prediction, Engineering, and Design of Protein Structures in Introduction to Protein Structure, Garland Publishing, Inc., p. 247.

Brown, 1993, Hybridization Analysis of DNA Blots, in Current Protocols in Molecular Biology, p. 2.10.1-2.10.11.

Genbank Accesion No. AAH19582, "TRNA splicing" dated Jan. 3, 2002.

Genbank Accession No. BC019582, "*Homo sapiens* TRNA" dated Jan. 3, 2002.

Genbank: Accession No. NP_079541; "tRNA splicing endonuclease 2 homolog [*Homo sapiens*]," dated Mar. 2, 2006.

Genbank: Accession No. NT_005927.12; "*Homo sapiens* chromosome 3 reference genomic contig," dated Aug. 1, 2002.

Genbank: Accession No. NT_011225.9; "*Homo sapiens* chromosome 19 reference genomic contig," dated Aug. 1, 2002.

Genbank: Accession No. XP_085899; "similar to LENG5 protein [*Homo sapiens*]," dated Aug. 1, 2002.

Genbank Accession No. CAA19575, "tRNA-splicing endonuclease subunit Sen34 [*Schizosaccharomyces pombe*]," dated Jun. 30, 2009.

Genbank Accession No. CAA21061, "tRNA-splicing endonuclease subunit Sen54 (predicted) [*Schizosaccharomyces pombe*]," dated Jun. 30, 2009.

Genbank Accession No. CAD27500, "tRNA-splicing endonuclease subunit Sen2 [*Schizosaccharomyces pombe*]," dated Jun. 30, 2009.

Genbank Accession No. CAE46913; "tRNA-splicing endonuclease subunit Sen15 [*Schizosaccharomyces pombe*]," dated Jun. 30, 2009.

Kaminska, 2002, "The isoprenoid biosynthetic pathway in *Saccharomyces cerevisiae* is affected in a maf1-1 mutant with altered tRNA synthesis." FEMS Yeast Res. 2:31-37.

Lucas et al., 2000, "Yeast Sequencing Report: Sequence analysis of two cosmids from the right arm of the *Schizosaccharomyces pombe*chromosome II." Yeast 16:299-306.

Paushkin et al., 2004, "Identification of a human endonuclease complex reveals a link between tRNA splicing and pre-mRNA 3' End Formation." Cell, 117:311-321.

Seffernick et al., 2001, "Melamine deaminase and atrazine chlorohydrolase: 98 percent identical but functionally different." J Bacteriol 183(8):2405-2410.

Sood et al., 2001, "Cloning and characterization of 13 novel transcripts and the human RGS8 gene from the Iq25 region encompassing the hereditary prostate cancer (HPC1) locus." Genomics 73:211-222.

Spaltmann et al., 1999, "Computer-aided target selection—prioritizing targets for antifungal drug discovery." DDT, 4(1):17-26.

Stryer, 1999, Chapter 5: Flow of Genetic Information, p. 96-97; Chapter 33: RNA Synthesis and Splicing, p. 860-864, Chapter 34: Protein Synthesis, p. 875-880; in Biochemistry, 4$^{th}$ edition, W.H. Freeman and Co., New York.

Witkowski, 1999, "Conversion of β-ketoacyl Synthase to Malonyl Decarboxylase by Replacement of the Active-site Cysteine and Glutamine." Biochemistry, 38:11643-11650.

Yeast Accession No. YLR105C; SEN2: http://www.yeastgenome. org/, dated Mar. 8, 2006.

Yeast Accession No. YAR008w; SEN34 http://www.yeastgenome. org/, dated Mar. 8, 2006.

Yeast Accession No. YMR059w; SEN 15 http://www.yeastgenome. org/ dated Mar. 8, 2006.

Yeast Accession No. YPL083c; SEN54 "http://www.yeastgenome. org/," dated Mar. 8, 2006.

Preliminary Amendment, dated Sep. 27, 2005, for U.S. Appl. No. 10/551,304, filed May 18, 2006.

Requirement for Restriction/Election, dated Jan. 16, 2008, for U.S. Appl. No. 10/551,304, filed May 18, 2006.

Response to Requirement for Restriction/Election, dated Jul. 15, 2008, for U.S. Appl. No. 10/551,304, filed May 18, 2006.

Requirement for Restriction/Election, dated Nov. 25, 2008, for U.S. Appl. No. 10/551,304, filed May 18, 2006.

Response to Requirement for Restriction/Election, dated Dec. 22, 2008, for U.S. Appl. No. 10/551,304, filed May 18, 2006.
Non-Final Rejection, dated Mar. 17, 2009, for U.S. Appl. No. 10/551,304, filed May 18, 2006.
Response to Office Communication Regarding Sequence Disclosure and Preliminary Amendment dated Feb. 28, 2006, for U.S. Appl. No. 10/884,695, filed Jul. 2, 2004.
Requirement Restriction/Election dated Jun. 13, 2006 for U.S. Appl. No. 10/884,695, filed Jul. 2, 2004.
Response to Requirement for Restriction/Election and Preliminary Amendment dated Oct. 13, 2006 for U.S. Appl. No. 10/884,695, filed Jul. 2, 2004.
Non-Final Rejection, dated Dec. 21, 2006, for U.S. Appl. No. 10/884,695, filed Jul. 2, 2004.
Amendment after non-final rejection, dated Apr. 17, 2007, for U.S. Appl. No. 10/884,695, filed Jul. 2, 2004.
Non-Final Rejection, dated Jul. 13, 2007, for U.S. Appl. No. 10/884,695, filed Jul. 2, 2004.
Amendment after non-final rejection, dated Nov. 13, 2007, for U.S. Appl. No. 10/884,695, filed Jul. 2, 2004.
Non-Final Rejection, dated Feb. 5, 2008, for U.S. Appl. No. 10/884,695, filed Jul. 2, 2004.
Amendment after non-final rejection, dated Aug. 5, 2008, for U.S. Appl. No. 10/884,695, filed Jul. 2, 2004.
Detailed Action, dated Dec. 1, 2008, for U.S. Appl. No. 10/884,695, filed Jul. 2, 2004.
Notice of Abandonment, dated Jun. 4, 2009, for U.S. Appl. No. 10/884,695, filed Jul. 2, 2004.
Requirement for Restriction/Election, dated Sep. 8, 2008, for U.S. Appl. No. 10/551,300, filed Nov. 29, 2006.
Response to Restriction Requirement and Preliminary Amendment, dated Nov. 10, 2008, for U.S. Appl. No. 10/551,300, filed Nov. 29, 2006.
Notice of Non-compliant, dated Feb. 4, 2009, for U.S. Appl. No. 10/551,300, filed Nov. 29, 2006.
Response to Notice of Non-compliant, dated Mar. 2, 2009, for U.S. Appl. No. 10/551,300, filed Nov. 29, 2006.
Non-Final Rejection, dated, May 22, 2009, for U.S. Appl. No. 10/551,300, filed Nov. 29, 2006.
International Search Report, dated Jun. 22, 2005 of PCT/US2004/009572, filed Mar. 26, 2004.
Written Opinion, dated Jun. 22, 2005 of PCT/US2004/009572, filed Mar. 26, 2004.
International Preliminary Report on Patentability, dated Nov. 11, 2005 of PCT/US2004/009572, filed Mar. 26, 2004.
European Search Report, dated Jul. 23, 2007 of EP 1 613 158 published Jan. 11, 2006.
International Search Report, dated Jan. 27, 2005 of PCT/US2004/009590, filed Mar. 26, 2004.
Written Opinion, dated Jan. 27, 2005 of PCT/US2004/009590, filed Mar. 26, 2004.
International Preliminary Report on Patentability, dated Jun. 16, 2005 of PCT/US2004/009590, filed Mar. 26, 2004.
European Search Report, dated Jul. 23, 2007 of EP 1 613 160 published Jan. 11, 2006.
International Search Report, dated Apr. 24, 2007 of PCT/US2004/021334, filed Jul. 2, 2004.
Written Opinion, dated Apr. 24, 2007 of PCT/US2004/021334, filed Jul. 2, 2004.
International Preliminary Report on Patentability, Dec. 12, 2007 of PCT/US2004/021334, filed Jul. 2, 2004.
European Search Report, dated May 8, 2009 of EP 1 649 002 published Apr. 26, 2006.
International Search Report, dated Jun. 9, 2005 of PCT/US2004/009574, filed Mar. 26, 2004.
Written Opinion, dated Jun. 9, 2005 of PCT/US2004/009574, filed Mar. 26, 2004.
International Preliminary Report on Patentability, dated Nov. 11, 2005 of PCT/US2004/009574, filed Mar. 26, 2004.
European Search Report, dated Jul. 3, 2007 of EP 1 613 159 published Jan. 11, 2006.

European communication regarding possible amendment of claims/payment of fees, dated Nov. 14, 2005, of EP 1 613 158, published Jan. 11, 2006.
Reply to European communication before examination dated Dec. 21, 2005, of EP 1 613 158, published Jan. 11, 2006.
European communication regarding transmission of search report, dated Jul. 23, 2007, of EP 1 613 158, published Jan. 11, 2006.
European communication from the examining division, dated Nov. 16, 2007, of EP 1 613 158, published Jan. 11, 2006.
Reply to European communication from the examining division, dated May 15, 2008, of EP 1 613 158, published Jan. 11, 2006.
European communication from the examining division, dated Jul. 15, 2008, of EP 1613 158, published Jan. 11, 2006.
Reply to European communication from the examining division, dated Nov. 10, 2008, of EP 1 613 158, published Jan. 11, 2006.
European communication from the examining division, dated Nov. 26, 2008, of EP 1 613 158, published Jan. 11, 2006.
Reply to European communication from the examining division, dated Jan. 26, 2009, of EP 1 613 158, published Jan. 11, 2006.
European communication regarding transmission of search report, dated Jul. 3, 2007, of EP 1 613 159, published Jan. 11, 2006.
European communication from the examining division, dated Oct. 10, 2007, of EP 1 613 159, published Jan. 11, 2006.
Reply to European communication from the examining division, dated Apr. 21, 2008, of EP 1 613 159, published Jan. 11, 2006.
European communication from the examining division , dated Aug. 5, 2008, of EP 1 613 159, published Jan. 11, 2006.
Reply to European communication from the examining division, dated Aug. 18, 2008, of EP 1 613 159, published Jan. 11, 2006.
European communication from the examining division, dated Dec. 17, 2008, of EP 1 613 159, published Jan. 11, 2006.
Reply to European communication from the examining division, dated Jun. 26, 2009, of EP 1 613 159, published Jan. 11, 2006.
European communication regarding possible amendment of claims/payment of fees, dated Nov. 14, 2005, of EP 1 613 160, published Jan. 11, 2006.
European communication regarding transmission of search report, dated Jul. 23, 2007, of EP 1 613 160, published Jan. 11, 2006.
European communication from the examining division, dated Apr. 23, 2008, of EP 1 613 160, published Jan. 11, 2006.
Reply to European communication from the examining division, dated Oct. 31, 2008, EP 1 613 160, published Jan. 11, 2006.
European communication from the examining division, dated Dec. 17, 2008, of EP 1 613 160, published Jan. 11, 2006.
Reply to European communication from the examining division, dated Jun. 26, 2009, of EP 1 613 160, published Jan. 11, 2006.
Genbank Accession No. M32336, "S.cerevisiae tRNA splicing endonuclease beta-subunit (SEN2) gene, complete cds," dated Aug. 6, 1997.
Response to Non-Final Rejection, dated Aug. 17, 2009, for U.S. Appl. No. 10/551,304, filed May 18, 2006.
Response to Non-Final Rejection, dated Aug. 19, 2009, for U.S. Appl. No. 10/551,300, filed Nov. 29, 2006.
Spingola et al., 1999. Genome-wide bioinformatic and molecular analysis of introns in *Saccharomyces cerevisiae*, RNA, 5:221-234.
Preliminary Amendment dated Sep. 27, 2005, for PCT/US2004/009572—U.S. Appl. No. 10/551,301, filed Jul. 12, 2006.
Preliminary Amendment dated Aug. 4, 2008, for U.S. Appl. No. 10/551,301, filed Jul. 12, 2006.
Requirement for Restriction/Election, dated Jan. 16, 2009, for U.S. Appl. No. 10/551,301, filed Jul. 12, 2006.
Response to requirement for Restriction/Election, dated Feb. 17, 2009, for U.S. Appl. No. 10/551,301, filed Jul. 12, 2006.
Non-Final Rejection, dated May 12, 2009, for U.S. Appl. No. 10/551,301, filed Jul. 12, 2006.
Marras, 2002, "Efficiencies of fluorescence resonance energy transfer and contact-mediated quenching in oligonucleotide probes.", Nucleic Acids Research 30:e122.
Herrenknecht, 1988, "Pre-tRNA splicing in a nuclear extract from human leukaemia cells: separation of endonuclease and ligase activities", Nucleic Acids Research 16:7713-4.

Kohrer et al., 1990, "A yeast tRNA precursor containing a pre-mRNA intron is spliced via the pre-mRNA splicing mechanism", EMBO J, 9(3):705-9.

Final Rejection, dated Dec. 2, 2009, for U.S. Appl. No. 10/551,300, filed Nov. 29, 2006.

Final Rejection, dated Dec. 9, 2009, for U.S. Appl. No. 10/551,301, filed Jul. 12, 2006.

Final Rejection, dated Nov. 12, 2009, for U.S. Appl. No. 10/551,304, filed May 18, 2006.

Response to Final Rejection, dated Apr. 12, 2010, for U.S. Appl. No. 10/551,304, filed May 18, 2006.

Response to Non-Final Rejection, dated Sep. 10, 2009, for U.S. Appl. No. 10/551,301, filed Jul. 12, 2006.

European communication from the examining division, dated Dec. 1, 2009, of EP 1 613 158, published Jan. 11, 2006.

European communication from the examining division, dated Dec. 1, 2009, of EP 1 613 159, published Jan. 11, 2006.

European communication from the examining division, dated Dec. 1, 2009, of EP 1 613 160, published Jan. 11, 2006.

Reply to European communication from the examining division, dated Jun. 9, 2010, of EP 1 613 158, published Jan. 11, 2006.

Reply to European communication from the examining division, dated Jun. 9, 2010, of EP 1 613 159, published Jan. 11, 2006.

Communication with enclosed Partial European Search Report, dated Mar. 10, 2011, of Application No. EP 10184004.9.

Spinelli et al., 1997, "A conditional lethal yeast phosphotransferase (tpt1) mutant accumulates tRNAs with a 2'-phosphate and an undermodified base at the splice junction", RNA. (12):1388-1400.

Culver et al., 1993, "An NAD derivative produced during transfer RNA splicing: ADP-ribose 1"-2" cyclic phosphate", Science, 261(5118):206-208.

```
                1                                                              50
Hs Sen2p      MAEAVFHAPK RKRRVYETYE SPLPIPFGQD HGPLKEFKIF RAEMINNNVI
Hs Sen2 var.  MAEAVFHAPK RKRRVYETYE SPLPIPFGQD HGPLKEFKIF RAEMINNNVI
Sc Sen2p      ---------- ---------- ---------- ---------- ----------

51                                                             100
Hs Sen2p      VRNAEDIEQL YGKGYFGKGI LSRSRPSFTI SDPKLVAKWK DMKTNMPI..
Hs Sen2 var.  VRNAEDIEQL YGKGYFGKGI LSRSRPSFTI SDPKLVAKWK DMKTNMPI..
Sc Sen2p      ---------- ---------- ---------- -MSKGRVNQK RYKYPLPIHP 101                                                            150
Hs Sen2p      ...ITSKRYQ HSVEWAAELM RRQGQDESTV RRILKDYTKP LE.HPPVKRN
Hs Sen2 var.  ...ITSKRYQ HSVEWAAELM RRQGQDESTV RRILKDYTKP LE.HPPVKRN
Sc Sen2p      VDDLPELILH NPLSWLYWAY RYYKSTNALN DKVHVDFIGD TTLHITVQ..

151                                                            200
Hs Sen2p      EEAQVHDKLN SGMVSNMEGT AGGERPSVVN GDSGKSGGVG DPREPLGCLQ
Hs Sen2 var.  EEAQVHDKLN SGMVSNMEGT AGGERPSVVN GDSGKSGGVG DPREPLGCLQ
Sc Sen2p      DDKQMLYLWN NGFFGT..GQ FSRSEPTWKA RTEARLGLND TPLHNRGGTK 201                                                            250
Hs Sen2p      EGSGCHPTTE SFEKSVR.ED ASPLPHVCCC KQDALILQRG LHHEDGSQHI
Sen2_Variant  EGSGCHPTTE SFEKSVR.ED ASPLPHVCCC KQDALILQRG LHHEDGSQHI
Sc Sen2p      SNTETEMTLE KVTQQRRLQR LEFKKERAKL ERELLELRKK GGHID.EENI 251                                                            300
Hs Sen2p      GLLHPGDRGP DHEYVLVEEA ECAMSEREAA PNEELVQRNR LICRRNPYRI
Hs Sen2 var.  GLLHPGDRGP DHEYVLVEEA ECAMSEREAA PNEELVQRNR LICRRNPYRI
Sc Sen2p      LLEKQRESLR KFKLKQTEDV GIVAQQQDIS ESNLRDEDNN LLDENGDLLP 301                                                            350
Hs Sen2p      FEYLQLSLEE AFFLVYALGC LSIYYEKEPL TIVKLWKAFT VVQPTFRTTY
Hs Sen2 var.  FEYLQLSLEE .......... .......EPL TIVKLWKAFT VVQPTFRTTY
Sc Sen2p      LESLELMPVE AMFLTFALPV LDISPACLAG KLFQFDAKYK DIH.SFVRSY 351                                                            400
Hs Sen2p      MAYHYFRSKG WVPKVGLKYG TDLLIYRKGP PFYHASYSVI IELVDDHFEG
Hs Sen2 var.  MAYHYFRSKG WVPKVGLKYG TDLLIYRKGP PFYHASYSVI IELVDDHFEG
Sc Sen2p      VIYHHYRSHG WCVRSGIKFG CDYLIYKRGP PFQHAEFCV. ..MGLDH...

401                                                            450
Hs Sen2p      SLRRPLSWKS LAALSRVSVN VSKELMLCYL IKPSTMTD.. ...KEMESPE
Hs Sen2 var.  SLRRPLSWKS LAALSRVSVN VSKELMLCYL IKPSTMTD.. ...KEMESPE
Sc Sen2p      DVSKDYTWYS ..SIARVVGG AKKTFVLCYV ERLISEQEAI ALWKSNNFTK 451                  477
Hs Sen2p      CMKRIKVQEV ILSRWVSSRE RSDQDDL
Hs Sen2 var.  CMKRIKVQEV ILSRWVSSRE RSDQDDL
Sc Sen2p      LFNSFQVGEV LYKRWVPGRN RD-----
```

FIG. 2

METHODS OF IDENTIFYING COMPOUNDS THAT TARGET TRNA SPLICING ENDONUCLEASE AND USES OF SAID COMPOUNDS AS ANTI-PROLIFERATIVE AGENTS

This application is a continuation of U.S. application Ser. No. 10/551,301, filed Jul. 12, 2006, now abandoned which is a national stage under 35 U.S.C. §371 of International Application No. PCT/US04/09572, filed Mar. 26, 2004, which claims benefit of U.S. Provisional Application No. 60/458,079, filed Mar. 27, 2003. U.S. application Ser. No. 10/551,301, filed Jul. 12, 2006, is incorporated by reference herein in its entirety.

1. INTRODUCTION

The present invention relates to a method for screening and identifying compounds that modulate the activity of an animalia tRNA splicing endonuclease. In particular, the invention provides assays for the identification of compounds that inhibit or reduce the activity of an animalia tRNA splicing endonuclease. The methods of the present invention provide a simple, sensitive assay for high-throughput screening of libraries of compounds to identify pharmaceutical leads useful for preventing, treating, managing or ameliorating cancer or one or more symptoms thereof.

2. BACKGROUND OF THE INVENTION

2.1 Cancer and Neoplastic Disease

Cancer is the second leading cause of death in the United States. The American Cancer Society estimated that in 2001, there would be 1.3 million new cases of cancer and that cancer will cause 550,000 deaths. Overall rates have declined by 1% per year during the 1990s. There are 9 million Americans alive who have ever had cancer. NIH estimates the direct medical costs of cancer as $60 billion.

Currently, cancer therapy involves surgery, chemotherapy and/or radiation treatment to eradicate neoplastic cells in a patient (see, for example, Stockdale, 1998, "Principles of Cancer Patient Management", in *Scientific American: Medicine*, vol. 3, Rubenstein and Federman, eds., Chapter 12, Section IV). All of these approaches pose significant drawbacks for the patient. Surgery, for example, can be contraindicated due to the health of the patient or can be unacceptable to the patient. Additionally, surgery might not completely remove the neoplastic tissue. Radiation therapy is effective only when the irradiated neoplastic tissue exhibits a higher sensitivity to radiation than normal tissue, and radiation therapy can also often elicit serious side effects. (Id.) With respect to chemotherapy, there are a variety of chemotherapeutic agents available for treatment of neoplastic disease. However, despite the availability of a variety of chemotherapeutic agents, traditional chemotherapy has many drawbacks (see, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy can cause significant, and often dangerous, side effects, including severe nausea, bone marrow depression, immunosuppression, etc. Additionally, many tumor cells are resistant or develop resistance to chemotherapeutic agents through multidrug resistance.

Therefore, there is a significant need in the art for novel compounds and compositions, and methods that are useful for treating cancer or neoplastic disease with reduced or without the aforementioned side effects. Further, there is a need for cancer treatments that provide cancer-cell-specific therapies with increased specificity and decreased toxicity.

2.2 tRNA Production

Maturation and maintenance of tRNA within eucaryal cells requires several processing events including 5' and 3' end-trimming, modification of specific bases and in some cases, intron removal. The enzymes for these various steps in processing have been characterized in the yeast, archaeal, mammalian and bacterial systems (Deutscher, M. P. tRNA Processing Nucleases, in tRNA:Structure, Biosynthesis and Function, D. Soll and U. RjaBhandary (eds.), American Society for Microbiology, Washington D.C., (1995), pp. 51-65). 5' end trimming requires the activity of Rnase P and 3' end trimming requires the function of various endo- and exonucleases. Modification occurs through interaction of tRNA with various modification enzymes. Most tRNAs contain a number of global as well as, species-specific modifications (Bjork, G. Biosynthesis and Function of Modified Nucleosides, in tRNA: Structure, Biosynthesis and Function, D. Soll and U. RajBhandary (eds.), American Society for Microbiology, Washington D.C., (1995), pp. 165-205). In archaea and eucarya, several isoaccepting groups of tRNA contain intervening sequences ranging in size from 14-105 nucleotides (Trotta, C. R. and Abelson, J. N. tRNA Splicing: An RNA World Add-On or an Ancient Reaction? In RNA World II, Tom Cech, Ray Gesteland and John Atkins (eds.), Cold Spring Harbor Laboratory Press (1999) and Abelson et al., 1998, Journal of Biological Chemistry 273:12685-12688). Removal of the intron requires the activity of 3 enzymes. In the first step, the tRNA is recognized and cleaved at the 5' and 3' junction by the tRNA splicing endonuclease. The archaeal and eucaryal tRNA endonuclease are evolutionary conserved enzymes and contain a similar active site to achieve cleavage at the 5' and 3' splice sites. However, they have diverged to recognize the tRNA substrate in a different manner. The archaeal enzyme recognizes a conserved intronic structure known as the bulge-helix-bulge. This structure is comprised of two 3-nucleotide bulges separated by a 4-nucleotide helix. Cleavage occurs within each bulge to release the intron. The eucaryal endonuclease recognizes the tRNA substrate in a mature domain dependent fashion, measuring a set distance from the mature domain to the 5' and 3' splice sites (Reyes et al., 1988, Cell 55:719-730). It has recently been demonstrated, however, that the eucaryal enzyme requires a bulge at each splice site and that the enzyme has actually retained the ability to recognize tRNA by an intron-dependent recognition mechanism identical to that of the archaeal endonuclease (Fruscoloni et al., 2001, EMBO Rep 2:217-221). Once cleaved, the tRNA half molecules are ligated by the action of a unique tRNA splicing ligase (Trotta, C. R. and Abelson, J. N. tRNA Splicing: An RNA World Add-On or an Ancient Reaction? In RNA World II, Tom Cech, Ray Gesteland and John Atkins (eds.), Cold Spring Harbor Laboratory Press (1999) and Abelson et al., 1998, Journal of Biological Chemistry 273:12685-12688). In yeast, the product of ligation is a tRNA with a phosphate at the splice junction. Removal of the phosphate is carried out by a tRNA 2'-phosphotransferase to yield a mature tRNA product (Trotta, C. R. and Abelson, J. N. tRNA Splicing: An RNA World Add-On or an Ancient Reaction? In RNA World II, Tom Cech, Ray Gesteland and John Atkins (eds.), Cold Spring Harbor Laboratory Press (1999) and Abelson et al., 1998, Journal of Biological Chemistry 273:12685-12688).

tRNA is an important component in the translational machinery and is quite stable compared to various other protein-based components (elongation factors, amino-acyl synthetases, etc.). tRNA molecules have very long half-lives. Furthermore, like rRNA and ribosomes, tRNA is present in excess within the cytoplasm of actively growing cells (Ikemura, T. and Okeki, H., 1983, Cold Spring Harbor Symp. Quant. Biol. 47:1087-1097). Thus, specific targeting of tRNA molecules allows a selective inhibition of uncontrolled cell proliferation and not cell growth.

Citation of any of the reference herein is not to be construed as an admission of its availability as prior art.

3. SUMMARY OF THE INVENTION

The present invention provides methods for identifying a compound that modulates the activity of an animalia tRNA splicing endonuclease. In particular, the invention provides methods for identifying a compound that inhibits the activity of an animalia tRNA splicing endonuclease. The invention encompasses the use of the compounds identified utilizing the methods of the invention for the prevention, treatment, management or amelioration of a proliferative disorder or a symptom thereof.

The invention provides cell-based and cell-free assays for the identification of a compound that modulates the activity of an animalia tRNA splicing endonuclease, preferably a mammalian tRNA splicing endonuclease and most preferably a human tRNA splicing endonuclease. These assays may be reporter gene-based assays, fluorescence resonance energy transfer ("FRET")-based assays, or fluorescence polarization assays and may be conducted in a high throughput screen format. Further, these assays directly or indirectly measure the ability of a compound to modulate an animalia tRNA splicing endonuclease. In a preferred embodiment, the ability of a compound to modulate animalia tRNA splicing endonuclease activity that was identified utilizing an indirect assay (e.g., a cell-based assay such as a reporter gene cell-based assay or a FRET cell-based assay) is confirmed utilizing a more direct assay (e.g., a FISH assay).

The reporter gene-based assays may be conducted by contacting a compound with an animalia cell genetically engineered to express a nucleic acid comprising a reporter gene, wherein the reporter gene comprises a tRNA intron, and measuring the expression of said reporter gene. Alternatively, the reporter gene-based assays may be conducted by contacting a compound with an animalia cell-free extract and a nucleic acid comprising a reporter gene, wherein the reporter gene comprises a tRNA intron, and measuring the expression of said reporter gene. The alteration in reporter gene expression relative to a previously determined reference range, or to the expression in the absence of the compound or the presence of an appropriate control (e.g., a negative control) in such reporter-gene based assays indicates that a particular compound modulates the activity of the tRNA splicing endonuclease. In particular, a decrease in reporter gene expression relative to a previously determined reference range, or to the expression in the absence of the compound or the presence of an appropriate control (e.g., a negative control) in such reporter-gene based assays indicates that a particular compound reduces or inhibits the activity of an animalia tRNA splicing endonuclease (e.g., the recognition or cleavage of a tRNA intron). In contrast, an increase in reporter gene expression relative to a previously determined reference range, or to the expression in the absence of the compound or the presence of an appropriate control (e.g., a negative control) in such reporter-gene based assays indicates that a particular compound enhances the activity of an animalia tRNA splicing endonuclease.

In one embodiment, the invention provides a method for identifying a compound that modulates animalia tRNA splicing endonuclease activity, said method comprising: (a) expressing a nucleic acid comprising a reporter gene in a cell, wherein the reporter gene comprises a tRNA intron; (b) contacting said cell with a member of a library of compounds; and (c) detecting the expression of said reporter gene, wherein a compound that modulates tRNA splicing endonuclease activity is identified if the expression of said reporter gene in the presence of a compound is altered relative to a previously determined reference range, or the expression of said reporter gene in the absence of the compound or the presence of an appropriate control (e.g., a negative control).

In another embodiment, the invention provides a method for identifying a compound that modulates animalia tRNA splicing endonuclease activity, said method comprising: (a) contacting a member of a library of compounds with a cell containing a nucleic acid comprising a reporter gene, wherein the reporter gene comprises a tRNA intron; and (b) detecting the expression of said reporter gene, wherein a compound that modulates tRNA splicing endonuclease activity is identified if the expression of said reporter gene in the presence of a compound is altered relative to a previously determined reference range, or the expression of said reporter gene in the absence of said compound or the presence of an appropriate control (e.g., a negative control).

In another embodiment, the invention provides a method for identifying a compound that modulates animalia tRNA splicing endonuclease activity, said method comprising: (a) contacting a member of a library of compounds with a cell-free extract and a nucleic acid comprising a reporter gene, wherein the reporter gene comprises a tRNA intron; and (b) detecting the expression of said reporter gene, wherein a compound that modulates tRNA splicing endonuclease activity is identified if the expression of said reporter gene in the presence of a compound is altered relative to a previously determined reference range, or the expression of said reporter gene in the absence of said compound or the presence of an appropriate control (e.g., a negative control).

In accordance with the invention, the step of contacting a compound with a cell, or cell-free extract and a nucleic acid in the reporter gene-based assays described herein is preferably conducted in an aqueous solution comprising a buffer and a combination of salts (such as KCl, NaCl and/or $MgCl_2$). The optimal concentration of each salt used in the aqueous solution is dependent on the endonuclease and the compounds used, and can be determined using routine experimentation. In a specific embodiment, the aqueous solution approximates or mimics physiologic conditions. In another specific embodiment, the aqueous solution further comprises a detergent or a surfactant.

The reporter gene constructs utilized in the reporter gene-based assays described herein may comprise the coding region of a reporter gene and a tRNA intron that renders the mRNA coding the reporter gene out of frame. Alternatively, the reporter gene constructs utilized in the reporter gene-based assays described herein comprise a tRNA intron within the 5' untranslated region, 3' untranslated region or both the 5' and 3' untranslated regions. In another alternative, the tRNA intron interrupts an mRNA splicing element. In a specific embodiment, a reporter gene construct utilized in the reporter gene-based assays described herein comprises the coding region of a reporter gene and a tRNA intron within the open reading frame of the reporter gene. The intron utilized in the reporter gene constructs described herein may comprise a bulge-helix-bulge conformation. In a preferred embodiment, a reporter gene construct utilized in the reporter-gene-based assays described herein comprises a mature domain containing a tRNA intron.

Any reporter gene well-known to one of skill in the art may be utilized in the reporter gene constructs described herein. Examples of reporter genes include, but are not limited to, the gene encoding firefly luciferase, the gene coding renilla luciferase, the gene encoding click beetle luciferase, the gene encoding green fluorescent protein, the gene encoding yellow fluorescent protein, the gene encoding red fluorescent protein, the gene encoding cyan fluorescent protein, the gene encoding blue fluorescent protein, the gene encoding beta-galactosidase, the gene encoding beta-glucoronidase, the gene encoding beta-lactamase, the gene encoding chloramphenicol acetyltransferase, and the gene encoding alkaline phosphatase.

The reporter gene-based assays described herein may be conducted in a cell genetically engineered to express a reporter gene or in vitro utilizing a cell-free extract. Any cell or cell line of any species well-known to one of skill in the art may be utilized in accordance with the methods of the invention. Further, a cell-free extract may be derived from any cell or cell line of any species well-known to one of skill in the art. Examples of cells and cell types include, but are not limited to, human cells, cultured mouse cells, cultured rat cells or Chinese hamster ovary ("CHO") cells.

Fluorescent resonance energy transfer ("FRET") assays may be used to identify a compound that modulates the activity of an animalia tRNA splicing endonuclease. The FRET assays may be conducted utilizing labeled subunits of an animalia tRNA splicing endonuclease or labeled substrates for an animalia tRNA splicing endonuclease. The FRET cell-based assays may be conducted by microinjecting or transfecting a substrate for an animalia tRNA splicing endonuclease into an animalia cell and contacting the cell with a compound, wherein the substrate is labeled at the 5' end with a fluorophore and labeled at the 3' end with a quencher, or, alternatively, the substrate is labeled at the 5' end with a quencher and labeled at the 3' end with a fluorophore, and measuring the fluorescence of the substrate by, e.g., fluorescence microscopy or a fluorescence emission detector such as a Viewlux or Analyst. The endogenous tRNA splicing endonuclease will cleave the substrate and result in the production of a detectable fluorescent signal. A compound that inhibits or reduces the activity of the endogenous tRNA splicing endonuclease will inhibit or reduce the cleavage of the substrate and thus, inhibit or reduce the production of a detectable fluorescent signal. A compound that enhances the activity of the endogenous endonuclease will enhance the cleavage of the substrate and thus, increase the production of a detectable fluorescent signal. Alternatively, the FRET cell-based assays may be conducted by microinjecting or transfecting a substrate for an animalia tRNA splicing endonuclease into a cell and contacting the cell with a compound, wherein the substrate is labeled at the 5' end with a fluorescent donor moiety and labeled at the 3' end with a fluorescent acceptor moiety, or alternatively, the substrate is labeled at the 5' end with a fluorescent acceptor moiety and labeled at the 3' end with a fluoroscent donor moiety, and measuring the fluorescence of the substrate by, e.g., fluoresence microscopy or a fluorescence emission detector such as a Viewlux or Analyst. The endogenous tRNA splicing endonuclease will cleave the substrate and result in a decrease in the fluorescence emission by the fluorescent donor moiety and fluorescent acceptor moiety at the wavelength of the fluorescent donor moiety. A compound that inhibits or reduces the activity of the endogenous tRNA splicing endonuclease will inhibit or reduce cleavage of the substrate and thus, increase the fluorescence emission of the fluorescent acceptor moiety at the wavelength of the fluorescent donor moiety. A compound that enhances the activity of the endogenous tRNA splicing endonuclease will enhance the cleavage of the substrate and thus, reduce the fluorescence emission of the fluorescent acceptor moiety at the wavelength of the fluorescent donor moiety.

Optionally, an agent known to inhibit or reduce the activity of an animalia tRNA splicing ligase such as an antibody that specifically binds to an animalia tRNA splicing ligase is included in the contacting step of the FRET assays to exclude the possibility that the compound is solely inhibiting or reducing the activity of the ligase. Alternatively, an animalia cell or an animalia cell-free extract that is deficient in tRNA splicing ligase is used in the FRET assays. As another alternative, ATP may be excluded from the assay. Without being bound by theory, since the ligase reaction requires ATP, any effect of a compound in the FRET assay in the absence of ATP cannot be attributed to an effect on the ligase reaction and is therefore an effect on an animalia tRNA splicing endonuclease.

In one embodiment, the invention provides a method of identifying an antiproliferative compound that inhibits or reduces animalia tRNA splicing endonuclease activity, said method comprising: (a) microinjecting or transfecting a substrate of a tRNA splicing endonuclease into an animalia cell, wherein the substrate is labeled at the 5' end with a fluorophore and labeled at the 3' end with a quencher, or, alternatively, the substrate is labeled at the 5' end with a quencher and labeled with a fluorophore; (b) contacting the cell with a member of a library of compounds; and (c) measuring the activity of the tRNA splicing endonuclease, wherein an antiproliferative compound that inhibits or reduces tRNA splicing activity is identified if a fluorescent signal is not detectable in the presence of the compound relative to the absence of the compound or the presence of a negative control. In another embodiment, the invention provides a method of identifying an antiproliferative compound that inhibits or reduces animalia tRNA splicing endonuclease activity, said method comprising: (a) contacting an animalia cell containing a substrate of a tRNA splicing endonuclease with a member of a library of compounds, wherein the substrate is labeled at the 5' end with a fluorophore and labeled at the 3' end with a quencher, or, alternatively, the substrate is labeled at the 5' end with a quencher or labeled at the 3' end with a fluorophore; and (b) measuring the activity of the tRNA splicing endonuclease, wherein an antiproliferative compound that inhibits or reduces tRNA splicing activity is identified if a fluorescent signal is not detectable in the presence of the compound relative to the absence of the compound or the presence of a negative control.

In another embodiment, the invention provides a method of identifying an antiproliferative compound that inhibits or reduces animalia tRNA splicing endonuclease activity, said method comprising: (a) microinjecting or transfecting a substrate of a tRNA splicing endonuclease into a animalia cell, wherein said substrate is labeled at the 5' end with a fluorescent donor moiety and labeled at the 3' end with a fluorescent acceptor moiety, or, alternatively, the substrate is labeled with at the 5' end with a fluorescent acceptor moiety and labeled at the 3' end with a fluorescent donor moiety; (b) contacting the cell with a member of a library of compounds; and (c) measuring the activity of the tRNA splicing endonuclease, wherein an antiproliferative compound that inhibits or reduces tRNA splicing endonuclease activity is identified if the fluorescence emission of the fluorescent acceptor moiety at the wavelength of the fluorescent donor moiety in the presence of the compound is increased relative to the absence of the compound or the presence of a negative control. In another embodiment, the invention provides a method of identifying an antiproliferative compound that inhibits or reduces animalia tRNA splicing endonuclease activity, said method comprising: (a) contacting an animalia cell containing substrate of a tRNA splicing endonuclease with a member of a library of compounds, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety; and (b) measuring the activity of the tRNA splicing endonuclease, wherein an antiproliferative compound that inhibits or reduces tRNA splicing endonuclease activity is identified if the fluorescence emission of the fluorescent acceptor moiety at the wavelength of a fluorescent donor moiety in the presence of the compound is increased relative to the absence of the compound or the presence of a negative control.

The FRET cell-free-based assays may be conducted by contacting a substrate for an animalia tRNA splicing endonuclease with an animalia cell-free extract (preferably, a tRNA splicing endonuclease extract) or a purified animalia tRNA splicing endonuclease and a compound, wherein the substrate is labeled at the 5' end with a fluorophore and labeled at the 3' end with a quencher, or, alternatively, the substrate is labeled at the 5' end with a quencher and labeled at the 3' end with a fluorophore, and measuring the fluorescence of the substrate by, e.g., a fluorescence emission detector such as a Viewlux or Analyst. The tRNA splicing endonuclease in the animalia cell-free extract or the purified animalia tRNA splicing endonuclease will cleave the substrate and result in the production of a detectable fluorescent signal. A compound that inhibits the activity of the animalia tRNA splicing endonuclease will inhibit or reduce the cleavage of the substrate and thus, inhibit or reduce the production of a detectable fluorescent signal. A compound that enhances the activity of the animalia tRNA splicing endonuclease will enhance the cleavage of the substrate and thus, increase the production of a detectable fluorescent signal. Alternatively, the FRET cell-free-based assays may be conducted by contacting a substrate for an animalia tRNA splicing endonuclease with an animalia cell-free extract or a purified animalia tRNA splicing endonuclease and a compound, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety, and measuring the fluorescence of the substrate by, e.g., a fluorescence emission detector such as a Viewlux or Analyst. The tRNA splicing endonuclease in the animalia cell-free extract or the purified animalia tRNA splicing endonuclease will cleave the substrate and result in the production of a detectable fluorescent signal by the fluorescent donor moiety and fluorescent acceptor moiety at the wavelength of the fluorescent donor moiety. A compound that inhibits the activity of the tRNA splicing endonuclease will inhibit or reduce cleavage of the substrate and thus, increase the fluorescence emission of the fluorescent acceptor moiety at the wavelength of the fluorescent donor moiety. A compound that enhances the activity of the endogenous tRNA splicing endonuclease will enhance the cleavage of the substrate and thus, reduce the fluorescence emission of the fluorescent acceptor moiety at the wavelength of the fluorescent donor moiety.

In one embodiment, the invention provides a method of identifying an antiproliferative compound that inhibits or reduces animalia tRNA splicing endonuclease activity, said method comprising: (a) contacting an animalia cell-free extract (preferably, a tRNA splicing endonuclease extract) or a purified animalia tRNA splicing endonuclease with a substrate of a tRNA splicing endonuclease and a member of a library of compounds, wherein the substrate is labeled at the 5' end with a fluorophore and at the 3' end with a quencher, or, alternatively, the substrate is labeled at the 5' end with a quencher and labeled at the 3' end with a fluorophore; and (b) measuring the activity of the tRNA splicing endonuclease, wherein an antiproliferative compound that inhibits or reduces tRNA splicing endonuclease activity is identified if a reduced fluorescent signal is detectable in the presence of the compound relative to the absence of the compound or the presence of a negative control. In another embodiment, the invention provides a method of identifying an antiproliferative compound that inhibits or reduces animalia tRNA splicing endonuclease activity, said method comprising: (a) contacting an animalia cell-free extract (preferably, a tRNA splicing endonuclease extract) or a purified animalia tRNA splicing endonuclease with a substrate of a tRNA splicing endonuclease and a member of a library of compounds, wherein said substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety; and (b) measuring the activity of the tRNA splicing endonuclease, wherein an antiproliferative compound that inhibits or reduces tRNA splicing endonuclease activity is identified if the fluorescence emission of the fluorescent acceptor moiety at the wavelength of the fluorescent donor moiety in the presence of the compound is increased relative to the absence of the compound or the presence of a negative control The substrates for a tRNA splicing endonuclease utilized in the FRET assays described herein comprise an intron. In a preferred embodiment, the substrate for a tRNA splicing endonuclease utilized in the FRET assays described herein comprises a tRNA intron. The intron may have a bulge-helix-bulge conformation In a preferred embodiment, the substrate comprises a mature domain that contains an intron.

The effect of a compound on the activity of an animalia tRNA splicing endonuclease may be determined utilizing a fluorescence polarization-based assay. In such an assay, a fluorescently labeled substrate for an animalia tRNA splicing endonuclease is contacted with an animalia cell-free extract or a purified animalia tRNA splicing endonuclease and a compound or member of a library of compounds; and the fluorescent polarized light emitted is measured utilizing techniques well-known to one of skill in the art or described herein, wherein an alteration in the fluorescently polarized light emitted relative to a control or the absence of the compound or the member of a library of compounds indicates that the compound or member of a library of compounds modulates animalia tRNA splicing endonuclease activity.

Further, the effect of a compound on the activity of an animalia tRNA splicing endonuclease may be determined utilizing a tRNA endonuclease suppression assay. In such an assay, a host cell is engineered to contain a reporter gene and a suppressor tRNA, wherein the reporter gene construct comprises a reporter gene with a nonsense codon in its open reading frame such that the open reading frame is interrupted and the suppressor tRNA's expression is regulated by an inducible regulatory element and the suppressor tRNA contains a tRNA intron in the antisense codon; the expression of the suppressor tRNA is induced; the host cell is contacted with a compound; and the expression of the reporter gene and/or the activity of the protein encoded by the reporter gene is measured utilizing techniques well-known to one of skill in the art or described herein. A compound that inhibits or reduces the activity of an animalia tRNA splicing endonuclease will inhibit or reduce the production of functional suppressor tRNA and thus, reduce the expression of the reporter gene relative to a previously determined reference range, or the expression of the reporter gene in the absence of the compound or the presence of an appropriate control (e.g., a negative control). A compound that enhances the activity of an animalia tRNA splicing endonuclease will enhance the production of functional suppressor tRNA and thus, enhance the production of the reporter gene relative to a previously determined reference range, or the expression of the reporter gene in the absence of the compound or the presence of an appropriate control (e.g., a negative control).

The assays of the present invention can be performed using different incubation times. In a cell-free system, the cell-free extract or the purified tRNA splicing endonuclease and substrate for animalia tRNA splicing endonuclease can be incubated together before the addition of a compound or a member of a library of compounds. In certain embodiments, the cell-free extract or the purified animalia tRNA splicing endonuclease are incubated with a substrate for animalia tRNA splicing endonuclease before the addition of a compound or a member of a library of compounds for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day. In other embodiments, cell-free extract or purified animalia tRNA splicing endonuclease, or a substrate for animalia tRNA splicing endonuclease is incubated with a compound or a member of a library of compounds before the addition of the substrate, or the cell-free extract or the purified animalia tRNA splicing endonuclease, respectively. In certain embodiments, a compound or a member of a library of compounds is incubated with a substrate for animalia tRNA splicing endonuclease or cell-free extract or purified animalia tRNA splicing endonuclease before the addition of the remaining component, i.e., cell-free extract or purified animalia tRNA splicing endonuclease, or substrate for animalia tRNA splicing endonuclease, respectively, is at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day. Once the reaction vessel comprises the three components, i.e., a compound or a member of a library of compounds, the cell-free extract or the purified animalia tRNA splicing endonuclease, and substrate for animalia tRNA splicing endonuclease, the reaction may be further incubated for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

The progress of the reaction can be measured continuously. For example, if a substrate for animalia tRNA splicing endonuclease or subunits of animalia tRNA splicing endonuclease are labeled with fluorophore(s), the progress of the reaction can be monitored continuously using a fluorescence emission detector such as a Viewlux or Analyst. Alternatively, timepoints may be taken at different times of the reaction to monitor the progress of the reaction.

Certain assays of the present invention, such as the tRNA endonuclease suppression assay and the cell-based assays, are indirect assays for compounds that affect animalia tRNA splicing endonuclease and may detect compounds that affect another aspect of the tRNA splicing pathway. In order to confirm or ensure that a compound is a modulator of an animalia tRNA splicing endonuclease, any assay that measures the direct effect of the compound on animalia tRNA splicing endonuclease activity can be performed. Such assays include assays using purified animalia tRNA splicing endonuclease and are described below.

The compounds utilized in the assays described herein may be members of a library of compounds. In specific embodiment, the compound is selected from a combinatorial library of compounds comprising peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small organic molecule libraries. In a preferred embodiment, the small organic molecule libraries are libraries of benzodiazepines, isoprenoids, thiazolidinones, metathiazanones, pyrrolidines, morpholino compounds, or diazepindiones.

In certain embodiments, the compounds are screened in pools. Once a positive pool has been identified, the individual compounds of that pool are tested separately. In certain embodiments, the pool size is at least 2, at least 5, at least 10, at least 25, at least 50, at least 75, at least 100, at least 150, at least 200, at least 250, or at least 500 compounds.

Once a compound that modulates the activity of a tRNA splicing endonuclease is identified, the structure of the compound may be determined utilizing well-known techniques or by referring to a predetermined code. For example, the structure of the compound may be determined by mass spectroscopy, NMR, vibrational spectroscopy, or X-ray crystallography.

In certain embodiments, a compound identified in accordance with the methods of the invention may disrupt the interaction of the subunits of an animalia tRNA splicing endonuclease. In other embodiments, a compound identified in accordance with the methods of the invention may insert itself into the active site of an animalia tRNA splicing endonuclease.

A compound identified in accordance with the methods of the invention may directly bind to the tRNA splicing endonuclease. Alternatively, a compound identified in accordance with the methods of invention may bind to the intron. A compound identified in accordance with the methods of invention may also disrupt an interaction between a tRNA intron and a tRNA splicing endonuclease. Further, a compound identified in accordance with the methods of the invention may disrupt the interaction between the tRNA mature domain and the tRNA splicing endonuclease. In a preferred embodiment, a compound identified in accordance with the methods of the invention inhibits animalia tRNA splicing endonuclease activity. In another preferred embodiment, a compound identified in accordance with the methods of the invention inhibits preferentially inhibits animalia tRNA splicing endonuclease activity.

In certain embodiments of the invention, the compound identified using the assays described herein is a small molecule. In a preferred embodiment, the compound identified using the assays described herein is not known to affect the activity of an animalia tRNA splicing endonuclease. In another preferred embodiment, the compound identified using the assays described herein has not been used as or suggested to be an anti-proliferative agent or an antifungal agent.

A compound that modulates the activity of a tRNA splicing endonuclease described herein may be tested in in vitro assays or in vivo assays (e.g., cell-based assays or cell-free assays) well-known to one of skill in the art or described herein for the effect of said compound on mRNA translation. The compounds identified by the methods of the present invention can be screened for their effect on the production of mature tRNA from any of the 28 intron containing human pre-tRNAs. In vitro and in vivo assays well-known to one of skill in the art or described herein may be used to determine the antiproliferative effect of a particular compound on hyperproliferative cells versus normal cells. Further, a particular compound identified utilizing the assays described herein may be tested in an animal model for cancer to determine the efficacy of the compound in the prevention, treatment or amelioration of cancer or a symptom thereof. In addition, the effect of a compound identified utilizing the assays described herein may be tested for its effect on yeast tRNA splicing endonuclease.

The invention provides for methods for preventing, treating, managing or ameliorating a proliferative disorder or a symptom thereof, said method comprising administering to a subject in need thereof a therapeutically or prophylactically effective amount of a compound, or a pharmaceutically acceptable salt thereof, identified according to the methods described herein. In particular, the invention provides for a method of preventing, treating, managing or ameliorating cancer or a symptom thereof, said method comprising administering to a subject in need thereof an effective amount of a compound, or a pharmaceutically acceptable salt thereof, identified according to the methods described herein.

In a specific embodiment, the invention provides a method of identifying a therapeutic agent for the prevention, treatment, management or ameliorating of cancer or a symptom thereof, said method comprising: (a) contacting a member of a library of compounds with a cell containing a nucleic acid comprising a reporter gene, wherein the reporter gene comprises a tRNA intron; and (b) detecting the expression of said reporter gene, wherein if a compound that reduces the expression of said reporter gene relative to a previously determined reference range or the expression of said reporter gene in the absence of said compound or the presence of an appropriate control (e.g., a negative control such as PBS) is detected in (b), then (c) contacting the compound with a cancer cell or a neoplastic cell and detecting the proliferation of said cancer cell or neoplastic cell, so that if the compound reduces or inhibits the proliferation of the cancer cell or neoplastic cell, the compound is identified as an antiproliferative compound. In accordance with this embodiment, the compound may be administered to an animal model for cancer and the efficacy of the compound evaluated by assessing, e.g., proliferation or spread of cancer cells in the animal model.

Without being bound by theory, compounds that target the tRNA splicing endonuclease should only be toxic to highly proliferative transformed, malignant cells, while allowing for normal cellular growth and metabolism because not all tRNAs require splicing and tRNA splicing occurs more frequently in proliferating cells. There are only a handful of tRNA species that require removal of intronic sequences (Trotta, C. R. and Abelson, J. N. tRNA Splicing: An RNA World Add-On or an Ancient Reaction? In RNA World II, Tom Cech, Ray Gesteland and John Atkins (eds.), Cold Spring Harbor Laboratory Press (1999)). The current version of the sequence of the human genome has identified 648 tRNA species. Of these, only 28 contain an intron that must be removed by the tRNA splicing endonuclease. The 28 intron containing tRNAs encode 8 different isoaccepting groups. Seven of these isoaccepting groups contain redundant, non-intron-containing versions or can be decoded due to wobble rules of the codon-anticodon interaction (Bjork, G. Biosynthesis and Function of modified Nucleoside in tRNA: Structure, Biosynthesis and Function, D. Soll and V. RayBhandary (eds.), American Society for Microbiology, Washington D.C. (1995). Thus, this leaves one tRNA as a potential limiting component upon inhibition of tRNA splicing. By targeting the tRNA splicing endonuclease, an enzyme dedicated to removal of tRNA introns, the inhibition of tRNA production is fine-tuned to a very few essential tRNA molecules (potentially only a single tRNA). Thus, by inhibiting this process, a very mild toxicity, if any, to normal cells will be produced, while the ability of rapidly proliferating transformed cells to divide will be reduced or ablated as a result of the loss in translational capacity.

The invention further provides methods for verifying or confirming the ability of a compound to modulate the activity of a tRNA splicing endonuclease. The ability of a compound to modulate the activity of a tRNA splicing endonuclease can be verified or confirmed utilizing any of the assays described herein to identify such a compound. In a first embodiment, the invention provides a method for verifying the ability of a compound to inhibit animalia tRNA splicing endonuclease activity, said method comprising: (a) expressing a nucleic acid comprising a reporter gene in a cell, wherein the reporter gene comprises a tRNA intron; (b) contacting said cell with a compound; and (c) detecting the expression of said reporter gene, wherein a compound that inhibits tRNA splicing endonuclease activity is verified if the expression of said reporter gene in the presence of a compound is reduced as compared to the expression of said reporter gene in the absence of said compound or the presence of a control.

In another embodiment, the invention provides a method for verifying the ability of a compound to inhibit animalia tRNA splicing endonuclease activity, said method comprising: (a) contacting a compound with a cell-free extract and a nucleic acid comprising a reporter gene, wherein the reporter gene comprises an intron; and (b) detecting the expression of said reporter gene, wherein a compound that inhibits tRNA splicing endonuclease activity is verified if the expression of said reporter gene in the presence of a compound is reduced as compared to the expression of said reporter gene in the absence of said compound or the presence of a control. In another embodiment, the invention provides a method for verifying the ability of a compound to inhibit animalia tRNA splicing endonuclease activity, said method comprising: (a) contacting a member of a library of compounds with a cell containing a nucleic acid comprising a reporter gene, wherein the reporter gene comprises a tRNA intron; and (b) detecting the expression of said reporter gene, wherein a compound that inhibits tRNA splicing endonuclease activity is verified if the expression of said reporter gene in the presence of a compound is reduced as compared to the expression of said reporter gene in the absence of said compound or the presence of a control.

In certain embodiments, the invention provides a method for identifying a compound that modulates animalia tRNA splicing endonuclease activity, said method comprising: expressing a nucleic acid comprising a reporter gene in a cell, wherein the reporter gene comprises a tRNA intron; contacting said cell with a member of a library of compounds; and detecting the expression of said reporter gene, wherein a compound that modulates tRNA splicing endonuclease activity is identified if the expression of said reporter gene in the presence of a compound is altered relative to the expression of said reporter gene in the absence of the compound or the presence of a control.

In certain embodiments, the invention provides a method of identifying an antiproliferative compound that inhibits animalia tRNA splicing endonuclease activity, said method comprising: microinjecting a substrate of a tRNA splicing endonuclease into a animalia cell, wherein the substrate is labeled at the 5' end with a fluorophore and at the 3' end with a quencher; contacting the cell with a member of a library of compounds; and measuring the activity of the tRNA splicing endonuclease, wherein an antiproliferative compound that inhibits tRNA splicing activity is identified if a fluorescent signal is not detectable or decreased in the presence of the compound relative to the absence of the compound or the presence of a control.

In certain embodiments, the invention provides a method of identifying an antiproliferative compound that inhibits animalia tRNA splicing endonuclease activity, said method comprising: transfecting a substrate of a tRNA splicing endonuclease into an animalia cell, wherein the substrate is labeled at the 5' end with a fluorophore and at the 3' end with a quencher; contacting the cell with a member of a library of compounds; and measuring the activity of the tRNA splicing endonuclease, wherein an antiproliferative compound that inhibits tRNA splicing activity is identified if a fluorescent signal is not detectable or decreased in the presence of the compound relative to the absence of the compound or the presence of a control.

In certain embodiments, the invention provides a method of identifying an antiproliferative compound that inhibits animalia tRNA splicing endonuclease activity, said method comprising: microinjecting a substrate of a tRNA splicing endonuclease into a animalia cell, wherein said substrate is labeled at the 5' end with a fluorescent donor moiety and labeled at the 3' end with a fluorescent acceptor moiety; contacting the cell with a member of a library of compounds; and measuring the activity of the tRNA splicing endonuclease, wherein an antiproliferative compound that inhibits tRNA splicing activity is identified if the fluorescence emission of the fluorescent acceptor moiety at the wavelength of the fluorescent donor moiety in the presence of the compound is increased relative to the absence of the compound or the presence of a control.

In certain embodiments, the invention provides a method of identifying an antiproliferative compound that inhibits animalia tRNA splicing endonuclease activity, said method comprising: transfecting a substrate of a tRNA splicing endonuclease into a animalia cell, wherein said substrate is labeled at the 5' end with a fluorescent donor moiety and labeled at the 3' end with a fluorescent acceptor moiety; contacting the cell with a member of a library of compounds; and measuring the activity of the tRNA splicing endonuclease, wherein an antiproliferative compound that inhibits tRNA splicing activity is identified if the fluorescence emission of the fluorescent acceptor moiety at the wavelength of the fluorescent donor moiety in the presence of the compound is increased relative to the absence of the compound or the presence of a control.

In certain embodiments, the invention provides a method of preventing, treating, managing or ameliorating a proliferative disorder or a symptom thereof, said method comprising administering to a subject in need thereof a therapeutically or prophylactically effective amount of a compound, or a pharmaceutically acceptable salt thereof, identified according to a method of the invention.

In certain embodiments, the invention provides a method of preventing, treating, managing or ameliorating a proliferative disorder or a symptom thereof, said method comprising administering to a subject in need thereof an effective amount of a compound, or a pharmaceutically acceptable salt thereof, identified according to a method of the invention, wherein said effective amount decreases the activity of tRNA splicing endonuclease. In particular embodiment the proliferative disorder is cancer.

In certain embodiments, the invention provides a method of preventing, treating, managing or ameliorating a proliferative disorder or a symptom thereof, said method comprising administering to a subject in need thereof a therapeutically or prophylactically effective amount of an antiproliferative compound or a pharmaceutically acceptable salt thereof, identified according to a method of the invention.

In certain embodiments, the invention provides a method of preventing, treating, managing or ameliorating a proliferative disorder or a symptom thereof, said method comprising administering to a subject in need thereof an effective amount of an antiproliferative compound or a pharmaceutically acceptable salt thereof, identified according to a method of the invention, wherein said effective amount decreases the activity of tRNA splicing endonuclease. In particular embodiment the proliferative disorder is cancer.

In certain embodiments, the invention provides method for verifying the ability of a compound to inhibit animalia tRNA splicing endonuclease activity, said method comprising: expressing a nucleic acid comprising a reporter gene in a cell, wherein the reporter gene comprises a tRNA intron; contacting said cell with a compound; and detecting the expression of said reporter gene, wherein a compound that inhibits tRNA splicing endonuclease activity is verified if the expression of said reporter gene in the presence of a compound is reduced as compared to the expression of said reporter gene in the absence of said compound or the presence of a control.

In certain embodiments, the invention provides a method for verifying the ability of a compound to inhibit animalia tRNA splicing endonuclease activity, said method comprising: contacting a compound with a cell-free extract and a nucleic acid comprising a reporter gene, wherein the reporter gene comprises a tRNA intron; and detecting the expression of said reporter gene, wherein a compound that inhibits tRNA splicing endonuclease activity is verified if the expression of said reporter gene in the presence of a compound is reduced as compared to the expression of said reporter gene in the absence of said compound or the presence of a control.

In certain embodiments, the invention provides a method for verifying the ability of a compound to inhibit animalia tRNA splicing endonuclease activity, said method comprising: contacting a member of a library of compounds with a cell containing a nucleic acid comprising a reporter gene, wherein the reporter gene comprises a tRNA intron; and detecting the expression of said reporter gene, wherein a compound that inhibits tRNA splicing endonuclease activity is verified if the expression of said reporter gene in the presence of a compound is reduced as compared to the expression of said reporter gene in the absence of said compound or the presence of a control.

3.1 TERMINOLOGY

As used herein, the term "compound" refers to any agent or complex that is being tested for its ability to modulate tRNA splicing endonuclease or has been identified as modulating tRNA splicing endonuclease activity.

As used herein, the terms "disorder" and "disease" are to refer to a condition in a subject.

As used herein, the term "effective amount" refers to the amount of a compound which is sufficient to reduce or ameliorate the progression, severity and/or duration of a proliferative disorder or one or more symptoms thereof, prevent the development, recurrence or onset of a proliferative disorder or one or more symptoms thereof, prevent the advancement of a proliferative disorder or one or more symptoms thereof, or enhance or improve the therapeutic(s) effect(s) of another therapy.

As used herein, the term "fluorescent acceptor moiety" refers to a fluorescent compound that absorbs energy from a fluorescent donor moiety and re-emits the transferred energy as fluorescence. Examples of fluorescent acceptor moieties include, but are not limited to, coumarins and related fluorophores, xanthenes (e.g., fluoresceins, rhodols, and rhodamines), resorufins, cyanines, difluoroboradiazindacenes and phthalocyanines.

As used herein, the term "fluorescent donor moiety" refers to a fluorescent compound that can absorb energy and is capable of transferring the energy to an acceptor, such as another fluorescent compound. Examples of fluorescent donor moieties include, but are not limited to, coumarins and related dyes, xanthene dyes (e.g., fluoresceins, rhodols and rhodamines), resorufins, cyanine dyes, bimanes, acridines, isoindoles, dansyl dyes, aminophthalic hydrazides (e.g., luminol and isoluminol derivatives), aminophthalimides, aminonaphthalimides, aminobenzofurans, aminoquinolines, dicyanohydroquinones, fluorescent europium, terbium complexes and related compounds.

As used herein, the term "fluorophore" refers to a chromophore that fluoresces.

As used herein, the term "host cell" refers includes a particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "in combination" refers to the use of more than one therapy (e.g., prophylactic and/or therapeutic agents). The use of the term "in combination" does not restrict the order in which therapies (e.g., prophylactic and/or therapeutic agents) are administered to a subject with a proliferative disorder. A first therapy (e.g., a prophylactic or therapeutic agent such as a compound identified in accordance with the methods of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as a chemotherapeutic agent or a TNF-a antagonist) to a subject with a proliferative disorder.

As used herein, the term "library" refers to a plurality of compounds. A library can be a combinatorial library, e.g., a collection of compounds synthesized using combinatorial chemistry techniques, or a collection of unique chemicals of low molecular weight (less than 1000 daltons) that each occupy a unique three-dimensional space.

As used herein, the term "ORF" refers to the open reading frame of a mRNA, i.e., the region of the mRNA that is translated into protein.

As used herein, the terms "manage", "managing" and "management" refer to the beneficial effects that a subject derives from a therapy (e.g., a prophylactic or therapeutic agent) which does not result in a cure of the proliferative disorder. In certain embodiments, a subject is administered one or more therapies to "manage" a disease or disorder so as to prevent the progression or worsening of the disease or disorder.

As used herein, the terms "non-responsive" and refractory" describe patients treated with a currently available therapy (e.g., prophylactic or therapeutic agent) for a proliferative disorder (e.g., cancer), which is not clinically adequate to relieve one or more symptoms associated with such proliferative disorder. Typically, such patients suffer from severe, persistently active disease and require additional therapy to ameliorate the symptoms associated with their proliferative disorder.

As used herein, the phrase "pharmaceutically acceptable salt(s)," includes, but is not limited to, salts of acidic or basic groups that may be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, the terms "prevent", "preventing" and "prevention" refer to the prevention of the development, recurrence or onset of a proliferative disorder or one or more symptoms thereof resulting from the administration of one or more compounds identified in accordance the methods of the invention or the administration of a combination of such a compound and a known therapy for a proliferative disorder.

As used herein, the term "previously determined reference range" refers to a reference range for the readout of a particular assay. In a specific embodiment, the term refers to a reference range for the expression and/or the activity of a reporter gene by a particular cell or in a particular cell-free extract. Each laboratory will establish its own reference range for each particular assays, each cell type and each cell-free extract. In a preferred embodiment, at least one positive control and at least one negative control are included in each batch of compounds analyzed.

As used herein, the terms "prophylactic agent" and "prophylactic agents" refer to any agent(s) which can be used in the prevention of a proliferative disorder. In certain embodiments, the term "prophylactic agent" refers to a compound identified in the screening assays described herein. In certain other embodiments, the term "prophylactic agent" refers to an agent other than a compound identified in the screening assays described herein which is known to be useful for, or has been or is currently being used to prevent or impede the onset, development and/or progression of a proliferative disorder or one or more symptoms thereof.

As used herein, the phrase "prophylactically effective amount" refers to the amount of a therapy (e.g., a prophylactic agent) which is sufficient to result in the prevention of the development, recurrence or onset of one or more symptoms associated with a proliferative disorder.

As used herein, the term "purified," in the context of a compound, e.g., a compound identified in accordance with the method of the invention, refers to a compound that is substantially free of chemical precursors or other chemicals when chemically synthesized. In a specific embodiment, the compound is 60%, preferably 65%, 70%, 75%, 80%, 85%, 90%, or 99% free of other, different compounds. In a preferred embodiment, a compound identified in accordance with the methods of the invention is purified.

As used herein, the term "purified," in the context of a proteinaceous agent (e.g., a peptide, polypeptide, or protein, such as a tRNA splicing endonuclease or subunit thereof) refers to a proteinaceous agent which is substantially free of cellular material or contaminating proteins from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 30%, 20%, 10%, or 5% (by dry weight) of heterologous protein, polypeptide, peptide, or antibody (also referred to as a "contaminating protein"). When the proteinaceous agent is recombinantly produced, it is also preferably substantially free of culture medium, i.e., culture medium represents less than about 20%, 10%, or 5% of the volume of the protein preparation. When the proteinaceous agent is produced by chemical synthesis, it is preferably substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. Preferably, proteinaceous agents disclosed herein are isolated.

As used herein, the term "quencher" refers to a molecule or a part of a compound that is capable of reducing the emission from a fluorescent moiety. Such reduction includes reducing the light after the time when a photon is normally emitted from a fluorescent moiety.

As used herein, the term "small molecules" and analogous terms include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, organic or inorganic compounds having a molecular weight less than about 100 grams per mole, and salts, esters, and other pharmaceutically acceptable forms of such compounds. Salts, esters, and other pharmaceutically acceptable forms of such compounds are also encompassed.

As used herein, the terms "subject" and "patient" are used interchangeably herein. The terms "subject" and "subjects" refer to an animal, preferably a mammal including a non-primate (e.g., a cow, pig, horse, cat, dog, rat, and mouse) and a primate (e.g., a chimpanzee, a monkey such as a cynomolgous monkey and a human), and more preferably a human. In one embodiment, the subject is refractory or non-responsive to current therapies for a proliferative disorder. In another embodiment, the subject is a farm animal (e.g., a horse, a cow, a pig, etc.) or a pet (e.g., a dog or a cat). In a preferred embodiment, the subject is a human.

As used herein, the phrase "a substrate for an animalia tRNA splicing endonuclease" refers to any nucleotide sequence recognized and excised by an animalia tRNA splicing endonuclease. For example, a nucleotide sequence comprising a bulge-helix-bulge structure or a mature domain of a precursor tRNA may be utilized as a substrate for an animalia tRNA splicing endonuclease in an assay described herein. A nucleotide sequence recognized and excised by an animalia tRNA splicing endonuclease may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In a specific embodiment, the substrates for a tRNA splicing endonuclease utilized in the assays described herein comprise a tRNA intron. The substrate may comprise a mature domain or a bulge-helix-bulge conformation. In a preferred embodiment, the substrate comprises a mature domain of a precursor tRNA.

A substrate for an animalia tRNA endonuclease may be produced by any method well-known to one of skill in the art. For example, the substrate may be chemically synthesized using phosphoramidite or other solution or solid-phase methods. Detailed descriptions of the chemistry used to form polynucleotides by the phosphoramidite method are well known (see, e.g., Caruthers et al., U.S. Pat. Nos. 4,458,066 and 4,415,732; Caruthers et al., 1982, Genetic Engineering 4:1-17; *Users Manual Model* 392 *and* 394 *Polynucleotide Synthesizers,* 1990, pages 6-1 through 6-22, Applied Biosystems, Part No. 901237; Ojwang, et al., 1997, Biochemistry, 36:6033-6045). After synthesis, the substrate can be purified using standard techniques known to those skilled in the art (see Hwang et al., 1999, Proc. Natl. Acad. Sci. USA 96(23): 12997-13002 and references cited therein). Depending on the length of the substrate and the method of its synthesis, such purification techniques include, but are not limited to, reverse-phase high-performance liquid chromatography ("reverse-phase HPLC"), fast performance liquid chromatography ("FPLC"), and gel purification.

In a specific embodiment, the substrates depicted in FIG. 1 are utilized in the assays described herein. To generate the hybridized tRNA substrate depicted in FIG. 1, both strands of the hybridized substrate are transcribed separately and the two strands are subsequently hybridized by heating and cooling. For synthesis of the circularly permuted tRNA substrate, the RNA is transcribed from the 5' end in the intron (see FIG. 1C) to the 3' end in the intron.

As used herein, the term "synergistic" refers to a combination of a compound identified using one of the methods described herein, and another therapy (e.g., agent) which has been or is currently being used to prevent, treat, manage or ameliorate a proliferative disorder or a symptom thereof, which is more effective than the additive effects of the therapies. A synergistic effect of a combination of therapies (e.g., prophylactic or therapeutic agents) permits the use of lower dosages of one or more of the therapies and/or less frequent administration of said therapies to a subject with a proliferative disorder. The ability to utilize lower dosages of a therapy (e.g., a prophylactic or therapeutic agent) and/or to administer said therapy less frequently reduces the toxicity associated with the administration of said agent to a subject without reducing the efficacy of said therapies in the prevention, treatment, management or amelioration of a proliferative disorder. In addition, a synergistic effect can result in improved efficacy of therapies (e.g., agents) in the prevention, treatment, management or amelioration of a proliferative disorder. Finally, a synergistic effect of a combination of therapies (e.g., prophylactic or therapeutic agents) may avoid or reduce adverse or unwanted side effects associated with the use of either therapy alone.

As used herein, the terms "therapeutic agent" and "therapeutic agents" refer to any agent(s) which can be used in the prevention, treatment, management or amelioration of one or more symptoms of a proliferative disorder. In certain embodiments, the term "therapeutic agent" refers to a compound identified in the screening assays described herein. In other embodiments, the term "therapeutic agent" refers to an agent other than a compound identified in the screening assays described herein which is known to be useful for, or has been or is currently being used to prevent, treat, manage or ameliorate a proliferative disorder or one or more symptoms thereof.

As used herein, the term "therapeutically effective amount" refers to that amount of a therapy (e.g., a therapeutic agent) sufficient to result in the amelioration of one or more symptoms of a proliferative disorder, prevent advancement of a proliferative disorder, cause regression of the proliferative disorder, or to enhance or improve the therapeutic effect(s) of another therapy (e.g., therapeutic agent). In a specific embodiment, with respect to the treatment of cancer, a therapeutically effective amount refers to the amount of a therapy (e.g., a therapeutic agent) that inhibits or reduces the proliferation of cancerous cells, inhibits or reduces the spread of tumor cells (metastasis), inhibits or reduces the onset, development or progression of one or more symptoms associated with cancer, or reduces the size of a tumor. Preferably, a therapeutically effective of a therapy (e.g., a therapeutic agent) reduces the proliferation of cancerous cells or the size of a tumor by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control such as phosphate buffered saline ("PBS").

As used herein, the terms "treat", "treatment" and "treating" refer to the reduction or amelioration of the progression, severity and/or duration of a proliferative disorder or one or more symptoms thereof resulting from the administration of one or more compounds identified in accordance the methods of the invention, or a combination of one or more compounds identified in accordance with the invention and another therapy. In specific embodiments, such terms refer to the inhibition or reduction in the proliferation of cancerous cells, the inhibition or reduction the spread of tumor cells (metastasis), the inhibition or reduction in the onset, development or progression of one or more symptoms associated with cancer, or the reduction in the size of a tumor.

As used herein, the term "tRNA intron" refers to any nucleotide sequence recognized and excised by an animalia tRNA splicing endonuclease. In particular, the term "tRNA intron" refers to an intron typically found in a precursor tRNA.

As used herein, the term "tRNA splicing endonuclease" refers to the enzyme that is responsible for the recognition of the splice sites contained in precursor tRNA and the cleavage of the introns present in precursor tRNA. The archaeal tRNA splicing endonuclease recognizes the bulge-helix-bulge motif in archaeal precursor tRNA. The eukaryotic tRNA splicing endonuclease recognizes the splice sites contained in precursor tRNA by measuring the distance from the mature domain to the splice sites. The eukaryotic tRNA splicing endonuclease also has the capacity to recognize a bulge-helix-bulge motif contained in precursor tRNA. The yeast tRNA endonuclease is a heterotetramer comprising subunits having the molecular masses of 54 kDa (SEN54), 44 kDa (SEN2), 34 kDa (SEN 34), and 15 kDa (SEN 15). The human homologs of the SEN2 and SEN34 subunits have been identified and the amino acid sequences can be found in GenBank under accession numbers NP_079541 and XP_085899, respectively. In a specific embodiment, the tRNA splicing endonuclease utilized in the assays described herein is derived from or encodes an animal tRNA splicing endonuclease (preferably, a mammalian tRNA splicing endonuclease). In a preferred embodiment, the tRNA splicing endonuclease utilized in the assays described herein is a human tRNA splicing endonuclease.

As used herein, the terms "therapy" and "therapies" refer to any method, protocol and/or agent that can be used in the prevention, treatment, management or amelioration of a disease or disorder (e.g., a proliferative disorder or a fungal infection) or one or more symptoms thereof. In certain embodiments, such terms refer to chemotherapy, radiation therapy, surgery, supportive therapy and/or other therapies useful in the prevention, treatment, management or amelioration of a disease or disorder (e.g., a proliferative disorder or a fungal infection) or one or more symptoms thereof known to skilled medical personnel.

As used herein, the term "tRNA splicing endonuclease extract" refers to an extract from a cell containing tRNA splicing endonuclease activity. In certain embodiments, a tRNA splicing endonuclease extract is a cell-extract containing tRNA splicing endonuclease activity and the components necessary for the transcription and translation of a gene.

ABBREVIATION

HTS High Throughput Screen
FP fluorescence polarization
FRET Fluorescence Resonance Energy Transfer
HPLC high-performance liquid chromatography
FPLC fast performance liquid chromatography
FACS Fluorescence activated cell sorter 3.2 BRIEF DESCRIPTION OF THE DRAWINGS FIG. 1: Substrates for HTS Fluorescent screening. The endogenous tRNA is shown in panel A; the hybridized tRNA substrate is shown in panel B; and the circularly permuted tRNA substrate is shown in panel C. The 5' ss designates the 5' splice site and 3' ss designates the 3' splice site.

FIG. 2: Amino Acid Sequence Alignment of human (Hs Sen 2 (SEQ ID NO: 1) and Hs Sen 2 var. (SEQ ID NO: 2)) and yeast (Sc Sen 2p (SEQ ID NO: 3)) tRNA splicing endonuclease Sen 2 submit. The boxed amino acid residues indicate the YRGGY (SEQ ID NO: 4) active site motif, the circled amino acid residue indicates the active site histidine, and the underlined amino acid residues indicate the yeast putative transmembrane domain.

4. DETAILED DESCRIPTION OF THE INVENTION

The present invention provides methods for identifying compounds that modulate the activity of an animalia tRNA splicing endonuclease. In particular, the invention provides simple, rapid and sensitive methods for identifying compounds that inhibit the activity of a mammalian tRNA splicing endonuclease. The cell-based and cell-free assays described herein can be utilized in a high throughput format to screen libraries of compounds to identify those compounds that inhibit or reduce the activity of an animalia tRNA splicing endonuclease.

Reporter gene-based assays can be utilized to identify a compound that modulates the activity of an animalia tRNA splicing endonuclease. The reporter gene-based assays described herein may be conducted by contacting a compound with a cell genetically engineered to express a nucleic acid comprising a reporter gene, wherein said reporter gene comprises a tRNA intron, and measuring the expression of said reporter gene. Alternatively, the reporter gene-based assays may be conducted by contacting a compound with a cell-free extract and a nucleic acid comprising a reporter gene, wherein said reporter gene comprises a tRNA intron, and measuring the expression of said reporter gene. The alteration in reporter gene expression relative to a previously determined reference range, or the expression of the reporter gene in the absence of the compound or an appropriate control (e.g., a negative control) in such reporter-gene based assays indicates that a particular compound modulates an animalia tRNA splicing endonuclease activity.

FRET assays can be utilized to identify a compound that modulates the activity of an animalia tRNA splicing endonuclease. The FRET cell-based assays described herein may be conducted by microinjecting or transfecting (e.g., using liposomes or electroporation) a substrate for an animalia tRNA splicing endonuclease into a cell and contacting the cell with a compound, wherein the substrate is labeled at the 5' end with a fluorophore and labeled at the 3' end with a quencher, or, alternatively, the substrate is labeled at the 5' end with a quencher and labeled at the 3' end with a fluorophore, and measuring the fluorescence of the substrate by, e.g., fluorescence microscopy or a fluorescence emission detector such as a Viewlux or Analyst. The endogenous tRNA splicing endonuclease will cleave the substrate and result in the production of a detectable fluorescent signal. A compound that inhibits or reduces the activity of the endogenous tRNA splicing endonuclease will prevent the production of a detectable fluorescent signal. Alternatively, the FRET cell-based assays may be conducted by microinjecting or transfecting a substrate for an animalia tRNA splicing endonuclease into a cell and contacting the cell with a compound, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety, and measuring the fluorescence of the substrate by, e.g., fluorescence microscopy or a fluorescence emission detector such as a Viewlux or Analyst. The endogenous tRNA splicing endonuclease will cleave the substrate and result in the production of a detectable fluorescent signal by the fluorescent donor moiety and fluorescent acceptor moiety at the wavelength of the fluorescent donor moiety. However, a compound that inhibits the activity of the endogenous tRNA splicing endonuclease will increase the fluorescence emission of the fluorescent acceptor moiety at the wavelength of the fluorescent donor moiety.

The FRET cell-free-based assays may be conducted by contacting a substrate for an animalia tRNA splicing endonuclease with a cell-free extract or a purified animalia tRNA splicing endonuclease and a compound, wherein the substrate is labeled at the 5' end with a fluorophore and labeled at the 3' end with a quencher, or, alternatively, the substrate is labeled at the 5' end with a quencher and labeled at the 3' end with a fluorophore, and measuring the fluorescence of the substrate by, e.g., a fluorescence emission detector such as a Viewlux or Analyst. The tRNA splicing will cleave the substrate and result in the production of a detectable fluorescent signal relative to a control. A compound that enhances the activity of the tRNA splicing endonuclease will result in the increased fluorescence emission of a fluorescent acceptor moiety at the wavelength of the fluorescent donor moiety. A compound that inhibits or reduces the activity of the tRNA splicing endonuclease, however, will prevent or reduce the production of a detectable fluorescent signal relative to a control. Alternatively, the FRET cell-free-based assays may be conducted by contacting a substrate for an animalia tRNA splicing endonuclease with a cell-free extract or a purified animalia tRNA splicing endonuclease and a compound, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety, and measuring the fluorescence of the substrate by, e.g., a fluorescence emission detector such as a Viewlux or Analyst. The tRNA splicing endonuclease will cleave the substrate and result in the production of a detectable fluorescent signal by the fluorescent donor moiety and fluorescent acceptor moiety at the wavelength of the fluorescent donor moiety. A compound that inhibits or reduces the activity of the tRNA splicing endonuclease will increase the fluorescence emission of the fluorescent acceptor moiety at the wavelength of the fluorescent donor moiety. In contrast, a compound that enhances the activity of the tRNA splicing endonuclease will reduce the fluorescence emission of the fluorescent acceptor moiety at the wavelength of the fluorescent donor moiety.

A compound may be tested for its ability to enhance or inhibit the activity of an animalia tRNA endonuclease using a cell-free fluorescence polarization assay. A substrate of the animalia tRNA endonuclease is labeled on its 5' or 3' end such that cleavage by the animalia tRNA endonuclease results in a decrease of size of the labeled portion of the substrate and thus in a change of fluoresence polarization. The labeled substrate of the animalia tRNA endonuclease is incubated with a cell-free extract or a purified animalia tRNA splicing endonuclease and a compound to be tested. A compound that enhances the activity of the tRNA splicing endonuclease activity will increase the rotation of the substrate relative to a negative control or the absence of the compound, which will result in more of the light emitted being depolarized. In contrast, a compound that reduces the activity of the tRNA splicing endonuclease activity will decrease the rotation of the substrate relative to a negative control or the absence of the compound which will result in the emitted light remaining polarized.

Further a compound may be tested for its ability to enhance or inhibit the activity of an animalia tRNA endonuclease using a tRNA endonuclease suppression assay or FISH assay.

The compounds identified in assays described herein that modulate animalia tRNA splicing endonuclease activity may be tested in in vitro assays (e.g., cell-based assays or cell-free assays) or in vivo assays well-known to one of skill in the art or described herein for the effect of said compounds on tRNA processing and ultimately mRNA translation. In particular, in vitro and in vivo assays well-known to one of skill in the art or described herein may be used to determine the antiproliferative effect of a particular compound on hyperproliferative cells versus normal cells. Further, a particular compound identified utilizing the assays described herein may be tested in an animal model for cancer to determine the efficacy of the compound in the prevention, treatment or amelioration of cancer or a symptom thereof. In addition, the effect of a compound identified utilizing the assays described herein may be tested for its effect on fungal tRNA splicing endonuclease.

The structure of the compounds identified in the assays described herein that modulate animalia tRNA splicing endonuclease activity can be determined utilizing assays well-known to one of skill in the art or described herein. The methods used will depend, in part, on the nature of the library screened. For example, assays or microarrays of compounds, each having an address or identifier, may be deconvoluted, e.g., by cross-referencing the positive sample to an original compound list that was applied to the individual test assays. Alternatively, the structure of the compounds identified herein may be determined using mass spectrometry, nuclear magnetic resonance ("NMR"), X ray crystallography, or vibrational spectroscopy.

The invention encompasses the use of the compounds that inhibit or reduce the activity of an animalia tRNA splicing endonuclease which were identified in accordance with the methods described herein for the prevention, treatment, management or amelioration of a proliferative disorder or one or more symptoms thereof. In particular, the invention encompasses the use of the compounds that inhibit or reduce the activity of an animalia tRNA splicing endonuclease which were identified in accordance with the methods described herein for the prevention, treatment, management or amelioration of cancer or one or more symptoms thereof.

4.1 Reporter Gene Constructs, Transfected Cells and Cell Extracts

The invention provides for specific vectors comprising a reporter gene comprising a tRNA intron operably linked to one or more regulatory elements and host cells transfected with the vectors. The invention also provides for the in vitro translation of a reporter gene flanked by one or more regulatory elements. Techniques for practicing this specific aspect of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); Oligonucleotide Synthesis (Gait, Ed. 1984); Nucleic Acid Hybridization (Hames & Higgins, Eds. 1984); Transcription and Translation (Hames & Higgins, Eds. 1984); Animal Cell Culture (Freshney, Ed. 1986); Immobilized Cells and Enzymes (IRL Press, 1986); Perbal, A Practical Guide to Molecular Cloning (1984); Gene Transfer Vectors for Mammalian Cells (Miller & Calos, Eds. 1987, Cold Spring Harbor Laboratory); Methods in Enzymology, Volumes 154 and 155 (Wu & Grossman, and Wu, Eds., respectively), (Mayer & Walker, Eds., 1987); Immunochemical Methods in Cell and Molecular Biology (Academic Press, London, Scopes, 1987), Expression of Proteins in Mammalian Cells Using Vaccinia Viral Vectors in Current Protocols in Molecular Biology, Volume 2 (Ausubel et al., Eds., 1991).

4.1.1 Reporter Genes

Any reporter gene well-known to one of skill in the art may be used in reporter gene constructs to ascertain the effect of a compound on an animalia tRNA endonuclease. Reporter genes refer to a nucleotide sequence encoding a protein that is readily detectable either by its presence or activity. Reporter genes may be obtained and the nucleotide sequence of the elements determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g., a cDNA library, or a cDNA library generated from, or nucleic acid, preferably poly A+ RNA, isolated from, any tissue or cells expressing the reporter gene) by PCR amplification. Once the nucleotide sequence of a reporter gene is determined, the nucleotide sequence of the reporter gene may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate reporter genes having a different amino acid sequence, for example to create amino acid substitutions, deletions, and/or insertions.

Examples of reporter genes include, but are not limited to, luciferase (e.g., firefly luciferase, renilla luciferase, and click beetle luciferase), green fluorescent protein ("GFP") (e.g., green fluorescent protein, yellow fluorescent protein, red fluorescent protein, cyan fluorescent protein, and blue fluorescent protein), beta-galactosidase ("beta-gal"), beta-glucoronidase, beta-lactamase, chloramphenicol acetyltransferase ("CAT"), and alkaline phosphatase ("AP"). Table 1 below lists various reporter genes and the properties of the products of the reporter genes that can be assayed. In a preferred embodiment, a reporter gene utilized in the reporter constructs is easily assayed and has an activity which is not normally found in the cell or organism of interest.

TABLE 1

Reporter Genes and the Properties of the Reporter Gene Products

| Reporter Gene | Protein Activity & Measurement |
| --- | --- |
| CAT (chloramphenicol acetyltransferase) | Transfers radioactive acetyl groups to chloramphenicol or detection by thin layer chromatography and autoradiography |
| GAL (beta-galactosidase) | Hydrolyzes colorless galactosides to yield colored products. |
| GUS (beta-glucuronidase) | Hydrolyzes colorless glucuronides to yield colored products. |
| LUC (luciferase) | Oxidizes luciferin, emitting photons |

TABLE 1-continued

Reporter Genes and the Properties of the Reporter Gene Products

| Reporter Gene | Protein Activity & Measurement |
| --- | --- |
| GFP (green fluorescent protein) | Fluorescent protein without substrate |
| SEAP (secreted alkaline phosphatase) | Luminescence reaction with suitable substrates or with substrates that generate chromophores |
| HRP (horseradish peroxidase) | In the presence of hydrogen oxide, oxidation of 3,3',5,5'-tetramethylbenzidine to form a colored complex |
| AP (alkaline phosphatase) | Luminescence reaction with suitable substrates or with substrates that generate chromophores |

Described hereinbelow in further detailed are specific reporter genes and characteristics of those reporter genes.

4.1.1.1 Luciferase

Luciferases are enzymes that emit light in the presence of oxygen and a substrate (luciferin) and which have been used for real-time, low-light imaging of gene expression in cell cultures, individual cells, whole organisms, and transgenic organisms (reviewed by Greer & Szalay, 2002, Luminescence 17(1):43-74).

As used herein, the term "luciferase" is intended to embrace all luciferases, or recombinant enzymes derived from luciferases which have luciferase activity. The luciferase genes from fireflies have been well characterized, for example, from the *Photinus* and *Luciola* species (see, e.g., International Patent Publication No. WO 95/25798 for *Photinus pyralis*, European Patent Application No. EP 0 524 448 for *Luciola cruciata* and *Luciola lateralis*, and Devine et al., 1993, Biochim. Biophys. Acta 1173(2):121-132 for *Luciola mingrelica*). Other eucaryotic luciferase genes include, but are not limited to, the click beetle (*Photinus plagiophthalamus*, see, e.g., Wood et al., 1989, Science 244:700-702), the sea panzy (*Renilla reniformis*, see, e.g., Lorenz et al., 1991, Proc Natl Acad Sci USA 88(10):4438-4442), and the glow worm (*Lampyris noctiluca*, see e.g., Sula-Newby et al., 1996, Biochem J. 313:761-767). The click beetle is unusual in that different members of the species emit bioluminescence of different colors, which emit light at 546 nm (green), 560 nm (yellow-green), 578 nm (yellow) and 593 nm (orange) (see, e.g, U.S. Pat. Nos. 6,475,719; 6,342,379; and 6,217,847, the disclosures of which are incorporated by reference in their entireties). Bacterial luciferin-luciferase systems include, but are not limited to, the bacterial lux genes of terrestrial *Photorhabdus luminescens* (see, e.g., Manukhov et al., 2000, Genetika 36(3):322-30) and marine bacteria *Vibrio fischeri* and *Vibrio harveyi* (see, e.g., Miyamoto et al., 1988, J Biol. Chem. 263(26):13393-9, and Cohn et al., 1983, Proc Natl Acad Sci USA., 80(1):120-3, respectively). The luciferases encompassed by the present invention also includes the mutant luciferases described in U.S. Pat. No. 6,265,177 to Squirrell et al., which is hereby incorporated by reference in its entirety.

In a preferred embodiment, the luciferase is a firefly luciferase, a renilla luciferase, or a click beetle luciferase, as described in any one of the references listed supra, the disclosures of which are incorporated by reference in their entireties.

4.1.1.2 Green Fluorescent Protein

Green fluorescent protein ("GFP") is a 238 amino acid protein with amino acid residues 65 to 67 involved in the formation of the chromophore which does not require additional substrates or cofactors to fluoresce (see, e.g., Prasher et al., 1992, Gene 111:229-233; Yang et al., 1996, Nature Biotechnol. 14:1252-1256; and Cody et al., 1993, Biochemistry 32:1212-1218).

As used herein, the term "green fluorescent protein" or "GFP" is intended to embrace all GFPs (including the various forms of GFPs which exhibit colors other than green), or recombinant enzymes derived from GFPs which have GFP activity. In a preferred embodiment, GFP includes green fluorescent protein, yellow fluorescent protein, red fluorescent protein, cyan fluorescent protein, and blue fluorescent protein. The native gene for GFP was cloned from the bioluminescent jellyfish *Aequorea victoria* (see, e.g., Morin et al., 1972, J. Cell Physiol. 77:313-318). Wild type GFP has a major excitation peak at 395 nm and a minor excitation peak at 470 nm. The absorption peak at 470 nm allows the monitoring of GFP levels using standard fluorescein isothiocyanate (FITC) filter sets. Mutants of the GFP gene have been found useful to enhance expression and to modify excitation and fluorescence. For example, mutant GFPs with alanine, glycine, isoleucine, or threonine substituted for serine at position 65 result in mutant GFPs with shifts in excitation maxima and greater fluorescence than wild type protein when excited at 488 nm (see, e.g., Heim et al., 1995, Nature 373:663-664; U.S. Pat. No. 5,625,048; Delagrave et al., 1995, Biotechnology 13:151-154; Cormack et al., 1996, Gene 173:33-38; and Cramer et al., 1996, Nature Biotechnol. 14:315-319). The ability to excite GFP at 488 nm permits the use of GFP with standard fluorescence activated cell sorting ("FACS") equipment. In another embodiment, GFPs are isolated from organisms other than the jellyfish, such as, but not limited to, the sea pansy, *Renilla reriformis*.

Techniques for labeling cells with GFP in general are described in U.S. Pat. Nos. 5,491,084 and 5,804,387, which are incorporated by reference in their entireties; Chalfie et al., 1994, Science 263:802-805; Heim et al., 1994, Proc. Natl. Acad. Sci. USA 91:12501-12504; Morise et al., 1974, Biochemistry 13:2656-2662; Ward et al., 1980, Photochem. Photobiol. 31:611-615; Rizzuto et al., 1995, Curr. Biology 5:635-642; and Kaether & Gerdes, 1995, FEBS Lett 369:267-271. The expression of GFPs in *E. coli* and *C. elegans* are described in U.S. Pat. No. 6,251,384 to Tan et al., which is incorporated by reference in its entirety. The expression of GFP in plant cells is discussed in Hu & Cheng, 1995, FEBS Lett 369:331-33, and GFP expression in *Drosophila* is described in Davis et al., 1995, Dev. Biology 170:726-729.

4.1.1.3 Beta-Galactosidase

Beta galactosidase ("beta-gal") is an enzyme that catalyzes the hydrolysis of beta-galactosides, including lactose, and the galactoside analogs o-nitrophenyl-beta-D-galactopyranoside ("ONPG") and chlorophenol red-beta-D-galactopyranoside ("CPRG") (see, e.g., Nielsen et al., 1983 Proc Natl Acad Sci USA 80(17):5198-5202; Eustice et al., 1991, Biotechniques 11:739-742; and Henderson et al., 1986, Clin. Chem.

32:1637-1641). The beta-gal gene functions well as a reporter gene because the protein product is extremely stable, resistant to proteolytic degradation in cellular lysates, and easily assayed. When ONPG is used as the substrate, beta-gal activity can be quantitated with a spectrophotometer or microplate reader.

As used herein, the term "beta galactosidase" or "beta-gal" is intended to embrace all beta-gals, including lacZ gene products, or recombinant enzymes derived from beta-gals which have beta-gal activity. The beta-gal gene functions well as a reporter gene because the protein product is extremely stable, resistant to proteolytic degradation in cellular lysates, and easily assayed. In an embodiment where ONPG is the substrate, beta-gal activity can be quantitated with a spectrophotometer or microplate reader to determine the amount of ONPG converted at 420 nm. In an embodiment when CPRG is the substrate, beta-gal activity can be quantitated with a spectrophotometer or microplate reader to determine the amount of CPRG converted at 570 to 595 nm. In yet another embodiment, the beta-gal activity can be visually ascertained by plating bacterial cells transformed with a beta-gal construct onto plates containing Xgal and IPTG. Bacterial colonies that are dark blue indicate the presence of high beta-gal activity and colonies that are varying shades of blue indicate varying levels of beta-gal activity.

4.1.1.4 Beta-Glucoronidase

Beta-glucuronidase ("GUS") catalyzes the hydrolysis of a very wide variety of beta-glucuronides, and, with much lower efficiency, hydrolyzes some beta-galacturonides. GUS is very stable, will tolerate many detergents and widely varying ionic conditions, has no cofactors, nor any ionic requirements, can be assayed at any physiological pH, with an optimum between 5.0 and 7.8, and is reasonably resistant to thermal inactivation (see, e.g., U.S. Pat. No. 5,268,463, which is incorporated by reference in its entirety).

In one embodiment, the GUS is derived from the *Esherichia coli* beta-glucuronidase gene. In alternate embodiments of the invention, the beta-glucuronidase encoding nucleic acid is homologous to the *E. coli* beta-glucuronidase gene and/or may be derived from another organism or species.

GUS activity can be assayed either by fluorescence or spectrometry, or any other method described in U.S. Pat. No. 5,268,463, the disclosure of which is incorporated by reference in its entirety. For a fluorescent assay, 4-trifluoromethylumbelliferyl beta-D-glucuronide is a very sensitive substrate for GUS. The fluorescence maximum is close to 500 nm—bluish green, where very few plant compounds fluoresce or absorb. 4-trifluoromethylumbelliferyl beta-D-glucuronide also fluoresces much more strongly near neutral pH, allowing continuous assays to be performed more readily than with MUG. 4-trifluoromethylumbelliferyl beta-D-glucuronide can be used as a fluorescent indicator in vivo. The spectrophotometric assay is very straightforward and moderately sensitive (Jefferson et al., 1986, Proc. Natl. Acad. Sci. USA 86:8447-8451). A preferred substrate for spectrophotometric measurement is p-nitrophenyl beta-D-glucuronide, which when cleaved by GUS releases the chromophore p-nitrophenol. At a pH greater than its $pK_a$ (around 7.15) the ionized chromophore absorbs light at 400-420 nm, giving a yellow color.

4.1.1.5 Beta-Lactamase

Beta-lactamases are nearly optimal enzymes in respect to their almost diffusion-controlled catalysis of beta-lactam hydrolysis, making them suited to the task of an intracellular reporter enzyme (see, e.g., Christensen et al., 1990, Biochem. J. 266: 853-861). They cleave the beta-lactam ring of beta-lactam antibiotics, such as penicillins and cephalosporins, generating new charged moieties in the process (see, e.g., O'Callaghan et al., 1968, Antimicrob. Agents. Chemother. 8: 57-63 and Stratton, 1988, J. Antimicrob. Chemother. 22, Suppl. A: 23-35). A large number of beta-lactamases have been isolated and characterized, all of which would be suitable for use in accordance with the present invention (see, e.g., Richmond & Sykes, 1978, Adv. Microb. Physiol. 9:31-88 and Ambler, 1980, Phil. Trans. R. Soc. Lond. [Ser. B.] 289: 321-331, the disclosures of which are incorporated by reference in their entireties).

The coding region of an exemplary beta-lactamase employed has been described in U.S. Pat. No. 6,472,205, Kadonaga et al., 1984, J. Biol. Chem. 259: 2149-2154, and Sutcliffe, 1978, Proc. Natl. Acad. Sci. USA 75: 3737-3741, the disclosures of which are incorporated by reference in their entireties. As would be readily apparent to those skilled in the field, this and other comparable sequences for peptides having beta-lactamase activity would be equally suitable for use in accordance with the present invention. The combination of a fluorogenic substrate described in U.S. Pat. Nos. 6,472,205, 5,955,604, and 5,741,657, the disclosures of which are incorporated by reference in their entireties, and a suitable beta-lactamase can be employed in a wide variety of different assay systems, such as are described in U.S. Pat. No. 4,740,459, which is hereby incorporated by reference in its entirety.

4.1.1.6 Chloramphenicol Acetyltransferase

Chloramphenicol acetyl transferase ("CAT") is commonly used as a reporter gene in mammalian cell systems because mammalian cells do not have detectable levels of CAT activity. The assay for CAT involves incubating cellular extracts with radiolabeled chloramphenicol and appropriate co-factors, separating the starting materials from the product by, for example, thin layer chromatography ("TLC"), followed by scintillation counting (see, e.g., U.S. Pat. No. 5,726,041, which is hereby incorporated by reference in its entirety).

As used herein, the term "chloramphenicol acetyltransferase" or "CAT" is intended to embrace all CATs, or recombinant enzymes derived from CAT which have CAT activity. While it is preferable that a reporter system which does not require cell processing, radioisotopes, and chromatographic separations would be more amenable to high through-put screening, CAT as a reporter gene may be preferable in situations when stability of the reporter gene is important. For example, the CAT reporter protein has an in vivo half life of about 50 hours, which is advantageous when an accumulative versus a dynamic change type of result is desired.

4.1.1.7 Secreted Alkaline Phosphatase

The secreted alkaline phosphatase ("SEAP") enzyme is a truncated form of alkaline phosphatase, in which the cleavage of the transmembrane domain of the protein allows it to be secreted from the cells into the surrounding media. In a preferred embodiment, the alkaline phosphatase is isolated from human placenta.

As used herein, the term "secreted alkaline phosphatase" or "SEAP" is intended to embrace all SEAP or recombinant enzymes derived from SEAP which have alkaline phosphatase activity. SEAP activity can be detected by a variety of methods including, but not limited to, measurement of catalysis of a fluorescent substrate, immunoprecipitation, HPLC, and radiometric detection. The luminescent method is preferred due to its increased sensitivity over calorimetric detection methods. The advantages of using SEAP is that a cell lysis step is not required since the SEAP protein is secreted out of the cell, which facilitates the automation of sampling and assay procedures. A cell-based assay using SEAP for use in cell-based assessment of inhibitors of the Hepatitis C virus protease is described in U.S. Pat. No. 6,280,940 to Potts et al. which is hereby incorporated by reference in its entirety.

4.1.2 tRNA Introns

Any nucleotide sequence recognized and excised by an animalia tRNA splicing endonuclease may be inserted into the coding region of a reporter gene such that the mRNA coding the reporter gene out of frame utilizing well-known molecular biology techniques. For example, a nucleotide sequence comprising a bulge-helix-bulge structure or a mature domain of a precursor tRNA may be inserted into the coding region of a reporter gene such that the mRNA coding the reporter gene out of frame. Alternatively, a nucleotide sequence recognized and excised by an animalia tRNA splicing endonuclease may be inserted into the 5' untranslated region, 3' untranslated region or both the 5' and 3' untranslated regions of a reporter gene construct. A nucleotide sequence recognized and excised by an animalia tRNA splicing endonuclease may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In certain embodiments, the nucleotide sequence is at least 10 nucleotides in length.

In a specific embodiment, a tRNA intron is inserted within the open reading frame of a reporter gene. In another embodiment, two, three, four, five or more tRNA introns are inserted within the open reading frame of a reporter gene. In an alternative embodiment, a tRNA intron is inserted within the 5' untranslated region, 3' untranslated region or both the 5' and 3' untranslated region of a reporter gene construct. In an alternative embodiment, two, three, four, five or more tRNA introns are inserted within the 5' untranslated region, 3' untranslated region or both the 5' and 3' untranslated region of a reporter gene construct. The tRNA intron may comprise a bulge-helix-bulge conformation.

A reporter gene containing a tRNA intron may be produced by any method well-known to one of skill in the art. For example, the reporter gene containing a tRNA intron may be chemically synthesized using phosphoramidite or other solution or solid-phase methods. Detailed descriptions of the chemistry used to form polynucleotides by the phosphoramidite method are well known (see, e.g., Caruthers et al., U.S. Pat. Nos. 4,458,066 and 4,415,732; Caruthers et al., 1982, Genetic Engineering 4:1-17; *Users Manual Model 392 and 394 Polynucleotide Synthesizers*, 1990, pages 6-1 through 6-22, Applied Biosystems, Part No. 901237; Ojwang, et al., 1997, Biochemistry, 36:6033-6045). After synthesis, the reporter gene containing a tRNA intron can be purified using standard techniques known to those skilled in the art (see Hwang et al., 1999, Proc. Natl. Acad. Sci. USA 96(23): 12997-13002 and references cited therein). Depending on the length of the reporter gene containing a tRNA intron and the method of its synthesis, such purification techniques include, but are not limited to, reverse-phase high-performance liquid chromatography ("reverse-phase HPLC"), fast performance liquid chromatography ("FPLC"), and gel purification. Methods for labeling the substrate with a fluorescent acceptor moiety, a fluorescent donor moiety and/or quencher are well-known in the art (see, e.g., U.S. Pat. Nos. 6,472,156, 6,451, 543, 6,348,322, 6,342,379, 6,323,039, 6,297,018, 6,291,201, 6,280,981, 5,843,658, and 5,439,797, the disclosures of which are incorporated by reference in their entirety).

4.1.3 Vectors

The nucleotide sequence coding for a reporter gene and the nucleotide sequence coding for a tRNA intron can be inserted into an appropriate expression vector, i.e., a vector which contains the necessary elements for the transcription and translation of the inserted protein-coding sequence. The necessary transcriptional and translational signals can also be supplied by the reporter gene. A variety of host-vector systems may be utilized to express the reporter gene. These include, but are not limited to, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric nucleic acid consisting of appropriate transcriptional/translational control signals and the protein coding sequences. These methods may include in vitro recombinant DNA and synthetic techniques and in vivo recombinants (genetic recombination). Expression of the reporter gene construct may be regulated by a second nucleic acid sequence so that the reporter gene is expressed in a host transformed with the recombinant DNA molecule. For example, expression of a reporter gene construct may be controlled by any promoter/enhancer element known in the art, such as a constitutive promoter, a tissue-specific promoter, or an inducible promoter. Specific examples of promoters which may be used to control gene expression include, but are not limited to, the SV40 early promoter region (Bernoist & Chambon, 1981, Nature 290: 304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, a vector is used that comprises a promoter operably linked to a reporter gene, one or more origins of replication, and, optionally, one or more selectable markers (e.g., an antibiotic resistance gene). In a preferred embodiment, the vectors are CMV vectors, T7 vectors, lac vectors, pCEP4 vectors, 5.0/F vectors, or vectors with a tetracycline-regulated promoter (e.g., pcDNA™5/FRT/TO from Invitrogen Expression vectors containing the reporter gene construct of the present invention can be identified by three general approaches: (a) nucleic acid hybridization, (b) presence or absence of "marker" nucleic acid functions, (c) expression of inserted sequences, and (d) sequencing. In the first approach, the presence of the reporter gene inserted in an expression vector can be detected by nucleic acid hybridization using probes comprising sequences that are homologous to the inserted reporter gene. In the second approach, the recombinant vector/host system can be identified and selected based upon the presence or absence of certain "marker" nucleic acid functions (e.g., thymidine kinase activity, resistance to antibiotics, transformation phenotype, occlusion body formation in baculovirus, etc.) caused by the insertion of the nucleic acid of interest, i.e., the reporter gene construct, in the vector. For example, if the nucleic acid of interest is inserted within the marker nucleic acid sequence of the vector, recombinants containing the insert can be identified by the absence of the marker nucleic acid function. In the third approach, recombinant expression vectors can be identified by assaying the reporter gene product expressed by the recombinant. Such assays can be based, for example, on the physical or functional properties of the particular reporter gene.

In a preferred embodiment, the reporter gene constructs are cloned into stable cell line expression vectors. In a preferred embodiment, the stable cell line expression vector contains a site specific genomic integration site. In another preferred embodiment, the reporter gene construct is cloned into an episomal mammalian expression vector.

4.1.4 Transfection

Once a vector encoding the appropriate gene has been synthesized, a host cell is transformed or transfected with the vector of interest. The use of stable transformants is preferred. In a preferred embodiment, the host cell is a mammalian cell. In a more preferred embodiment, the host cell is a human cell. In another embodiment, the host cells are primary cells isolated from a tissue or other biological sample of interest. Host cells that can be used in the methods of the present invention include, but are not limited to, hybridomas, pre-B cells, 293 cells, 293T cells, HeLa cells, HepG2 cells, K562 cells, 3T3 cells. In another preferred embodiment, the host cells are immortalized cell lines derived from a source, e.g., a tissue. Other host cells that can be used in the present invention include, but are not limited to, virally-infected cells.

Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. Mammalian transformations (i.e., transfections) by direct uptake may be conducted using the calcium phosphate precipitation method of Graham & Van der Eb, 1978, Virol. 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei. Such methods are well-known to one of skill in the art.

In a preferred embodiment, stable cell lines containing the constructs of interest are generated for high throughput screening. Such stable cells lines may be generated by introducing a reporter gene construct comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk−, hgprt− or aprt− cells, respectively. Also, anti-metabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

4.1.5 Cell-Free Extracts

The invention provides for the translation of the reporter gene constructs in a cell-free system. Techniques for practicing this specific aspect of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); and Transcription and Translation (Hames & Higgins, Eds. 1984).

Any technique well-known to one of skill in the art may be used to generate cell-free extracts for translation in vitro. For example, the cell-free extracts for in vitro translation reactions can be generated by centrifuging cells and clarifying the supernatant. In particular, a cell extract utilized in accordance with the invention may be an S1 extract (i.e., the supernatant from a 1,000×g spin) to an S500 extract (i.e., the supernatant from a 500,000×g spin), preferably an S10 extract (i.e., the supernatant from a 10,000×g spin) to an S250 extract (i.e., the supernatant from a 250,000×g spin). In a specific embodiment, a cell extract utilized in accordance with the invention is an S50 extract (i.e., the supernatant from a 50,000×g spin) to an S100 extract (i.e., the supernatant from a 100,000×g spin).

The cell-free translation extract may be isolated from cells of any species origin. For example, the cell-free translation extract may be isolated from human cells, cultured mouse cells, cultured rat cells, Chinese hamster ovary (CHO) cells, *Xenopus* oocytes, rabbit reticulocytes, wheat germ, or rye embryo (see, e.g., Krieg & Melton, 1984, Nature 308:203 and Dignam et al., 1990 Methods Enzymol. 182:194-203). Alternatively, the cell-free translation extract, e.g., rabbit reticulocyte lysates and wheat germ extract, can be purchased from, e.g., Promega, (Madison, Wis.). In a preferred embodiment, the cell-free extract is an extract isolated from human cells. In a more preferred embodiment, the human cells are HeLa cells.

4.2 Purification of tRNA Splicing Endonuclease

Animalia tRNA splicing endonuclease or a subunit thereof, preferably mammalian, more preferably human, can be expressed and purified by any method known to the skilled artisan. Animalia tRNA splicing endonuclease can be expressed by recombinant DNA technology. In specific embodiments, the animalia tRNA splicing endonuclease is fused to a peptide tag to facilitate purification of the animalia tRNA splicing endonuclease. In other embodiments, the endogenous animalia tRNA splicing endonuclease is purified.

In certain embodiments, recombinant human tRNA splicing endonuclease is purified and used with the methods of the invention. In other embodiments, partially purified human tRNA splicing endonuclease from any human cell source is used with the methods of the invention.

4.2.1 Recombinant DNA

In various embodiments, an animalia tRNA splicing endonuclease subunit is encoded by a specific nucleotide sequence which is to be transcribed and translated. The nucleotide sequence is inserted into an expression vector for propagation and expression in recombinant cells. An animalia tRNA splicing endonuclease is a heterotetramer, each of the four subunits may be expressed together in the same cell or separately in different cells; the subunits isolated and then combined to produce tRNA splicing endonuclease. Preferably, the animalia tRNA splicing endonuclease subunits are expressed in the same cell and the functional tRNA splicing endonuclease is isolated from the cell.

An expression construct, as used herein, refers to a nucleotide sequence encoding one, two, three or four animalia tRNA splicing endonuclease subunits (preferably, human tRNA splicing endonuclease subunits) operably linked to one or more regulatory regions or enhancer/promoter sequences which enables the expression of animalia tRNA splicing endonuclease subunits in an appropriate host cell. "Operably linked" refers to an association in which the regulatory regions and the nucleotide sequence encoding an animalia tRNA splicing endonuclease subunit that is to be expressed are joined and positioned in such a way as to permit transcription, and ultimately, translation.

The regulatory regions necessary for transcription of an animalia tRNA splicing endonuclease subunit can be provided by the expression vector. In a compatible host-construct system, cellular transcriptional factors, such as RNA polymerase, will bind to the regulatory regions on the expression construct to effect transcription of an animalia tRNA splicing endonuclease subunit in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5'-non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

Constitutive, tissue-specific and/or inducible regulatory regions may be used for expression of an animalia tRNA splicing endonuclease subunit. It may be desirable to use inducible promoters when the conditions optimal for growth of the host cells and the conditions for high level expression of the animalia tRNA splicing endonuclease subunit are different. Examples of useful regulatory regions are provided below.

In order to attach DNA sequences with regulatory functions, such as promoters, to the sequence encoding an animalia tRNA splicing endonuclease subunit or to insert the sequence encoding an animalia tRNA splicing endonuclease subunit into the cloning site of a vector, linkers or adapters providing the appropriate compatible restriction sites may be ligated to the ends of the cDNAs by techniques well known in the art (Wu et al., 1987, Methods in Enzymol 152:343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising a sequence encoding an animalia tRNA splicing endonuclease subunit operably linked to regulatory regions (enhancer/promoter sequences) can be directly introduced into appropriate host cells for expression and production of an animalia tRNA splicing endonuclease subunit without further cloning. The expression constructs can also contain DNA sequences that facilitate integration of the sequence encoding an animalia tRNA splicing endonuclease subunit into the genome of the host cell, e.g., via homologous recombination. In this instance, it is not necessary to employ an expression vector comprising a replication origin suitable for appropriate host cells in order to propagate and express an animalia tRNA splicing endonuclease subunit in the host cells.

A variety of expression vectors may be used in the present invention which include, but are not limited to, plasmids, cosmids, phage, phagemids, or modified viruses. Typically, such expression vectors comprise a functional origin of replication for propagation of the vector in an appropriate host cell, one or more restriction endonuclease sites for insertion of the sequence encoding the animalia tRNA splicing endonuclease subunit, and one or more selection markers. The expression vector must be used with a compatible host cell which may be derived from a prokaryotic or an eukaryotic organism including but not limited to bacteria, yeasts, insects, mammals, and humans.

Vectors based on *E. coli* are the most popular and versatile systems for high level expression of foreign proteins (Makrides, 1996, Microbiol Rev, 60:512-538). Non-limiting examples of regulatory regions that can be used for expression in *E. coli* may include but not limited to lac, trp, lpp, phoA, recA, tac, T3, T7 and $\lambda P_L$ (Makrides, 1996, Microbiol Rev, 60:512-538). Non-limiting examples of prokaryotic expression vectors may include the λgt vector series such as λgt11 (Huynh et al., 1984 in "DNA Cloning Techniques", Vol. I: A Practical Approach (D. Glover, ed.), pp. 49-78, IRL Press, Oxford), and the pET vector series (Studier et al., 1990, Methods Enzymol., 185:60-89). However, a potential drawback of a prokaryotic host-vector system is the inability to perform many of the post-translational processing of mammalian cells. Thus, an eukaryotic host-vector system is preferred, a mammalian host-vector system is more preferred, and a human host-vector system is the most preferred.

For expression of an animalia tRNA splicing endonuclease subunit in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include but are not limited to those associated with the metallothionein II gene, mouse mammary tumor virus glucocorticoid responsive long terminal repeats (MMTV-LTR), β-interferongene, and hsp70 gene (Williams et al., 1989, Cancer Res. 49:2735-42; Taylor et al., 1990, Mol. Cell. Biol., 10:165-75). It may be advantageous to use heat shock promoters or stress promoters to drive expression of an animalia tRNA splicing endonuclease subunit in recombinant host cells.

In addition, the expression vector may contain selectable or screenable marker genes for initially isolating, identifying or tracking host cells that contain DNA encoding the elected animalia tRNA splicing endonuclease subunit. For long term, high yield production of an animalia tRNA splicing endonuclease subunit, stable expression in mammalian cells is preferred. A number of selection systems may be used for mammalian cells, including but not limited to the Herpes simplex virus thymidine kinase (Wigler et al., 1977, Cell 11:223), hypoxanthine-guanine phosphoribosyltransferase (Szybalski and Szybalski, 1962, Proc. Natl. Acad. Sci. USA 48:2026), and adenine phosphoribosyltransferase (Lowy et al., 1980, Cell 22:817) genes can be employed in tk$^-$, hgprt$^-$ or aprt$^-$ cells, respectively. Also, antimetabolite resistance can be used as the basis of selection for dihydrofolate reductase (dhfr), which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neomycin phosphotransferase (neo), which confers resistance to the aminoglycoside G-418 (Colberre-Garapin et al., 1981, J. Mol. Biol. 150:1); and hygromycin phosphotransferase (hyg), which confers resistance to hygromycin (Santerre et al., 1984, Gene 30:147). Other selectable markers, such as but not limited to histidinol and Zeocin™ can also be used.

4.2.2 Production of Recombinant Proteins 4.2.2.1 Peptide Tagging

Generating a fusion protein comprising a peptide tag and an animalia tRNA splicing endonuclease subunit can aid the purification of the animalia tRNA splicing endonuclease subunit. In a preferred embodiment, the animalia tRNA splicing endonuclease subunit is a mammalian tRNA splicing endonuclease subunit. In a more preferred embodiment, the animalia tRNA splicing endonuclease is a human animalia tRNA splicing endonuclease subunit. A fusion protein comprising a peptide and an animalia tRNA splicing endonuclease subunit can be made by ligating the nucleotide sequence encoding the animalia tRNA splicing endonuclease subunit to the sequence encoding the peptide tag in the proper reading frame. Care should be taken to ensure that the modified gene remains within the same translational reading frame, uninterrupted by translational stop signals and/or spurious messenger RNA splicing signals.

The peptide tag may be fused to the amino terminal or to the carboxyl terminal of an animalia tRNA splicing endonuclease subunit. The precise site at which the fusion is made is not critical. The optimal site can be determined by routine experimentation.

A variety of peptide tags known in the art may be conjugated to an animalia tRNA splicing endonuclease subunit including, but not limited to the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell. Bio. 4:220-229), the E. coli maltose binding protein (Guan et al., 1987, Gene 67:21-30), various cellulose binding domains (U.S. Pat. Nos. 5,496,934; 5,202,247; 5,137,819; Tomme et al., 1994, Protein Eng. 7:117-123), and the FLAG epitope (Short Protocols in Molecular Biology, 1999, Ed. Ausubel et al., John Wiley & Sons, Inc., Unit 10.11). Other peptide tags that are well-known to one of skill in the art that are recognized by specific binding partners and thus facilitate isolation by affinity binding to the binding partner (which is preferably immobilized and/or on a solid support) may be conjugated to an animalia tRNA splicing endonuclease subunit. As will be appreciated by those skilled in the art, many methods can be used to obtain the coding region of the above-mentioned peptide tags, including but not limited to, DNA cloning, DNA amplification, and synthetic methods. Some of the peptide tags and reagents for their detection and isolation are available commercially.

In a specific embodiment, the polyhistidine tag conjugated to an animalia tRNA splicing endonuclease subunit has at least 6, at least 8, at least 10 or at least 10 histidines. In a preferred embodiment, the polyhistidine tag conjugated to an animalia tRNA splicing endonuclease subunit has 8 histidines.

In another embodiment, an animalia tRNA splicing endonuclease subunit can be labeled with more than one peptide. In a specific embodiment, an animalia tRNA splicing endonuclease subunit is labeled with a peptide tag consisting of 8 histidines and a Flag epitope tag.

In certain embodiments of the invention, different subunits of an animalia tRNA splicing endonuclease can be conjugated to different peptide tags.

4.2.2.2 Expression Systems and Host Cells

Preferred mammalian host cells include but are not limited to those derived from humans, monkeys and rodents, (see, for example, Kriegler M. in "Gene Transfer and Expression: A Laboratory Manual", New York, Freeman & Co. 1990), such as monkey kidney cell line transformed by SV40 (COS-7, ATCC Accession No. CRL 1651); human embryonic kidney cell lines (293, 293-EBNA, or 293 cells subcloned for growth in suspension culture, Graham et al., J. Gen. Virol., 36:59, 1977; baby hamster kidney cells (BHK, ATCC Accession No. CCL 10); chinese hamster ovary-cells-DHFR (CHO, Urlaub and Chasin. Proc. Natl. Acad. Sci. 77; 4216, 1980); mouse sertoli cells (Mather, Biol. Reprod. 23:243-251, 1980); mouse fibroblast cells (NIH-3T3), monkey kidney cells (CV1 ATCC Accession No. CCL 70); african green monkey kidney cells (VERO-76, ATCC Accession No. CRL-1587); human cervical carcinoma cells (HELA, ATCC Accession No. CCL 2); canine kidney cells (MDCK, ATCC Accession No. CCL 34); buffalo rat liver cells (BRL 3A, ATCC Accession No. CRL 1442); human lung cells (W138, ATCC Accession No. CCL 75); human liver cells (Hep G2, HB 8065); and mouse mammary tumor cells (MMT 060562, ATCC Accession No. CCL51).

A number of viral-based expression systems may also be utilized with mammalian cells to produce an animalia tRNA splicing endonuclease subunit. Vectors using DNA virus backbones have been derived from simian virus 40 (SV40) (Hamer et al., 1979, Cell 17:725), adenovirus (Van Doren et al., 1984, Mol Cell Biol 4:1653), adeno-associated virus (McLaughlin et al., 1988, J Virol 62:1963), and bovine papillomas virus (Zinn et al., 1982, Proc Natl Acad Sci 79:4897). In cases where an adenovirus is used as an expression vector, the donor DNA sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts. (See e.g., Logan and Shenk, 1984, Proc. Natl. Acad. Sci. (USA) 81:3655-3659).

Other useful eukaryotic host-vector system may include yeast and insect systems. In yeast, a number of vectors containing constitutive or inducible promoters may be used with *Saccharomyces cerevisiae* (baker's yeast), *Schizosaccharomyces pombe* (fission yeast), *Pichia pastoris*, and *Hansenula polymorpha* (methylotropic yeasts). For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces,* 1982, Eds. Strathern et al., Cold Spring Harbor Press, Vols. I and II.

In an insect system, *Autographa californica* nuclear polyhidrosis virus (AcNPV) a baculovirus, can be used as a vector to express the human tRNA splicing endonuclease subunit in *Spodoptera frugiperda* cells. The sequences encoding an animalia tRNA splicing endonuclease subunit may be cloned into non-essential regions (for example the polyhedrin gene) of the virus and placed under control of an AcNPV promoter (for example the polyhedrin promoter). These recombinant viruses are then used to infect host cells in which the inserted DNA is expressed. (See e.g., Smith et al., 1983, J Virol 46:584; Smith, U.S. Pat. No. 4,215,051.)

Any of the cloning and expression vectors described herein may be synthesized and assembled from known DNA sequences by well known techniques in the art. The regulatory regions and enhancer elements can be of a variety of origins, both natural and synthetic. Some vectors and host cells may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

Expression constructs containing a cloned nucleotide sequence encoding an animalia tRNA splicing endonuclease subunit can be introduced into the host cell by a variety of techniques known in the art, including but not limited to, for prokaryotic cells, bacterial transformation (Hanahan, 1985, in DNA Cloning, A Practical Approach, 1:109-136), and for eukaryotic cells, calcium phosphate mediated transfection (Wigler et al., 1977, Cell 11:223-232), liposome-mediated transfection (Schaefer-Ridder et al., 1982, Science 215:166-168), electroporation (Wolff et al., 1987, Proc Natl Acad Sci 84:3344), and microinjection (Cappechi, 1980, Cell 22:479-488).

For long term, high yield production of a properly processed animalia tRNA splicing endonuclease subunit, stable expression in mammalian cells is preferred. Cell lines that stably express an animalia tRNA splicing endonuclease subunit may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while an animalia tRNA splicing endonuclease subunit is expressed continuously.

In a preferred embodiment, an animalia human tRNA splicing endonuclease subunit is transfected stably in 293T cells (ATCC Accession No. CRL-11268).

4.2.2.3 Protein Purification

Generally, an animalia tRNA splicing endonuclease subunit or the animalia tRNA splicing endonuclease can be recovered and purified from recombinant cell cultures by known methods, including ammonium sulfate precipitation, acid extraction, anion or cation exchange chromatography, phosphocellulose chromatography, immunoaffinity chromatography, hydroxyapatite chromatography, and lectin chromatography. In a preferred embodiment, the animalia tRNA splicing endonuclease subunit or animalia tRNA splicing endonuclease is a mammalian tRNA splicing endonuclease subunit or a mammalian tRNA splicing endonuclease, respectively. In a more preferred embodiment, the animalia tRNA splicing endonuclease subunit or animalia tRNA splicing endonuclease is a human tRNA splicing endonuclease subunit or a human tRNA splicing endonuclease, respectively. Before the animalia tRNA splicing endonuclease subunit can be purified, total protein has to be prepared from the cell culture. This procedure comprises collection, washing and lysis of said cells and is well known to the skilled artisan.

In particular, a recombinant animalia tRNA splicing endonuclease subunit fused to a peptide tag may be purified based on the properties of the peptide tag. One approach is based on specific molecular interactions between a tag and its binding partner. The other approach relies on the immunospecific binding of an antibody to an epitope present on the tag or on the protein which is to be purified. The principle of affinity chromatography well known in the art is generally applicable to both of these approaches. Once the animalia tRNA splicing endonuclease subunit-peptide tag fusion protein is eluted, fractions can be collected and tested for the presence of the animalia tRNA splicing endonuclease and/or for the presence of the peptide tag. In a specific embodiment, the fractions are tested for tRNA splicing endonuclease activity. Subsequently, the fractions with tRNA splicing endonuclease activity levels over a certain threshold level can be pooled.

Described below are several methods based on specific molecular interactions of a tag and its binding partner.

A method that is generally applicable to purifying an animalia tRNA splicing endonuclease subunit that are fused to the constant regions of immunoglobulin is protein A affinity chromatography, a technique that is well known in the art. *Staphylococcus* protein A is a 42 kD polypeptide that binds specifically to a region located between the second and third constant regions of heavy chain immunoglobulins. Because of the Fc domains of different classes, subclasses and species of immunoglobulins, affinity of protein A for human Fc regions is strong, but may vary among species. Subclasses that are less preferred include human IgG-3, and most rat subclasses. For certain subclasses, protein G (of Streptococci) may be used in place of protein A in the purification. Protein-A sepharose (Pharmacia or Biorad) is a commonly used solid phase for affinity purification of antibodies, and can be used essentially in the same manner for the purification of an animalia tRNA splicing endonuclease subunit fused to an immunoglobulin Fc fragment. Bound animalia tRNA splicing endonuclease subunit-Fc fusion protein can be eluted by various buffer systems known in the art, including a succession of citrate, acetate and glycine-HCl buffers which gradually lowers the pH. This method is less preferred if the recombinant cells also produce antibodies which will be co-purified with the human tRNA splicing endonuclease subunit. See, for example, Langone, 1982, J. Immunol. meth. 51:3; Wilchek et al., 1982, Biochem. Intl. 4:629; Sjobring et al., 1991, J. Biol. Chem. 26:399; page 617-618, in Antibodies A Laboratory Manual, edited by Harlow and Lane, Cold Spring Harbor laboratory, 1988.

Alternatively, a polyhistidine tag may be used, in which case, an animalia tRNA splicing endonuclease subunit can be purified by metal chelate chromatography. The polyhistidine tag, usually a sequence of six histidines, has a high affinity for divalent metal ions, such as nickel ions ($Ni^{2+}$), which can be immobilized on a solid phase, such as nitrilotriacetic acid-matrices. Polyhistidine has a well characterized affinity for $Ni^{2+}$-NTA-agarose, and can be eluted with either of two mild treatments: imidazole (0.1-0.2 M) will effectively compete with the resin for binding sites; or lowering the pH just below 6.0 will protonate the histidine sidechains and disrupt the binding. The purification method comprises loading the cell culture lysate onto the $Ni^{2+}$-NTA-agarose column, washing the contaminants through, and eluting the animalia tRNA splicing endonuclease subunit with imidazole or weak acid. $Ni^{2+}$-NTA-agarose can be obtained from commercial suppliers such as Sigma (St. Louis) and Qiagen. Antibodies that recognize the polyhistidine tag are also available which can be used to detect and quantitate the human tRNA splicing endonuclease subunit.

Another exemplary peptide tag that can be used is the glutathione-S-transferase (GST) sequence, originally cloned from the helminth, *Schistosoma japonicum*. In general, an animalia tRNA splicing endonuclease subunit-GST fusion protein expressed in a prokaryotic host cell, such as *E. coli*, can be purified from the cell culture lysate by absorption with glutathione agarose beads, followed by elution in the presence of free reduced glutathione at neutral pH. Since GST is known to form dimers under certain conditions, dimeric animalia tRNA splicing endonuclease subunit may be obtained. See, Smith, 1993, Methods Mol. Cell. Bio. 4:220-229.

Another useful peptide tag that can be used is the maltose binding protein (MBP) of *E. coli*, which is encoded by the malE gene. An animalia tRNA splicing endonuclease subunit fused to MBP binds to amylose resin while contaminants are washed away. The bound animalia tRNA splicing endonuclease subunit-MBP fusion is eluted from the amylose resin by maltose. See, for example, Guan et al., 1987, Gene 67:21-30.

The second approach for purifying an animalia tRNA splicing endonuclease subunit or animalia tRNA splicing endonuclease is applicable to peptide tags that contain an epitope for which polyclonal or monoclonal antibodies are available. It is also applicable if polyclonal or monoclonal antibodies specific to an animalia tRNA splicing endonuclease subunit or the animalia tRNA splicing endonuclease are available. Various methods known in the art for purification of protein by immunospecific binding, such as immunoaffinity chromatography, and immunoprecipitation, can be used. See, for example, Chapter 13 in Antibodies A Laboratory Manual, edited by Harlow and Lane, Cold Spring Harbor laboratory, 1988; and Chapter 8, Sections I and II, in Current Protocols in Immunology, ed. by Coligan et al., John Wiley, 1991; the disclosure of which are both incorporated by reference herein.

In particular the invention relates to the expression and purification of the human tRNA splicing endonuclease subunits Hs Sen2p and Hs Sen34p (see Table 2).

TABLE 2

| Gene | Homolog | LocusLink | Genbank Protein | Genome Contig |
|---|---|---|---|---|
| Hs Sen2p | Sc Sen2p | 80746 | NP_079541 | NT_005927.12 |
| Hs Sen34p | Sc Sen34p | 79042 | XP_085899 | NT_011225.9 |

Sc = *saccharomyces cerevisiae*
Hs = Human

Oligonucleotides complementary to the 5' and 3' ends of the open reading frames of the animalia tRNA splicing endonuclease subunits can be used to PCR amplify the open reading frames encoding the animalia tRNA splicing endonuclease.

The invention also relates to the expression and purification of an Hs Sen 2p variant ("Hs Sen 2 var."). The Hs Sen 2 var. is a splice variant of Hs Sen2 lacking exon 8 of the genomic DNA sequence for Human Sen 2. FIG. 2 depicts an amino acid sequence alignment of the amino acid sequences of the two human Sen 2 subunits (i.e., Hs Sen2 and Hs Sen 2 var.) and the amino acid sequence of the yeast subunit Sc Sen 2p. The sequence alignment reveals a high degree of similarity in the YRGGY motif (SEQ ID NO: 4), the active site for the 5' splice site of yeast (Sc Sen 2p) and archael (not shown) tRNA splicing endonuclease. Based upon the sequence alignment, the Hs Sen 2 var. lacks the putative transmembrane domain found in the Hs Sen 2 endonuclease, which may affect the localization of the Hs Sen2 var. in an animalia cell.

In specific embodiments, the Hs Sen 2 var. catalyzes the endonucleolytic cleavage of substrates other than those containing tRNA introns. In other embodiments, the Hs Sen2 var. catalyzes the endonucleolytic cleavage of substrates containing tRNA introns. In yet other embodiments, the Hs Sen2 var. catalyzes the endonucleolytic cleavage of substrates containing tRNA introns and substrates that do not contain tRNA introns.

The human subunits, including, but not limited to, Hs Sen2, Hs Sen2 var. *and* Hs Sen 34, can be utilized in accordance with the methods of the invention. In a specific embodiment, the Hs Sen 2 subunit is utilized in accordance with the methods of the invention. In another embodiment, the Hs Sen 2 var. subunit is utilized in accordance with the methods of the invention. In another embodiment, the Hs Sen 34 subunit is utilized in accordance with the methods of the invention. In yet another embodiment, Hs Sen 2, Hs Sen 2 var., Hs Sen 34 or any combination thereof is utilized in accordance with the methods of the invention.

4.2.2.4 Expression and Purification of Fungal tRNA Splicing Endonuclease

Fungal tRNA splicing endonuclease subunits (in particular, the yeast tRNA splicing endonuclease subunits) and the fungal tRNA splicing endonuclease (in particular, yeast tRNA splicing endonuclease) can be expressed and purified by any method known to the skilled artisan. A fungal tRNA splicing endonuclease subunit or the fungal tRNA splicing endonuclease can be purified by the methods discussed above for an animalia tRNA splicing endonuclease subunit or the animalia tRNA splicing endonuclease. In a specific embodiment, yeast tRNA splicing endonuclease or a subunit thereof is purified according to the procedure described in Trotta et al., 1997, Cell 89:849-858.

4.3 Compounds

Libraries screened using the methods of the present invention can comprise a variety of types of compounds. Examples of libraries that can be screened in accordance with the methods of the invention include, but are not limited to, peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (preferably, small organic molecule libraries). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as $\alpha$-amino phosphoric acids and $\alpha$-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In a preferred embodiment, the combinatorial libraries are small organic molecule libraries including, but not limited to, benzodiazepines, isoprenoids, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., ComGenex, Princeton, N.J.; Asinex, Moscow, Ru, Tripos, Inc., St. Louis, Mo.; ChemStar, Ltd, Moscow, Russia; 3D Pharmaceuticals, Exton, Pa.; Martek Biosciences, Columbia, Md.; etc.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

The combinatorial compound library for use in accordance with the methods of the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a solid support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial compound libraries of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid phase synthesize of combinatorial compound libraries, liquid phase synthesis does not require the use of specialized protocols for monitoring the individual steps of a multistep solid phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; and Stevanovic et al., 1993, Bioorg. Med. Chem. Lett. 3:431).

Combinatorial compound libraries useful for the methods of the present invention can be synthesized on solid supports. In one embodiment, a split synthesis method, a protocol of separating and mixing solid supports during the synthesis, is used to synthesize a library of compounds on solid supports (see e.g., Lam et al., 1997, Chem. Rev. 97:41-448; Ohlmeyer et al., 1993, Proc. Natl. Acad. Sci. USA 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi et al., 1997, Chem. Rev. 97:449-472).

As used herein, the term "solid support" is not limited to a specific type of solid support. Rather a large number of supports are available and are known to one skilled in the art. Solid supports include silica gels, resins, derivatized plastic films, glass beads, cotton, plastic beads, polystyrene beads, alumina gels, and polysaccharides. A suitable solid support may be selected on the basis of desired end use and suitability for various synthetic protocols. For example, for peptide synthesis, a solid support can be a resin such as p-methylbenzhydrylamine (pMBHA) resin (Peptides International, Louisville, Ky.), polystyrenes (e.g., PAM-resin obtained from Bachem Inc., Peninsula Laboratories, etc.), including chloromethylpolystyrene, hydroxymethylpolystyrene and aminomethylpolystyrene, poly (dimethylacrylamide)-grafted styrene co-divinyl-benzene (e.g., POLYHIPE resin, obtained from Aminotech, Canada), polyamide resin (obtained from Peninsula Laboratories), polystyrene resin grafted with polyethylene glycol (e.g., TENTAGEL or ARGOGEL, Bayer, Tubingen, Germany) polydimethylacrylamide resin (obtained from Milligen/Biosearch, California), or Sepharose (Pharmacia, Sweden).

In some embodiments of the present invention, compounds can be attached to solid supports via linkers. Linkers can be integral and part of the solid support, or they may be nonintegral that are either synthesized on the solid support or attached thereto after synthesis. Linkers are useful not only for providing points of compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a preferred embodiment, the compounds are cleaved from the solid support prior to high throughput screening of the compounds.

In certain embodiments of the invention, the compound is a small molecule.

4.4 In Vitro Screening Assays

Various in vitro assays can be used to identify and verify the ability of a compound to modulate the activity of an animalia tRNA splicing endonuclease. Multiple in vitro assays can be performed simultaneously or sequentially to assess the affect of a compound on the activity of an animalia tRNA splicing endonuclease. In a preferred embodiment, the in vitro assays described herein are performed in a high throughput format. In another preferred embodiment, the animalia tRNA splicing endonuclease utilized in the assays described herein is a mammalian tRNA splicing endonuclease and more preferably, a human tRNA splicing endonuclease.

4.4.1 Reporter Gene-Based Assays 4.4.1.1 Cell-Based Assays

After a vector containing the reporter gene construct is transformed or transfected into a host cell and a compound library is synthesized or purchased or both, the cells are used to screen the library to identify compounds that modulate the activity of an animalia tRNA splicing endonuclease. The reporter gene-based assays may be conducted by contacting a compound or a member of a library of compounds with a cell genetically engineered to contain a reporter gene construct comprising a reporter gene and a tRNA intron within the open reading frame of the reporter gene, or within the 5' untranslated region, 3' untranslated region or both the 5' and 3' untranslated regions of the reporter gene construct, or within a mRNA splice site of the reporter gene; and measuring the expression of said reporter gene. The alteration in reporter gene expression relative to a previously determined reference range, the absence of the compound or a control in such reporter-gene based assays indicates that a particular compound modulates the activity of an animalia tRNA splicing endonuclease. A decrease in reporter gene expression relative to a previously determined reference range, the absence of the compound or a control in such reporter-gene based assays indicates that a particular compound reduces or inhibits the activity of an animalia tRNA splicing endonuclease (e.g., the recognition or cleavage of a tRNA intron). An increase in reporter gene expression relative to a previously determined reference range, the absence of the compound or a control in such reporter-gene based assays indicates that a particular compound enhances the activity of an animalia tRNA splicing endonuclease. In a preferred embodiment, a negative control (e.g., PBS or another agent that is known to have no effect on the expression of the reporter gene) and a positive control (e.g., an agent that is known to have an effect on the expression of the reporter gene, preferably an agent that effects the activity of an animalia tRNA splicing endonuclease) are included in the cell-based assays described herein.

The step of contacting a compound or a member of a library of compounds with an animalia cell genetically engineered to contain a reporter gene construct comprising a reporter gene and a tRNA intron within the open reading frame of the reporter gene, within the 5' untranslated region, 3' untranslated region or both the 5' and 3' untranslated regions of the reporter gene construct or within a mRNA splice site may be conducted under physiologic conditions. In specific embodiment, a compound or a member of a library of compounds is added to the cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the cells and compounds used and can be determined using routine experimentation. The step of contacting a compound or a member of a library of compounds with an animalia cell genetically engineered to contain the reporter gene construct may be performed for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

In one embodiment, the invention provides a method for identifying a compound that modulates animalia tRNA splicing endonuclease activity, said method comprising: (a) expressing a nucleic acid comprising a reporter gene in a cell, wherein the reporter gene comprises a tRNA intron; (b) contacting said cell with a member of a library of compounds; and (c) detecting the expression of said reporter gene, wherein a compound that modulates tRNA splicing endonuclease activity is identified if the expression of said reporter gene in the presence of a compound is altered relative to a previously determined reference range or the expression of said reporter gene in the absence of the compound or the presence of a control. In another embodiment, the invention provides a method for identifying a compound that modulates animalia tRNA splicing endonuclease activity, said method comprising: (a) contacting a member of a library of compounds with a cell containing a nucleic acid comprising a reporter gene, wherein the reporter gene comprises a tRNA intron; and (b) detecting the expression of said reporter gene, wherein a compound that modulates tRNA splicing endonuclease activity is identified if the expression of said reporter gene in the presence of a compound is altered relative to a previously determined reference range the expression of said reporter gene in the absence of said compound or the presence of a control.

The expression of a reporter gene and/or activity of the protein encoded by the reporter gene in the cell-based reporter-gene assays may be detected by any technique well-known to one of skill in the art. The expression of a reporter gene can be readily detected, e.g., by quantifying the protein and/or RNA encoded by said gene. Many methods standard in the art can be thus employed, including, but not limited to, immunoassays to detect and/or visualize gene expression (e.g., Western blot, immunoprecipitation followed by sodium dodecyl sulfate polyacrylamide gel electrophoresis (SDS-PAGE), immunocytochemistry, etc) and/or hybridization assays to detect gene expression by detecting and/or visualizing respectively mRNA encoding a gene (e.g., Northern assays, dot blots, in situ hybridization, etc), etc. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody which recognizes the antigen to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody which recognizes the antigen) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding a primary antibody (which recognizes the antigen) conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the primary antibody) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Methods for detecting the activity of a protein encoded by a reporter gene will vary with the reporter gene used. Assays for the various reporter genes are well-known to one of skill in the art. For example, as described in Section 5.2.1., luciferase, beta-galactosidase ("beta-gal"), beta-glucoronidase ("GUS"), beta-lactamase, chloramphenicol acetyltransferase ("CAT"), and alkaline phosphatase ("AP") are enzymes that can be analyzed in the presence of a substrate and could be amenable to high throughput screening. For example, the reaction products of luciferase, beta-galactosidase ("beta-gal"), and alkaline phosphatase ("AP") are assayed by changes in light imaging (e.g., luciferase), spectrophotometric absorbance (e.g., beta-gal), or fluorescence (e.g., AP). Assays for changes in light output, absorbance, and/or fluorescence are easily adapted for high throughput screening. For example, beta-gal activity can be measured with a microplate reader. Green fluorescent protein ("GFP") activity can be measured by changes in fluorescence. For example, in the case of mutant GFPs that fluoresce at 488 nm, standard fluorescence activated cell sorting ("FACS") equipment can be used to separate cells based upon GFP activity.

Alterations in the expression of a reporter gene may be determined by comparing the level of expression of the reporter gene to a negative control (e.g., PBS or another agent that is known to have no effect on the expression of the reporter gene) and optionally, a positive control (e.g., an agent that is known to have an effect on the expression of the reporter gene, preferably an agent that effects the activity of an animalia tRNA splicing endonuclease). Alternatively, alterations in the expression of a reporter gene may be determined by comparing the level of expression of the reporter gene to a previously determined reference range.

4.4.1.2 Cell-Free Assays

After a vector containing the reporter gene construct is produced, a cell-free translation extract is generated or purchased, and a compound library is synthesized or purchased or both, the cell-free translation extract and nucleic acid are used to screen the library to identify compounds that modulate the activity of an animalia tRNA splicing endonuclease. The reporter gene-based assays may be conducted in a cell-free manner by contacting a compound with a cell-free extract and a reporter gene construct comprising a reporter gene and a tRNA intron within the open reading frame of the reporter gene or within the 5' untranslated region, 3' untranslated region or both the 5' and 3' untranslated regions of the reporter gene construct, or in a mRNA splicing site of the reporter gene, and measuring the expression of said reporter gene. The alteration in reporter gene expression relative to a previously determined reference range, the absence of the compound or a control in such reporter-gene based assays indicates that a particular compound modulates the activity of an animalia tRNA splicing endonuclease. A decrease in reporter gene expression relative to a previously determined reference range, the absence of the compound or a control in such reporter-gene based assays indicates that a particular compound reduces or inhibits the activity of an animalia tRNA splicing endonuclease (e.g., the recognition or cleavage of a tRNA intron). An increase in reporter gene expression relative to a previously determined reference range, the absence of the compound or a control in such reporter-gene based assays indicates that a particular compound enhances the activity of an animalia tRNA splicing endonuclease. In a preferred embodiment, a negative control (e.g., PBS or another agent that is known to have no effect on the expression of the reporter gene) and a positive control (e.g., an agent that is known to have an effect on the expression of the reporter gene, preferably an agent that effects the activity of an animalia tRNA splicing endonuclease) are included in the cell-free assays described herein.

In a specific embodiment, the invention provides a method for identifying a compound that modulates animalia tRNA splicing endonuclease activity, said method comprising: (a) contacting a member of a library of compounds with a cell-free extract and a nucleic acid comprising a reporter gene, wherein the reporter gene comprises a tRNA intron; and (b) detecting the expression of said reporter gene, wherein a compound that modulates tRNA splicing endonuclease activity is identified if the expression of said reporter gene in the presence of a compound is altered relative to the expression of said reporter gene in the absence of said compound or the presence of a control.

The activity of a compound in the cell-free extract can be determined by assaying the activity of a reporter protein encoded by a reporter gene, or alternatively, by quantifying the expression of the reporter gene by, for example, labeling the in vitro translated protein (e.g., with $^{35}$S-labeled methionine), northern blot analysis, RT-PCR or by immunological methods, such as western blot analysis or immunoprecipitation. Such methods are well-known to one of skill in the art.

4.4.2 FRET Assays

Fluorescence resonance energy transfer ("FRET") can be used to detect alterations in the activity of an animalia tRNA splicing endonuclease. In the FRET assays described herein, the subunits of an animalia tRNA splicing endonuclease or a substrate for an animalia tRNA splicing endonuclease may be labeled with fluorophores. In circumstances where a subunit(s) of an animalia tRNA splicing endonuclease has not been determined or isolated, the substrate for the animalia tRNA splicing endonuclease is labeled with fluorophores.

In order to obtain FRET between the fluorescent donor moiety and the fluorescent acceptor moiety or a quencher, the two moieties have to be in spatial proximity with each other. Thus, in certain embodiments, a substrate for an animalia tRNA splicing endonuclease is labeled such that the fluorescent donor moiety and the fluorescent acceptor moiety or a quencher are at most 0.5 nm, at most 1 nm, at most 5 nm, at most 10 nm, at most 20 nm, at most 30 nm, at most 40 nm, at most 50 nm or at most 100 nm apart from each other.

In certain embodiments, the substrates depicted in FIG. 1 are used in the FRET assays. In particular, the hybridized tRNA substrate and circularly permuted tRNA substrate depicted in FIGS. 1B and 1C, respectively, are used in the FRET assays. The free 5' and 3' ends of the intron of the hybridized tRNA substrate (FIG. 1B) or the free 5' and 3' ends of the intron of circularly permuted tRNA substrate (FIG. 1C) may be labeled with a fluorophore such that the close spatial proximity of the fluorophore on the 5' end with the fluorophore on the 3' end results in fluorescence resonance energy transfer. Cleavage of the substrate will then result in a spatial separation of the labeled 5' end from the labeled 3' end and thus, in reduced fluorescence resonance energy transfer. Thus, the skilled artisan can measure FRET and determine the concentration of cleaved versus uncleaved substrate. The concentration of uncleaved substrate decreases as FRET declines.

Alternatively, the 3' end or the 5' end is labeled with a fluorophore and the other end, i.e., the 5' end or the 3' end, respectively, is labeled with a quencher of the fluorophore. Upon cleavage of the intron by tRNA splicing endonuclease, the quencher and the fluorophore are separated from each other resulting in a measurable change in fluorescence. The fluorescence signal increases as the cleavage reaction proceeds.

4.4.2.1 Cell-Based Assays with a Labeled Substrate

The FRET cell-based assays may be conducted by microinjecting or transfecting (e.g., using liposomes or electroporation) a substrate for an animalia tRNA splicing endonuclease into a cell and contacting the cell with a compound, wherein the substrate is labeled at the 5' end with a fluorophore and labeled at the 3' end with a quencher, or alternatively, the substrate is labeled at the 5' end with a quencher and labeled at the 3' end with a fluorophore, and measuring the fluorescence of the substrate by, e.g., fluorescence microscopy or a fluorescence emission detector such as a Viewlux or Analyst. The endogenous tRNA splicing endonuclease will cleave the substrate and result in the production of a detectable fluorescent signal. A compound that inhibits or reduces the activity of the endogenous tRNA splicing endonuclease will inhibit or reduce the cleavage of the substrate and thus, inhibit or reduce the production of a detectable fluorescent signal relative to a negative control (e.g., PBS). A compound that enhances the activity of the endogenous endonuclease will enhance the cleavage of the substrate and thus, increase the production of a detectable fluorescent signal relative to a negative control (e.g., PBS).

Alternatively, the FRET cell-based assays may be conducted by microinjecting or transfecting a substrate for an animalia tRNA splicing endonuclease into a cell and contacting the cell with a compound, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety, and measuring the fluorescence of the substrate by, e.g., fluorescence microscopy or a fluorescence emission detector such as a Viewlux or Analyst. The endogenous tRNA splicing endonuclease will cleave the substrate and result in the production of a detectable fluorescent signal by the fluorescent donor moiety and fluorescent acceptor moiety at the wavelength of the fluorescent donor moiety. A compound that inhibits or reduces the activity of the endogenous tRNA splicing endonuclease will inhibit or reduce cleavage of the substrate and thus, increase the fluorescence emission of the fluorescent acceptor moiety at the wavelength of the fluorescent donor moiety relative to a negative control (e.g., PBS). A compound that enhances the activity of the endogenous tRNA splicing endonuclease will enhance the cleavage of the substrate and thus, reduce the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET cell-based assays described herein.

Optionally, an agent that inhibits or reduces the activity of the animalia tRNA splicing ligase such as an antibody that specifically binds to the ligase may be used in the contacting step to determine, ensure or confirm that a compound is not solely functioning by inhibiting or reducing the activity of the ligase. Alternatively, the FRET cell-based assay may be conducted in cells deficient in tRNA splicing ligase. As another alternative, ATP may be excluded from the assay. Without being bound by theory, since ATP is required for the tRNA splicing ligase reaction, any effect a compound has in the assay should be attributable to an effect of the compound on the endonuclease.

The assay can be conducted in any buffer system that provides conditions conducive to the tRNA endonuclease reaction. Such buffer systems are well known to the skilled artisan. In a specific embodiment, the buffer is the medium in which the cell culture is kept. Care should be taken that Magnesium ions are present in the medium.

In certain embodiments, the assay is conducted for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

In a specific embodiment, the invention provides a method of identifying an antiproliferative compound that inhibits or reduces animalia tRNA splicing endonuclease activity, said method comprising: (a) microinjecting or transfecting a substrate of a tRNA splicing endonuclease into a animalia cell, wherein the substrate is labeled at the 5' end with a fluorophore and labeled at the 3' end with a quencher, or alternatively, the substrate is labeled at the 5' end with a quencher and labeled at the 3' end with a fluorophore; (b) contacting the cell with a member of a library of compounds; and (c) measuring the activity of the tRNA splicing endonuclease, wherein an antiproliferative compound that inhibits or reduces tRNA splicing activity is identified if a fluorescent signal is not detectable in the presence of the compound relative to the absence of the compound or the presence of a control. In another embodiment, the invention provides a method of identifying an antiproliferative compound that inhibits or reduces animalia tRNA splicing endonuclease activity, said method comprising: (a) contacting an animalia cell containing a substrate of a tRNA splicing endonuclease with a member of a library of compounds, wherein the substrate is labeled at the 5' end with a fluorophore and at the 3' end with a quencher, or alternatively, the substrate is labeled at the 5' end with a quencher and labeled at the 3' end with a fluorophore; and (b) measuring the activity of the tRNA splicing endonuclease, wherein an antiproliferative compound that inhibits or reduces tRNA splicing activity is identified if a fluorescent signal is not detectable in the presence of the compound relative to the absence of the compound or the presence of a control.

In another embodiment, the invention provides a method of identifying an antiproliferative compound that inhibits or reduces animalia tRNA splicing endonuclease activity, said method comprising: (a) microinjecting or transfecting a substrate of a tRNA splicing endonuclease into a animalia cell, wherein the substrate is labeled at the 5' end with a fluorescent donor moiety and labeled at the 3' end with a fluorescent acceptor moiety, or alternatively, the substrate is labeled at the 5' end with a fluorescent acceptor moiety and labeled at the 3' end with a fluorescent donor moiety; (b) contacting the cell with a member of a library of compounds; and (c) measuring the activity of the tRNA splicing endonuclease, wherein an antiproliferative compound that inhibits or reduces tRNA splicing activity is identified if the fluorescent signal detected in the presence of the compound is altered relative to the absence of the compound or the presence of a control. In another embodiment, the invention provides a method of identifying an antiproliferative compound that inhibits or reduces animalia tRNA splicing endonuclease activity, said method comprising: (a) contacting an animalia cell containing substrate of a tRNA splicing endonuclease with a member of a library of compounds, wherein the substrate is labeled at the 5' end with a fluorescent donor moiety and labeled at the 3' end with a fluorescent acceptor moiety, or alternatively, the substrate is labeled at the 5' end with a fluorescent acceptor moiety and labeled at the 3' end with a fluorescent donor moiety; and (b) measuring the activity of the tRNA splicing endonuclease, wherein an antiproliferative compound that inhibits or reduces tRNA splicing endonuclease activity is identified if the fluorescence emission of the fluorescent acceptor moiety at the wavelength of the fluorescent donor moiety in the presence of the compound is increased relative to the absence of the compound or the presence of a control.

Any nucleotide sequence recognized and excised by an animalia tRNA splicing endonuclease may be utilized as a substrate for an animalia tRNA splicing endonuclease in a FRET assay described herein. For example, a nucleotide sequence comprising a bulge-helix-bulge structure or a mature domain of a precursor tRNA may be utilized as a substrate for an animalia tRNA splicing endonuclease in a FRET assay described herein. A nucleotide sequence recognized and excised by an animalia tRNA splicing endonuclease may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In a specific embodiment, the substrates for a tRNA splicing endonuclease utilized in the FRET assays described herein comprise a tRNA intron. The substrate may comprise a bulge-helix-bulge conformation. In a preferred embodiment, the substrate comprises a tRNA mature domain that contains an intron.

In accordance with the invention, a single pair of fluorescent donor and acceptor moieties. The substrate can be labeled with different pairs of fluorescent donor moieties and fluorescent acceptor moieties. For example, two, three, four, five or more pairs of fluorescent donor moieties and fluorescent acceptor moieties can be used. In this situation, preferably, at least one of the pairs comprise a fluorescent acceptor moiety that has a different emission spectrum from the fluorescent acceptor moiety of at least one of the other pairs. Alternatively, when at least three pairs are used, the fluorescent acceptor moiety of the first pair, second pair and third pair has a different emission spectrum than the fluorescent acceptor moiety of the other two. Methods for labeling the substrate with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety). The labeled substrate can be microinjected or transfected into animalia cells (preferably, mammalian cells and more preferably, human cells) utilizing techniques well-known to one of skill in the art (see, e.g., Adams et al., 1991, Nature 349:694-697).

The activity of a compound on an animalia tRNA splicing endonuclease in the FRET cell-based assays can be determined by measuring the fluorescent emission spectra of the substrate utilizing techniques well-known to one of skill in the art. The fluorescent emission spectra measured depends, in part, on the fluorophore used.

4.4.2.2 Cell-Free Assays with a Labeled Substrate

The FRET cell-free assays may be conducted by contacting a substrate for an animalia tRNA splicing endonuclease with a cell-free extract (see Section 4.4.1.2 supra regarding cell-free extracts, preferably, a tRNA splicing endonuclease extract) or a purified animalia tRNA splicing endonuclease and a compound, wherein the substrate is labeled at the 5' end with a fluorophore and labeled at the 3' end with a quencher or, alternatively, the substrate is labeled at the 3' end with a fluorophore and labeled at the 5' end with a quencher, and measuring the fluorescence of the substrate in, e.g., a fluorescence emission detector such as a Viewlux or Analyst. The tRNA splicing endonuclease in the cell-free extract will cleave the substrate and result in the production of a detectable fluorescent signal. A compound that inhibits or reduces the activity of the tRNA splicing endonuclease will inhibit or reduce the cleavage of the substrate and thus, inhibit or reduce the production of a detectable fluorescent signal relative to a negative control (e.g., PBS). A compound that enhances the activity of the tRNA splicing endonuclease will enhance the cleavage of the substrate and thus, increase the production of a detectable signal relative to a negative control (e.g., PBS).

Alternatively, the FRET cell-free-based assays may be conducted by contacting a substrate for an animalia tRNA splicing endonuclease with a cell-free extract (preferably, a tRNA splicing endonuclease extract) or a purified animalia tRNA splicing endonuclease and a compound, wherein the substrate is labeled at the 5' end with a fluorescent donor moiety and labeled at the 3' end with a fluorescent acceptor moiety, or alternatively, the substrate is labeled at the 5' end with a fluorescent acceptor moiety and labeled at the 3' end with a fluorescent donor moiety, and measuring the fluorescence of the substrate by, e.g., a fluorescence emission detector such as a Viewlux or Analyst. The tRNA splicing endonuclease will cleave the substrate and result in the production of a detectable fluorescent signal by the fluorescent donor moiety and fluorescent acceptor moiety at the wavelength of the fluorescent donor moiety. A compound that inhibits or reduces the activity of the tRNA splicing endonuclease will inhibit or reduce cleavage of the substrate and thus, increase the fluorescence emission of the fluorescent acceptor moiety at the wavelength of the fluorescent donor moiety relative to a negative control (e.g., PBS). A compound that enhances the activity of the tRNA splicing endonuclease will enhance the cleavage of the substrate and thus, reduce the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET cell-free assays described herein.

The assay can be conducted in any buffer system that provides conditions conducive to the tRNA endonuclease reaction. Such buffer systems are well known to the skilled artisan. In a specific embodiment, the buffer comprises 20 mM Tris at a pH of 7.0, 50 mM KCl, 0.1 mM DTT, 5 mM $MgCl_2$, and 0.4% Triton X100. Care should be taken that pH, salt concentration, detergent concentration etc. of the buffer system do not interfere with FRET.

In certain embodiments, the assay is conducted for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

In one embodiment, the invention provides a method of identifying an antiproliferative compound that inhibits or reduces animalia tRNA splicing endonuclease activity, said method comprising: (a) contacting an animalia cell-free extract (preferably, a tRNA splicing endonuclease extract) or a purified animalia tRNA splicing endonuclease with a substrate of a tRNA splicing endonuclease and a member of a library of compounds, wherein the substrate is labeled at the 5' end with a fluorophore and labeled at the 3' end with a quencher, or alternatively, the substrate is labeled at the 5' end with a quencher and labeled at the 3' end with a fluorophore; and (b) measuring the activity of the tRNA splicing endonuclease, wherein an antiproliferative compound that inhibits or reduces tRNA splicing activity is identified if a fluorescent signal is not detectable in the presence of the compound relative to the absence of the compound or the presence of a control. In another embodiment, the invention provides a method of identifying an antiproliferative compound that inhibits or reduces animalia tRNA splicing endonuclease activity, said method comprising: (a) contacting an animalia cell-free extract (preferably, a tRNA splicing endonuclease extract) or a purified animalia tRNA splicing endonuclease with a substrate of a tRNA splicing endonuclease and a member of a library of compounds, wherein said substrate is labeled at the 5' end with a fluorescent donor moiety and labeled at the 3' end with a fluorescent acceptor moiety, or alternatively, the substrate is labeled at the 5' end with a fluorescent acceptor moiety and labeled at the 3' end with a fluorescent donor moiety; and (b) measuring the activity of the tRNA splicing endonuclease, wherein an antiproliferative compound that inhibits tRNA splicing activity is identified if the fluorescence emission of the fluorescent acceptor moiety at the wavelength of the fluorescent donor moiety detected in the presence of the compound is increased relative to the absence of the compound or the presence of a control.

In accordance with the invention, the substrate can be labeled with a single pair of fluorescent donor and acceptor moieties. The substrate can be labeled with different pairs of fluorescent donor moieties and fluorescent acceptor moieties. For example, two, three, four, five or more pairs of fluorescent donor moieties and fluorescent acceptor moieties can be used. In this situation, preferably, at least one of the pairs comprise a fluorescent acceptor moiety that has a different emission spectrum from the fluorescent acceptor moiety of at least one of the other pairs. Alternatively, when at least three pairs are used, the fluorescent acceptor moiety of the first pair, second pair and third pair has a different emission spectrum than the fluorescent acceptor moiety of the other two. Methods for labeling the substrate with a fluorescent acceptor moiety, a fluorescent donor moiety and/or quencher are well-known in the art (see, e.g., U.S. Pat. Nos. 6,472,156, 6,451,543, 6,348, 322, 6,342,379, 6,323,039, 6,297,018, 6,291,201, 6,280,981, 5,843,658, and 5,439,797, the disclosures of which are incorporated by reference in their entirety).

The activity of a compound on an animalia tRNA splicing endonuclease in the FRET cell-free assays can be determined by measuring the fluorescent emission spectra of the substrate utilizing techniques well-known to one of skill in the art. The fluorescent emission spectra measured depends, in part, on the fluorophore used.

4.4.2.3 Cell-Based Assays with Labeled Enzyme

A FRET cell-based assay may be conducted by microinjecting or transfecting a first subunit of an animalia tRNA splicing endonuclease (e.g., SEN2) labeled with a fluorophore and a second, different subunit of an animalia tRNA splicing endonuclease (e.g., SEN34) labeled with a quencher into a cell and contacting the cell with a compound, and measuring the fluorescence of the animalia tRNA splicing endonuclease by, e.g., fluorescence microscopy or a fluorescence emission detector such as a Viewlux or Analyst. Preferably, the cell microinjected or transfected is deficient in one or more of the subunits of the animalia tRNA splicing endonuclease. Any methods known to the skilled artisan can be used to remove the expression and/or function of one or more subunits of the animalia tRNA splicing endonuclease from the cell. In a specific embodiment, RNAi is used to transiently remove one or more of the subunits of the animalia tRNA splicing endonuclease. The formation of the animalia tRNA splicing endonuclease from the labeled subunits will result in a reduction in the fluorescence detectable. A compound that inhibits or reduces the formation of the animalia tRNA splicing endonuclease will reduce or inhibit the production of a detectable fluorescent signal relative to a negative control (e.g., PBS). A compound that enhances the formation of the animalia tRNA splicing endonuclease will increase the fluorescence detectable relative to a negative control (e.g., PBS).

Alternatively, a FRET cell-based assay may be conducted by microinjecting a first subunit of an animalia tRNA splicing endonuclease (e.g., SEN2) labeled with a fluorescent donor moiety and a second, different subunit of an animalia tRNA splicing endonuclease (e.g., SEN34) labeled with a fluorescent acceptor moiety into a cell and contacting the cell with a compound, and measuring the fluorescence of the animalia tRNA splicing endonuclease by, e.g., fluorescence microscopy or a fluorescence emission detector such as a Viewlux or Analyst. The formation of the animalia tRNA splicing endonuclease will result in the production of a detectable fluorescent signal by the fluorescent donor moiety and fluorescent acceptor moiety at the wavelength of the fluorescent donor moiety. A compound that inhibits or reduces the formation of the animalia tRNA splicing endonuclease will reduce the fluorescence emission of the fluorescent acceptor moiety at the wavelength of the fluorescent donor moiety relative to a negative control (e.g., PBS). A compound that enhances the formation of the animalia tRNA splicing endonuclease will increase the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET cell-based assays described herein.

In certain embodiments, the compound and the cell are incubated for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

Methods for labeling a subunit of an animalia tRNA splicing endonuclease with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety).

4.4.2.4 Cell-Free Assays with Labeled Enzyme

A FRET cell-free assay may be conducted by contacting a first subunit of an animalia tRNA splicing endonuclease (e.g., SEN2) labeled with a fluorophore and a second subunit of an animalia tRNA splicing endonuclease (e.g., SEN34) labeled with a quencher with a compound in vitro under conditions conducive to the formation of the endonuclease, and measuring the fluorescence of the animalia tRNA splicing endonuclease by, e.g., a fluorescence emission detector such as a Viewlux or Analyst. The formation of the animalia tRNA splicing endonuclease from the labeled subunits will result in a reduction in the fluorescence detectable. A compound that inhibits or reduces the formation of the animalia tRNA splicing endonuclease will enhance the production of detectable fluorescent signal relative to the absence of the compound or the presence of a negative control (e.g., PBS). A compound that enhances the formation of the animalia tRNA splicing endonuclease will reduce or inhibit the fluorescence detectable relative to the absence of the compound or a negative control (e.g., PBS).

Alternatively, a FRET cell-free assay may be conducted by contacting a first subunit of an animalia tRNA splicing endonuclease (e.g., SEN2) labeled with a fluorescent donor moiety and a second, different subunit of an animalia tRNA splicing endonuclease (e.g., SEN34) labeled with a fluorescent acceptor moiety with a compound in vitro under conditions conducive to the formation of the endonuclease, and measuring the fluorescence of the animalia tRNA splicing endonuclease by, e.g., a fluorescence emission detector such as a Viewlux or Analyst. The formation of the animalia tRNA splicing endonuclease will result in the production of a detectable fluorescent signal by the fluorescent donor moiety and fluorescent acceptor moiety at the wavelength of the fluorescent donor. A compound that inhibits or reduces the formation of the animalia tRNA splicing endonuclease will reduce the fluorescence emission of the fluorescent acceptor moiety at the wavelength of the fluorescent donor moiety relative to the absence of the compound or the presence of a negative control (e.g., PBS). A compound that enhances the formation of the animalia tRNA splicing endonuclease will increase the fluorescence emission of the fluorescent acceptor moiety at the wavelength of the fluorescent donor moiety relative to the absence of the compound or the presence of a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET cell-free assays described herein.

4.4.3 Direct Binding Assays

Compounds that modulate the activity of an animalia tRNA splicing endonuclease can be identified by direct binding assays. In particular, compounds that inhibit the activity of an animalia tRNA splicing endonuclease by directly or indirectly reducing or inhibiting the interaction between a substrate for an animalia tRNA splicing endonuclease and an animalia tRNA splicing endonuclease. Such assays are described in International Patent Publication Nos. WO 02/083837 and WO 02/083953, the disclosures of which are hereby incorporated by reference in their entireties. Briefly, direct binding assays may be conducted by attaching a library of compounds to solid supports, e.g., polymer beads, with each solid support having substantially one type of compound attached to its surface. The plurality of solid supports of the library is exposed in aqueous solution to a substrate for an animalia tRNA splicing endonuclease having a detectable label, forming a dye-labeled substrate:support-attached compound complex. Binding of a substrate to a particular compound labels the solid support, e.g., bead, comprising the compound, which can be physically separated from other, unlabeled solid supports. Once labeled solid supports are identified, the chemical structures of the compounds thereon can be determined by, e.g., reading a code on the solid support that correlates with the structure of the attached compound.

Alternatively, direct binding assays may be conducted by contacting a substrate for an animalia tRNA splicing endonuclease having a detectable label with a member of a library of compounds free in solution, in labeled tubes or microtiter wells, or a microarray. Compounds in the library that bind to the labeled substrate of an animalia tRNA splicing endonuclease will form a detectably labeled complex that can be identified and removed from the uncomplexed, unlabeled compounds in the library, and from uncomplexed, labeled substrate of an animalia tRNA splicing endonuclease, by a variety of methods including, but not limited to, methods that differentiate changes in the electrophoretic, chromatographic, or thermostable properties of the complexed substrate.

4.4.4 Fluorescence Polarization Assay

The effect of a compound on the activity of an animalia tRNA splicing endonuclease may be determined utilizing a fluorescence polarization-based assay. In such an assay, a fluorescently labeled substrate for an animalia tRNA splicing endonuclease is contacted with an animalia cell-free extract (preferably, an animalia tRNA splicing endonuclease extract) or a purified animalia tRNA splicing endonuclease and a compound or a member of a library of compounds; and the fluorescently polarized light emitted is measured. An important aspect of this assay is that the size of the substrate used in the assay is large enough to distinguish a change in fluorescent polarized light emitted following cleavage of the substrate. The tRNA splicing endonuclease in the cell-free extract or the purified animalia tRNA splicing endonuclease will cleave the substrate and result in a change in intensity of emitted polarized light. Fluorescently labeled substrates when excited with plane polarized light will emit light in a fixed plane only if they do not rotate during the period between excitation and emission. The extent of depolarization of the emitted light depends upon the amount of rotation of the substrate, which is dependent on the size of the substrate. Small substrates rotate more than larger substrates between the time they are excited and the time they emit fluorescent light. A small fluorescently labeled substrate rotates rapidly and the emitted light is depolarized. A large fluorescently labeled substrate rotates more slowly and results in the emitted light remaining polarized. A compound that inhibits the activity of the tRNA splicing endonuclease will inhibit or reduce the cleavage of the substrate and thus, decrease the rotation of the substrate relative to a negative control (e.g., PBS) or the absence of the compound, which will result in the emitted light remaining polarized. A compound that enhances the activity of the tRNA splicing endonuclease will enhance the cleavage of the substrate and thus, increase the rotation of the substrate relative to a negative control (e.g., PBS) or the absence of the compound, which will result in more of the emitted light being depolarized.

The intensities of the light are measured in planes 90° apart and are many times designated the horizontal and vertical intensities. In some instruments the excitation filter is moveable while the emission filter is fixed. In certain other machines the horizontal and vertical intensities are measured simultaneously via fiber optics. Research grade fluorescence polarization instruments are commercially available from, e.g., PanVera, BMG Lab Technologies, and LJL Biosystems. Abott provides clinical laboratory instrumentation. The value of fluorescence polarization is determined by the following equation:

$$\text{polarization} = \frac{\text{intensity}_{vertical} - \text{intensity}_{horizontal}}{\text{intensity}_{veritcal} + \text{intensity}_{horizontal}}.$$

Fluorescence polarization values are most often divided by 1000 and expressed as millipolarization units (mP).

In a specific embodiment, the hybridized tRNA or circularly permuted tRNA depicted in FIG. 1 are used as a substrate for the endonuclease. In accordance with this embodiment, the 5' end in the intron of the hybridized tRNA or the circularly permuted tRNA, or the 3' end in the intron of the hybridized tRNA or the circularly permuted tRNA or both are labeled with a fluorophore. Upon cleavage, the size of the molecule to which the fluorophore is attached changes because the intron is released from the substrate. The decrease in molecular weight of the labeled molecule results in an increase of depolarization of light that is emitted from the fluorophore. Measuring the amount of depolarization allows the skilled artisan to determine the amount of cleaved substrate.

4.4.5 tRNA Endonuclease Suppression Assay

The effect of a compound or a member of a library of compounds on the activity of an animalia tRNA splicing endonuclease may be determined using a tRNA endonuclease suppression assay. In such an assay, a host cell is engineered to contain a first reporter gene construct and a suppressor tRNA; the expression of the suppressor tRNA is induced; the host cell is contacted with a compound or a member of a library of compounds; and the expression of the reporter gene and/or the activity of the protein encoded by the reporter gene is measured. The first reporter gene construct comprises a reporter gene with a nonsense codon in its open reading frame such that the open reading frame is interrupted. Standard mutagenesis techniques described, e.g., in Sambrook (Sambrook, 1989, Molecular Cloning, A Laboratory Manual, Second Edition; DNA Cloning, Volumes I and II (Glover, Ed. 1985)) may be used to introduce a nonsense codon into the open reading frame of any reporter gene well-known to one of skill in the art. The first reporter gene construct is transfected into a host cell engineered to contain a suppressor tRNA. Alternatively, the first reporter gene is cotransfected into a host cell with a suppressor tRNA. The suppressor tRNA's expression is regulated by a controllable regulatory element; such as by a tetracycline regulated regulatory element (see, e.g., Buvoli et al, 2000, Molecular and Cellular Biology 20:3116-3124; Park and Bhandary, 1998, Molecular and Cellular Biology 18:4418-4425) and the suppressor tRNA contains a tRNA intron in the anticodon stem such that only properly spliced suppressor tRNA is functional. Expression of functional suppressor tRNA is dependent on (i) the transcription of the suppressor tRNA, and (ii) tRNA splicing. The expression of functional suppressor tRNA suppresses the nonsense codon in the reporter gene and results in full length, functional reporter gene expression. Accordingly, the expression of full length, functional reporter gene correlates with the expression of functional suppressor tRNA, which in turn correlates with the level of transcription of the suppressor tRNA and tRNA splicing. The expression of full-length reporter gene and the activity of the protein encoded by the reporter gene can be assayed by any method well known to the skilled artisan or as described herein.

A compound that inhibits or reduces the activity of an animalia tRNA splicing endonuclease will inhibit or reduce the production of functional suppressor tRNA and thus, reduce the expression of the reporter gene relative to a previously determined reference range or a control. A compound that enhances the activity of an animalia tRNA splicing endonuclease will enhance the production of functional suppressor tRNA and thus, enhance the production of the reporter gene relative to a previously determined reference range or a control.

The step of inducing the expression of the suppressor tRNA may be conducted simultaneously with the step of contacting the host cell with a compound or at least 5 minutes, at least 15 minutes, at least 0.5 hours, at least 1 hour, at least 1.5 hours, at least 2 hours, at least 3 hours, at least 4 hours, at least 5 hours, at least 6 hours, at least 8 hours, at least 10 hours or at least 12 hours before the step of contacting the compound with the host cell. In certain embodiments, the expression of the suppressor tRNA is induced by incubating the host cell with an agent such as, e.g., tetracycline, for approximately 5 minutes, approximately 15 minutes, approximately 0.5 hours, approximately 1 hour, approximately 1.5 hours, approximately 2 hours, approximately 3 hours, approximately 4 hours, approximately 5 hours, 6 approximately hours, 8 approximately hours, approximately 10 hours or approximately 12 hours. In other embodiments, the host cell is contacted with the compound for approximately 5 minutes, approximately 15 minutes, approximately 0.5 hours, approximately 1 hour, approximately 1.5 hours, approximately 2 hours, approximately 3 hours, approximately 4 hours, approximately 5 hours, 6 approximately hours, 8 approximately hours, approximately 10 hours or approximately 12 hours.

Optionally, the host cell is engineered to contain a second reporter gene construct comprising a reporter gene different from the first reporter gene that does not contain a nonsense codon. In a specific embodiment, the reporter genes used in the tRNA endonuclease suppression assay are Red and Green Click Beetle luciferase, wherein the Red luciferase contains the nonsense codon. A host cell may be engineered to stably express the two luciferase genes and the suppressor tRNA whose expression is regulated by a controlled regulatory element (such as a tetracycline controlled regulatory element). In the absence of an agent such as tetracycline, the suppressor tRNA is not expressed and thus the red-to-green ratio is low. In the presence of an agent such as tetracycline, the suppressor tRNA is expressed and thus the red-to-green ratio increases. For a high throughput screening, cells are plated in the presence of a compound. After a certain time-period media containing an agent such as tetracycline is added to induce suppressor tRNA expression.

Compounds that inhibit tRNA splicing endonuclease will decrease the red-to-green ration compared to a control without the compound. Once compounds are identified in this assay that modulate the activity of animalia tRNA splicing endonuclease, they may be tested using one or more of the assays described above to confirm their activity.

4.4.6 FISH Assay

The activity of an animalia tRNA splicing endonuclease may be determined in an assay in which the persistence and quantity of tRNA intron is detected in an animalia cell. The amount of tRNA intron is quantified at different time points after or during the incubation of the cell with the compound. The tRNA intron can be detected by means of Fluorescence in situ hybridization (FISH) using a tRNA intron-specific probe. In certain embodiments, a control experiment is conducted in parallel wherein the animalia cell is not contacted with a compound.

In the absence of an inhibitor of animalia tRNA splicing endonuclease, the splicing reaction is fast and the concentration of intron in the cell is low. Without being bound by theory, because the spliced intron is normally degraded the concentration of tRNA intron in the animalia cell is below the detection threshold. In the presence of an inhibitor of animalia tRNA splicing endonuclease, the splicing reaction is slowed down and the amount of tRNA intron increases. Thus, a compound that inhibits animalia tRNA splicing endonuclease can be identified by its ability to increase the level of tRNA intron in the animalia cell.

Methods for conducting FISH are well-known to the skilled artisan and can be used with the invention. Exemplary methods for FISH are described in Sarkar and Hopper, 1998 (Mol. Biol. Cell 9:3041-3055), which is incorporated herein in its entirety.

In certain embodiments, a FISH assay is used to determine the effect of a compound on the activity of an animalia tRNA splicing endonuclease in a high-throughput screen. In particular a 96-lens microscope can be used for a high-throughput screen based on FISH. In a specific embodiment, 96 cell cultures are incubated in a 96-well plate with different compounds. Subsequently, the cells are subjected to a FISH analysis using a tRNA intron specific probe and analyzed using the 96-lens microscope. The presence of a signal or the presence of a significantly stronger signal demonstrates that tRNA intron was present in the cells at elevated levels and thus the compound is a candidate inhibitor of tRNA splicing endonuclease.

Without being bound by theory, the FISH assay identifies the compound as inhibitor of the tRNA splicing endonuclease directly. Thus, in certain embodiments, a compound that was identified in a FISH assay as an inhibitor of tRNA splicing is a prima facie candidate for an inhibitor of tRNA splicing endonuclease.

4.4.7 Other Screening Assays

The activity of an animalia tRNA splicing endonuclease may be determined in an assay in which the amount of substrate for a tRNA splicing endonuclease cleaved by the endonuclease in the presence of a compound relative to a control (preferably, a negative control and more preferably, a negative control and a positive control) is detected. Such an assay may be conducted by contacting or incubating a compound with a labeled substrate for an animalia tRNA splicing endonuclease and a cell-free extract or purified animalia tRNA splicing endonuclease under conditions conducive for tRNA splicing endonuclease activity, and measuring the amount of cleaved substrate. The substrate for the animalia tRNA splicing endonuclease can be labeled with any detectable agent. Useful labels in the present invention can include, but are not limited to, spectroscopic labels such as fluorescent dyes (e.g., fluorescein and derivatives such as fluorescein isothiocyanate (FITC) and Oregon Green™, rhodamine and derivatives (e.g., Texas red, tetramethylrhodimine isothiocynate (TRITC), bora-3a,4a-diaza-s-indacene (BODIPY®) and derivatives, etc.), digoxigenin, biotin, phycoerythrin, AMCA, CyDye™, and the like), radiolabels (e.g., $^3$H, $^{125}$I, $^{35}$S, $^{14}$C, $^{32}$P, etc.), enzymes (e.g., horse radish peroxidase, alkaline phosphatase etc.), spectroscopic colorimetric labels such as colloidal gold or colored glass or plastic (e.g., polystyrene, polypropylene, latex, etc.) beads, or nanoparticles—nanoclusters of inorganic ions with defined dimension from 0.1 to 1000 nm) utilizing techniques known to one of skill in the art.

For example, a substrate of an animalia tRNA splicing endonuclease can be labeled by any method known to the skilled artisan. In certain embodiments, a substrate of an animalia tRNA splicing endonuclease can be labeled using site-specific labeling of RNA with fluorophores. In more specific embodiments, a substrate of an animalia tRNA splicing endonuclease is labeled using the methods described in Qin and Pyle, 1999 (Methods 18(1):60-70), which is incorporated in its entirety herein. The optimal method for labeling of a substrate of an animalia tRNA splicing endonuclease can be determined by the skilled artisan using routine experimentation. In a specific embodiment, a substrate of an animalia tRNA splicing endonuclease is labeled using different methods, different labels and/or different positions in the tRNA substrate for labeling. The differently labeled substrates are then subjected separately to a splicing assay in the presence and absence, respectively of an inhibitor or an activator of an animalia tRNA splicing endonuclease. The optimal label for the screening assays is the label that allows for the most easily detectable and most reproducible detection of the effect of the inhibitor or the activator. Other labeling procedures, however, may also be used that, for example, provide other desirable advantages.

In certain embodiments, a compound is contacted or incubated with a labeled substrate for an animalia tRNA splicing endonuclease and a cell-free extract or purified animalia tRNA splicing endonuclease for at least 5 minutes, at least 10 minutes, at least 15 minutes, at least 30 minutes, at least 1 hour, at least 2 hours, or more. The amount of cleaved substrate is proportional to the activity of the tRNA splicing endonuclease. The amount of cleaved tRNA splicing endonuclease can be measured by any technique known to one skilled in the art.

In certain embodiments, the cleaved tRNA splicing endonuclease substrate is separated from the uncleaved tRNA splicing endonuclease substrate by gel-electrophoresis. The amount of cleaved tRNA splicing endonuclease substrate can be quantified by measuring the intensity of the signal of the cleaved tRNA splicing endonuclease substrate. The stronger the signal produced by the cleaved tRNA splicing endonuclease substrate relative to the uncleaved tRNA splicing endonuclease substrate the more active is the tRNA splicing endonuclease. The signal intensity can be quantified using autoradiography or a phosphoimager. If the activity of the tRNA splicing endonuclease is decreased in the presence of a compound, i.e., if the signal of the cleaved tRNA splicing endonuclease substrate relative to the uncleaved tRNA splicing endonuclease substrate is decreased compared to the reaction without the compound or in the presence of a negative control, the compound is identified as an inhibitor of the tRNA splicing endonuclease.

In other embodiments, the amount of cleaved tRNA is determined using mass spectrometry.

4.5 Characterization of the Structure of Compounds

If the library comprises arrays or microarrays of compounds, wherein each compound has an address or identifier, the compound can be deconvoluted, e.g., by cross-referencing the positive sample to original compound list that was applied to the individual test assays.

If the library is a peptide or nucleic acid library, the sequence of the compound can be determined by direct sequencing of the peptide or nucleic acid. Such methods are well known to one of skill in the art.

A number of physico-chemical techniques can be used for the de novo characterization of compounds bound to the target RNA. Examples of such techniques include, but are not limited to, mass spectrometry, NMR spectroscopy, X-ray crystallography and vibrational spectroscopy.

4.5.1 Mass Spectrometry

Mass spectrometry (e.g., electrospray ionization ("ESI"), matrix-assisted laser desorption-ionization ("MALDI"), Fourier-transform ion cyclotron resonance ("FT-ICR") can be used for elucidating the structure of a compound.

MALDI uses a pulsed laser for desorption of the ions and a time-of-flight analyzer, and has been used for the detection of noncovalent tRNA:amino-acyl-tRNA synthetase complexes (Gruic-Sovulj et al., 1997, J. Biol. Chem. 272:32084-32091). However, covalent cross-linking between the target nucleic acid and the compound is required for detection, since a non-covalently bound complex may dissociate during the MALDI process.

ESI mass spectrometry ("ESI-MS") has been of greater utility for studying non-covalent molecular interactions because, unlike the MALDI process, ESI-MS generates molecular ions with little to no fragmentation (Xavier et al., 2000, Trends Biotechnol. 18(8):349-356). ESI-MS has been used to study the complexes formed by HIV Tat peptide and protein with the TAR RNA (Sannes-Lowery et al., 1997, Anal. Chem. 69:5130-5135).

Fourier-transform ion cyclotron resonance ("FT-ICR") mass spectrometry provides high-resolution spectra, isotope-resolved precursor ion selection, and accurate mass assignments (Xavier et al., 2000, Trends Biotechnol. 18(8):349-356). FT-ICR has been used to study the interaction of aminoglycoside antibiotics with cognate and non-cognate RNAs (Hofstadler et al., 1999, Anal. Chem. 71:3436-3440; and Griffey et al., 1999, Proc. Natl. Acad. Sci. USA 96:10129-10133). As true for all of the mass spectrometry methods discussed herein, FT-ICR does not require labeling a compound.

An advantage of mass spectroscopy is not only the elucidation of the structure of the compound, but also the determination of the structure of the compound bound to an RNA. Such information can enable the discovery of a consensus structure of a compound that specifically binds to an RNA.

4.5.2 NMR Spectroscopy

NMR spectroscopy is a valuable technique for identifying complexed target nucleic acids by qualitatively determining changes in chemical shift, specifically from distances measured using relaxation effects, and NMR-based approaches have been used in the identification of small molecule binders of protein drug targets (Xavier et al., 2000, Trends Biotechnol. 18(8):349-356). The determination of structure-activity relationships ("SAR") by NMR is the first method for NMR described in which small molecules that bind adjacent sub-sites are identified by two-dimensional $^1$H-$^{15}$N spectra of the target protein (Shuker et al., 1996, Science 274:1531-1534). The signal from the bound molecule is monitored by employing line broadening, transferred NOEs and pulsed field gradient diffusion measurements (Moore, 1999, Curr. Opin. Biotechnol. 10:54-58). A strategy for lead generation by NMR using a library of small molecules has been recently described (Fejzo et al., 1999, Chem. Biol. 6:755-769).

SAR by NMR can be used to elucidate the structure of a compound.

As described above, NMR spectroscopy is a technique for identifying binding sites in target nucleic acids by qualitatively determining changes in chemical shift, specifically from distances measured using relaxation effects. Examples of NMR that can be used for the invention include, but are not limited to, one-dimentional NMR, two-dimentional NMR, correlation spectroscopy ("COSY"), and nuclear Overhauser effect ("NOE") spectroscopy. Such methods of structure determination of compounds are well-known to one of skill in the art.

Similar to mass spectroscopy, an advantage of NMR is the not only the elucidation of the structure of the compound, but also the determination of the structure of the compound bound to the RNA. Such information can enable the discovery of a consensus structure of a compound that specifically binds to an RNA.

4.5.3 X Ray Crystallography

X-ray crystallography can be used to elucidate the structure of a compound. For a review of x-ray crystallography see, e.g., Blundell et al. 2002, Nat Rev Drug Discov 1(1):45-54. The first step in x-ray crystallography is the formation of crystals. The formation of crystals begins with the preparation of highly purified and soluble samples. The conditions for crystallization is then determined by optimizing several solution variables known to induce nucleation, such as pH, ionic strength, temperature, and specific concentrations of organic additives, salts and detergent. Techniques for automating the crystallization process have been developed to automate the production of high-quality protein crystals. Once crystals have been formed, the crystals are harvested and prepared for data collection. The crystals are then analyzed by diffraction (such as multi-circle diffractometers, high-speed CCD detectors, and detector off-set). Generally, multiple crystals must be screened for structure determinations.

4.5.4 Vibrational Spectroscopy

Vibrational spectroscopy (e.g. infrared (IR) spectroscopy or Raman spectroscopy) can be used for elucidating the structure of a compound.

Infrared spectroscopy measures the frequencies of infrared light (wavelengths from 100 to 10,000 nm) absorbed by the compound as a result of excitation of vibrational modes according to quantum mechanical selection rules which require that absorption of light cause a change in the electric dipole moment of the molecule. The infrared spectrum of any molecule is a unique pattern of absorption wavelengths of varying intensity that can be considered as a molecular fingerprint to identify any compound.

Infrared spectra can be measured in a scanning mode by measuring the absorption of individual frequencies of light, produced by a grating which separates frequencies from a mixed-frequency infrared light source, by the compound relative to a standard intensity (double-beam instrument) or pre-measured (blank') intensity (single-beam instrument). In a preferred embodiment, infrared spectra are measured in a pulsed mode ("FT-IR") where a mixed beam, produced by an interferometer, of all infrared light frequencies is passed through or reflected off the compound. The resulting interferogram, which may or may not be added with the resulting interferograms from subsequent pulses to increase the signal strength while averaging random noise in the electronic signal, is mathematically transformed into a spectrum using Fourier Transform or Fast Fourier Transform algorithms.

Raman spectroscopy measures the difference in frequency due to absorption of infrared frequencies of scattered visible or ultraviolet light relative to the incident beam. The incident monochromatic light beam, usually a single laser frequency, is not truly absorbed by the compound but interacts with the electric field transiently. Most of the light scattered off the sample will be unchanged (Rayleigh scattering) but a portion of the scatter light will have frequencies that are the sum or difference of the incident and molecular vibrational frequencies. The selection rules for Raman (inelastic) scattering require a change in polarizability of the molecule. While some vibrational transitions are observable in both infrared and Raman spectrometry, must are observable only with one or the other technique. The Raman spectrum of any molecule is a unique pattern of absorption wavelengths of varying intensity that can be considered as a molecular fingerprint to identify any compound.

Raman spectra are measured by submitting monochromatic light to the sample, either passed through or preferably reflected off, filtering the Rayleigh scattered light, and detecting the frequency of the Raman scattered light. An improved Raman spectrometer is described in U.S. Pat. No. 5,786,893 to Fink et al., which is hereby incorporated by reference.

Vibrational microscopy can be measured in a spatially resolved fashion to address single beads by integration of a visible microscope and spectrometer. A microscopic infrared spectrometer is described in U.S. Pat. No. 5,581,085 to Reffner et al., which is hereby incorporated by reference in its entirety. An instrument that simultaneously performs a microscopic infrared and microscopic Raman analysis on a sample is described in U.S. Pat. No. 5,841,139 to Sostek et al., which is hereby incorporated by reference in its entirety.

In one embodiment of the method, compounds are synthesized on polystyrene beads doped with chemically modified styrene monomers such that each resulting bead has a characteristic pattern of absorption lines in the vibrational (IR or Raman) spectrum, by methods including but not limited to those described by Fenniri et al., 2000, J. Am. Chem. Soc. 123:8151-8152. Using methods of split-pool synthesis familiar to one of skill in the art, the library of compounds is prepared so that the spectroscopic pattern of the bead identifies one of the components of the compound on the bead. Beads that have been separated according to their ability to bind target RNA can be identified by their vibrational spectrum. In one embodiment of the method, appropriate sorting and binning of the beads during synthesis then allows identification of one or more further components of the compound on any one bead. In another embodiment of the method, partial identification of the compound on a bead is possible through use of the spectroscopic pattern of the bead with or without the aid of further sorting during synthesis, followed by partial resynthesis of the possible compounds aided by doped beads and appropriate sorting during synthesis.

In another embodiment, the IR or Raman spectra of compounds are examined while the compound is still on a bead, preferably, or after cleavage from bead, using methods including but not limited to photochemical, acid, or heat treatment. The compound can be identified by comparison of the IR or Raman spectral pattern to spectra previously acquired for each compound in the combinatorial library.

4.6 Secondary Assays

The compounds identified in the assays described supra that modulate the activity of an animalia tRNA splicing endonuclease (for convenience referred to herein as a "lead" compound) can be further tested for both direct binding to RNA and biological activity. In one embodiment, the compounds are tested for biological activity in further assays and/or animal models. In another embodiment, the lead compound is used to design congeners or analogs. In another embodiment, the lead compound is used to assess the effect on fungal tRNA splicing endonuclease and fungal proliferation. In yet another embodiment, mutagenesis studies can be conducted to assess the mechanism by which a lead compound is modulating the activity of an animalia tRNA splicing endonuclease.

4.6.1 Phenotypic or Physiological Readout

The compounds identified in the assays described supra (for convenience referred to herein as a "lead" compound) can be tested for biological activity using host cells containing or engineered to contain an animalia tRNA splicing endonuclease coupled to a functional readout system. For example, a phenotypic or physiological readout can be used to assess activity of an animalia tRNA splicing endonuclease in the presence and absence of the lead compound.

In one embodiment, a phenotypic or physiological readout can be used to assess activity of an animalia tRNA splicing endonuclease in the presence and absence of the lead compound. For example, the animalia tRNA splicing endonuclease may be overexpressed in a cell in which the animalia tRNA splicing endonuclease is endogenously expressed. The effect of a lead compound can be assayed by measuring the cell growth or viability of the target cell. Such assays can be carried out with representative cells of cell types involved in a particular proliferative disorder. A lower level of proliferation or survival of the contacted cells indicates that the lead compound is effective to treat a condition in the patient characterized by uncontrolled cell growth. Alternatively, instead of culturing cells from a patient, a lead compound may be screened using cells of a tumor or malignant cell line or an endothelial cell line. Specific examples of cell culture models include, but are not limited to, for lung cancer, primary rat lung tumor cells (Swafford et al., 1997, Mol. Cell. Biol., 17:1366-1374) and large-cell undifferentiated cancer cell lines (Mabry et al., 1991, Cancer Cells, 3:53-58); colorectal cell lines for colon cancer (Park and Gazdar, 1996, J. Cell Biochem. Suppl. 24:131-141); multiple established cell lines for breast cancer (Hambly et al., 1997, Breast Cancer Res.

Treat. 43:247-258; Gierthy et al., 1997, Chemosphere 34:1495-1505; Prasad and Church, 1997, Biochem. Biophys. Res. Commun. 232:14-19); a number of well-characterized cell models for prostate cancer (Webber et al., 1996, Prostate, Part 1, 29:386-394; Part 2, 30:58-64; and Part 3, 30:136-142; Boulikas, 1997, Anticancer Res. 17:1471-1505); for genitourinary cancers, continuous human bladder cancer cell lines (Ribeiro et al., 1997, Int. J. Radiat. Biol. 72:11-20); organ cultures of transitional cell carcinomas (Booth et al., 1997, Lab Invest. 76:843-857) and rat progression models (Vet et al., 1997, Biochim. Biophys Acta 1360:39-44); and established cell lines for leukemias and lymphomas (Drexler, 1994, Leuk. Res. 18:919-927, Tohyama, 1997, Int. J. Hematol. 65:309-317). More specific examples of cell lines include the cancer cell line Huh7 (human hepatocellular carcinoma cell line) and the cancer cell line Caco-2 (a colon-cancer cell line). In certain embodiments, the effect of a lead compound on the growth and/or viability of a cancerous cell of a transformed cell is compared to the effect of such a compound on the growth and/or viability of non-cancerous, normal cells. Preferably, compounds that differentially affect the growth and/or viability of cancerous cells or transformed cells are chosen as anti-proliferative agents.

Many assays well-known in the art can be used to assess the survival and/or growth of a patient cell or cell line following exposure to a lead compound; for example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or (3H)-thymidine incorporation (see, e.g., Chen, J., 1996, Oncogene 13:1395-403; Jeoung, J., 1995, J. Biol. Chem. 270:18367-73), by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as Western blotting or immunoprecipitation using commercially available antibodies. mRNA can be quantitated using methods that are well known and routine in the art, for example, using northern analysis, RNase protection, the polymerase chain reaction in connection with the reverse transcription. Cell viability can be assessed by using trypan-blue staining or other cell death or viability markers known in the art. In a specific embodiment, the level of cellular ATP is measured to determined cell viability. Differentiation can be assessed, for example, visually based on changes in morphology.

The lead compound can also be assessed for its ability to inhibit cell transformation (or progression to malignant phenotype) in vitro. In this embodiment, cells with a transformed cell phenotype are contacted with a lead compound, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, *General Virology*, 3d Ed., John Wiley & Sons, New York, pp. 436-446).

Loss of invasiveness or decreased adhesion can also be assessed to demonstrate the anti-cancer effects of a lead compound. For example, an aspect of the formation of a metastatic cancer is the ability of a precancerous or cancerous cell to detach from primary site of disease and establish a novel colony of growth at a secondary site. The ability of a cell to invade peripheral sites reflects its potential for a cancerous state. Loss of invasiveness can be measured by a variety of techniques known in the art including, for example, induction of E-cadherin-mediated cell-cell adhesion. Such E-cadherin-mediated adhesion can result in phenotypic reversion and loss of invasiveness (Hordijk et al., 1997, Science 278:1464-66).

Loss of invasiveness can further be examined by inhibition of cell migration. A variety of 2-dimensional and 3-dimensional cellular matrices are commercially available (Calbiochem-Novabiochem Corp. San Diego, Calif.). Cell migration across or into a matrix can be examined using microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464-66).

Alternatively, loss of invasiveness can be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated can then be correlated with invasiveness (see e.g., Ohnishi, T., 1993, Biochem. Biophys. Res. Commun. 193:518-25).

In certain embodiments, a lead compound is tested for its effects, such as, but not limited to, cytotoxicity, altered gene expression, and altered morphology, on PBMCs (Peripheral Blood Mononuclear Cells).

4.6.2 Animal Models

The lead compounds identified in the assays described herein can be tested for biological activity using animal models for a proliferative disorder. These include animals engineered to contain an animalia tRNA splicing endonuclease coupled to a functional readout system, such as a transgenic mouse. Such animal model systems include, but are not limited to, rats, mice, chicken, cows, monkeys, pigs, dogs, rabbits, etc. In a specific embodiment of the invention, a compound identified in accordance with the methods of the invention is tested in a mouse model system. Such model systems are widely used and well-known to the skilled artisan such as the SCID mouse model or transgenic mice.

The anti-angiogenic activity of a compound identified in accordance with the invention can be determined by using various experimental animal models of vascularized tumors. The anti-tumor activity of a compound identified in accordance with the invention can be determined by administering the compound to an animal model and verifying that the compound is effective in reducing the proliferation or spread of cancer cells in said animal model. An example of an animal model for human cancer in general includes, but is not limited to, spontaneously occurring tumors of companion animals (see, e.g., Vail & MacEwen, 2000, Cancer Invest 18(8):781-92).

Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCRbeta and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63).

The toxicity and/or efficacy of a compound identified in accordance with the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). Cells and cell lines that can be used to assess the cytotoxicity of a compound identified in accordance with the invention include, but are not limited to, peripheral blood mononuclear cells (PBMCs), Caco-2 cells, and Huh7 cells. The dose ratio between toxic and therapeutic effects is the therapeutic index and it can be expressed as the ratio $LD_{50}/ED_{50}$. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the compound that achieves a half-maximal inhibition of symptoms) as determined in cell culture. Such information can be used to more accurately determine useful doses in humans. Levels in plasma may be measured, for example, by high performance liquid chromatography.

4.6.3 Design of Congeners or Analogs

The compounds which display the desired biological activity can be used as lead compounds for the development or design of congeners or analogs having useful pharmacological activity. For example, once a lead compound is identified, molecular modeling techniques can be used to design variants of the compound that can be more effective. Examples of molecular modeling systems are the CHARM and QUANTA programs (Polygen Corporation, Waltham, Mass.). CHARM performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159-166; Ripka, 1998, New Scientist 54-57; McKinaly & Rossmann, 1989, Annu Rev. Pharmacol. Toxiciol. 29:111-122; Perry & Davies, OSAR: Quantitative Structure-Activity Relationships in Drug Design pp. 189-193 (Alan R. Liss, Inc. 1989); Lewis & Dean, 1989, Proc. R. Soc. Lond. 236:125-140 and 141-162; Askew et al., 1989, J. Am. Chem. Soc. 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to any identified region. The analogs and congeners can be tested for binding to an animalia tRNA splicing endonuclease using the above-described screens for biologic activity. Alternatively, lead compounds with little or no biologic activity, as ascertained in the screen, can also be used to design analogs and congeners of the compound that have biologic activity.

4.6.4 Fungal Assays

Various fungal assays can be conducted to determine the specificity of a lead compound for an animalia tRNA splicing endonuclease. Any of the assays described above with respect to animalia tRNA splicing endonuclease can be used to assess the effect of a lead compound on fungal tRNA splicing endonuclease. Compounds that affect both animalia tRNA splicing endonuclease and fungal tRNA splicing endonuclease may be used to treat, prevent or ameliorate one or more symptoms of cancer and/or a fungal infection in a cancer patient.

4.6.4.1 Fungal Cell-Based Assays with a Labeled Substrate

The FRET cell-based assays may be conducted by microinjecting a substrate for a fungal tRNA splicing endonuclease into a fungal cell and contacting the fungal cell with a compound, wherein the substrate is labeled at the 5' end with a fluorophore and labeled at the 3' end with a quencher, or alternatively the substrate is labeled at the 5' end with a quencher and labeled at the 3' end with a fluorophore, and measuring the fluorescence of the substrate by, e.g., a fluorescence emission detector such as a Viewlux or Analyst. The endogenous tRNA splicing endonuclease will cleave the substrate and result in the production of a detectable fluorescent signal. A compound that inhibits or reduces the activity of the endogenous tRNA splicing endonuclease will inhibit or reduce the cleavage of the substrate and thus, inhibit or reduce the production of a detectable fluorescent signal relative to a negative control (e.g., PBS). A compound that enhances the activity of the endogenous endonuclease will enhance the cleavage of the substrate and thus, increase the production of a detectable fluorescent signal relative to a negative control (e.g., PBS).

Alternatively, the FRET cell-based assays may be conducted by microinjecting a substrate for a fungal tRNA splicing endonuclease into a fungal cell and contacting the fungal cell with a compound, wherein the substrate is labeled at the 5' end with a fluorescent donor moiety and labeled at the 3' end with a fluorescent acceptor moiety, or the substrate is labeled at the 5' end with a fluorescent acceptor moiety and labeled at the 3' end with a fluorescent donor moiety, and measuring the fluorescence of the substrate by, e.g., a fluorescence emission detector such as a Viewlux or Analyst. The endogenous tRNA splicing endonuclease will cleave the substrate and result in the production of a detectable fluorescent signal by the fluorescent donor moiety and fluorescent acceptor moiety at the wavelength of the fluorescent donor. A compound that inhibits or reduces the activity of the endogenous tRNA splicing endonuclease will inhibit or reduce cleavage of the substrate and thus, increase the fluorescence emission of the fluorescent acceptor moiety at the wavelength of the fluorescent donor moiety relative to a negative control (e.g., PBS). A compound that enhances the activity of the endogenous tRNA splicing endonuclease will enhance the cleavage of the substrate and thus, reduce the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET fungal cell-based assays described herein.

Any nucleotide sequence recognized and excised by a fungal tRNA splicing endonuclease may be utilized as a substrate for a fungal tRNA splicing endonuclease in a FRET assay described herein. For example, a nucleotide sequence comprising a bulge-helix-bulge structure or a mature domain of a precursor tRNA may be utilized as a substrate for a fungal tRNA splicing endonuclease in a FRET assay described herein. A nucleotide sequence recognized and excised by a fungal tRNA splicing endonuclease may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In a specific embodiment, the substrates for a tRNA splicing endonuclease utilized in the FRET assays described herein comprise a tRNA intron. The intron may have a bulge-helix-bulge conformation. In a preferred embodiment, the nucleotide sequence comprises a mature domain that contains an intron.

In accordance with the invention, the substrate can be labeled with a single pair of fluorescent donor and acceptor compounds. The substrate can be labeled with different pairs of fluorescent donor moieties and fluorescent acceptor moieties. For example, two, three, four, five or more pairs of fluorescent donor moieties and fluorescent acceptor moieties can be used. In this situation, preferably, at least one of the pairs comprise a fluorescent acceptor moiety that has a different emission spectrum from the fluorescent acceptor moiety of at least one of the other pairs. Alternatively, when at least three pairs are used, the fluorescent acceptor moiety of the first pair, second pair and third pair has a different emission spectrum than the fluorescent acceptor moiety of the other two. Methods for labeling the substrate with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety). The labeled substrate can be microinjected into fungal cells (preferably, yeast) utilized techniques well-known to one of skill in the art.

The activity of a compound on a fungal tRNA splicing endonuclease in the FRET cell-based assays can be determined by measuring the fluorescent emission spectra of the substrate utilizing techniques well-known to one of skill in the art. The fluorescent emission spectra measured depends, in part, on the fluorophore used.

4.6.4.2 Fungal Extract Assays with a Labeled Substrate

The FRET cell-free-based assays may be conducted by contacting a substrate for a fungal tRNA splicing endonuclease with a fungal extract (e.g., a yeast extract) or a purified fungal tRNA splicing endonuclease and a compound, wherein the substrate is labeled at the 5' end with a fluorophore and labeled at the 3' end with a quencher, or alternatively, the substrate is labeled at the 5' end with a quencher and labeled at the 3' end with a fluorophore, and measuring the fluorescence of the substrate by, e.g., a fluorescence emission detector such as a Viewlux or Analyst. The tRNA splicing endonuclease will cleave the substrate and result in the production of a detectable fluorescent signal. A compound that inhibits or reduces the activity of the tRNA splicing endonuclease will inhibit or reduce the cleavage of the substrate and thus, inhibit or reduce the production of a detectable fluorescent signal relative to a negative control (e.g., PBS). A compound that enhances the activity of the endogenous endonuclease will enhance the cleavage of the substrate and thus, increase the production of a detectable fluorescent signal relative to a negative control (e.g., PBS).

Alternatively, the FRET cell-free-based assays may be conducted by contacting a substrate for a fungal tRNA splicing endonuclease with a cell-free extract or a purified fungal tRNA splicing endonuclease and a compound, wherein the substrate is labeled at the 5' end with a fluorescent donor moiety and labeled at the 3' end with a fluorescent acceptor moiety, or the substrate is labeled at the 5' end with a fluorescent acceptor moiety and labeled at the 3' end with a fluorescent donor moiety, and measuring the fluorescence of the substrate by, e.g., a fluorescence emission detector such as a Viewlux or Analyst. The tRNA splicing endonuclease in the fungal extract will cleave the substrate and result in the production of a detectable fluorescent signal by the fluorescent donor moiety and fluorescent acceptor moiety at the wavelength of the fluorescent donor moiety. A compound that inhibits or reduces the activity of the endogenous tRNA splicing endonuclease will inhibit or reduce cleavage of the substrate and thus, increase the fluorescence emission of the fluorescent acceptor moiety at the wavelength of the fluorescent donor moiety relative to a negative control (e.g., PBS). A compound that enhances the activity of the endogenous tRNA splicing endonuclease will enhance the cleavage of the substrate and thus, reduce the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET fungal extract assays described herein.

In accordance with the invention, the substrate can be labeled with a single pair of fluorescent donor and acceptor moieties. The substrate can be labeled with different pairs of fluorescent donor moieties and fluorescent acceptor moieties. For example, two, three, four, five or more pairs of fluorescent donor moieties and fluorescent acceptor moieties can be used. In this situation, preferably, at least one of the pairs comprise a fluorescent acceptor moiety that has a different emission spectrum from the fluorescent acceptor moiety of at least one of the other pairs. Alternatively, when at least three pairs are used, the fluorescent acceptor moiety of the first pair, second pair and third pair has a different emission spectrum than the fluorescent acceptor moiety of the other two. Methods for labeling the substrate with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety).

The activity of a compound on a fungal tRNA splicing endonuclease in the FRET fungal extract assays can be determined by measuring the fluorescent emission spectra of the substrate utilizing techniques well-known to one of skill in the art. The fluorescent emission spectra measured depends, in part, on the fluorophore used.

In certain embodiments, an animalia tRNA splicing endonuclease subunit is labeled with a fluorophore and the tRNA substrate is labeled with a fluorophore such that binding of the tRNA substrate to the animalia tRNA splicing endonuclease results in FRET. Compounds can then be assayed for their ability to inhibit FRET. If a compound prevents or reduces FRET between the labeled substrate and the animalia tRNA splicing endonuclease, the compound is identified as an inhibitor of the animalia tRNA splicing endonuclease-tRNA interaction. This compound can then be assayed for its ability to inhibit the endonuclease activity of the animalia tRNA splicing endonuclease by any assay well known to the skilled artisan (see, e.g., above).

4.6.4.3 Fungal Cell-Based Assays with Labeled Enzyme

A FRET cell-based assay may be conducted by microinjecting or transfecting a first subunit of a fungal tRNA splicing endonuclease (e.g., SEN2) labeled with a fluorophore and a second, different subunit of a fungal tRNA splicing endonuclease (e.g., SEN34) labeled with a quencher into a fungal cell and contacting the fungal cell with a compound, and measuring the fluorescence of the fungal tRNA splicing endonuclease by, e.g., a fluorescence emission detector such as a Viewlux or Analyst. Preferably, the cell microinjected or transfected is deficient in one or more of the subunits of the fungal tRNA splicing endonuclease. The formation of the fungal tRNA splicing endonuclease from the labeled subunits will result in a reduction in the fluorescence detectable. A compound that inhibits or reduces the formation of the fungal tRNA splicing endonuclease will enhance the production of detectable fluorescent signal relative to a negative control (e.g., PBS). A compound that enhances the formation of the fungal tRNA splicing endonuclease will reduce or inhibit the fluorescence detectable relative to a negative control (e.g., PBS).

Alternatively, a FRET cell-based assay may be conducted by microinjecting or transfecting a first subunit of a fungal tRNA splicing endonuclease (e.g., SEN2) labeled with a fluorescent donor moiety and a second, different subunit of a fungal tRNA splicing endonuclease (e.g., SEN34) labeled with a fluorescent acceptor moiety into a fungal cell and contacting the fungal cell with a compound, and measuring the fluorescence of the fungal tRNA splicing endonuclease by, e.g., a fluorescence emission detector such as a Viewlux or Analyst. The formation of the fungal tRNA splicing endonuclease will result in the production of a detectable fluorescent signal by the fluorescent donor moiety and fluorescent acceptor moiety at the wavelength of the fluorescent donor moiety. A compound that inhibits or reduces the formation of the fungal tRNA splicing endonuclease will reduce the fluorescence emission of the fluorescent acceptor moiety at the wavelength of the fluorescent donor moiety relative to a negative control (e.g., PBS). A compound that enhances the formation of the fungal tRNA splicing endonuclease will increase the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET fungal cell-based assays described herein.

Methods for labeling a subunit of a fungal tRNA splicing endonuclease with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety).

4.6.4.4 Other Fungal Assays with Labeled Enzyme

A FRET assay may be conducted by contacting a first subunit of a fungal tRNA splicing endonuclease (e.g., SEN2) labeled with a fluorophore and a second subunit of a fungal tRNA splicing endonuclease (e.g., SEN34) labeled with a quencher with a compound in vitro under conditions conducive to the formation of the endonuclease, and measuring the fluorescence of the fungal tRNA splicing endonuclease by, e.g., a fluorescence emission detector such as a Viewlux or Analyst. The formation of the fungal tRNA splicing endonuclease from the labeled subunits will result in a reduction in the fluorescence detectable. A compound that inhibits or reduces the formation of the fungal tRNA splicing endonuclease will enhance the production of detectable fluorescent signal relative to a negative control (e.g., PBS). A compound that enhances the formation of the fungal tRNA splicing endonuclease will reduce or inhibit the fluorescence detectable relative to a negative control (e.g., PBS).

Alternatively, a FRET fungal assay may be conducted by contacting a first subunit of a fungal tRNA splicing endonuclease (e.g., SEN2) labeled with a fluorescent donor moiety and a second, different subunit of a fungal tRNA splicing endonuclease (e.g., SEN34) labeled with a fluorescent acceptor moiety with a compound in vitro under conditions conducive to the formation of the endonuclease, and measuring the fluorescence of the fungal tRNA splicing endonuclease by, e.g., a fluorescence emission detector such as a Viewlux or Analyst. The formation of the fungal tRNA splicing endonuclease will result in the production of a detectable fluorescent signal by the fluorescent donor moiety and fluorescent acceptor moiety at the wavelength of the fluorescent donor moiety. A compound that inhibits or reduces the formation of the fungal tRNA splicing endonuclease will reduce the fluorescence emission of the fluorescent acceptor moiety at the wavelength of the fluorescent donor moiety relative to a negative control (e.g., PBS). A compound that enhances the formation of the fungal tRNA splicing endonuclease will increase the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET fungal assays described herein.

4.6.4.5 Fluorescence Polarization Assay

The effect of a compound on the activity of an fungal tRNA splicing endonuclease may be determined utilizing a fluorescence polarization-based assay. In such an assay, a fluorescently labeled substrate for a fungal tRNA splicing endonuclease is contacted with an fungal cell-free extract (preferably, a fungal tRNA splicing endonuclease extract) or a purified fungal tRNA splicing endonuclease and a compound or a member of a library of compounds; and the fluorescently polarized light emitted is measured. An important aspect of this assay is that the size of the substrate used in the assay is large enough to distinguish a change in fluorescent polarized light emitted following cleavage of the substrate. The fungal tRNA splicing endonuclease in the cell-free extract or the purified fungal tRNA splicing endonuclease will cleave the substrate and result in a change in intensity of emitted polarized light. Fluorescently labeled substrates when excited with plane polarized light will emit light in a fixed plane only if they do not rotate during the period between excitation and emission. The extent of depolarization of the emitted light depends upon the amount of rotation of the substrate, which is dependent on the size of the substrate. Small substrates rotate more than larger substrates between the time they are excited and the time they emit fluorescent light. A small fluorescently labeled substrate rotates rapidly and the emitted light is depolarized. A large fluorescently labeled substrate rotates more slowly and results in the emitted light remaining polarized. A compound that inhibits the activity of the fungal tRNA splicing endonuclease will inhibit or reduce the cleavage of the substrate and thus, decrease the rotation of the substrate relative to a negative control (e.g., PBS), which will result in the emitted light remaining polarized. A compound that enhances the activity of the fungal tRNA splicing endonuclease will enhance the cleavage of the substrate and thus, increase the rotation of the substrate relative to a negative control (e.g., PBS), which will result in more of the emitted light being depolarized.

The light intensities are measured in planes 90° apart and are many times designated the horizontal and vertical intensities. In some instruments the excitation filter is moveable while the emission filter is fixed. In certain other machines the horizontal and vertical intensities are measured simultaneously via fiber optics. Research grade fluorescence polarization instruments are commercially available from, e.g., Pan Vera, BMG Lab Technologies, and LJL Biosystems. Abott provides clinical laboratory instrumentation. The value of fluorescence polarization is determined by the following equation:

$$\text{polarization} = \frac{\text{intensity}_{vertical} - \text{intensity}_{horizontal}}{\text{intensity}_{veritcal} + \text{intensity}_{horizontal}}.$$

Fluorescence polarization values are most often divided by 1000 and expressed as millipolarization units (mP).

4.6.4.6 Anti-Fungal Assays

The anti-fungal effect of a lead compound can be assessed utilizing techniques well-known to one of skill in the art. The invention encompasses methods of anti-fungal susceptibility testing as recommended by the National Committee for Clinical Laboratories (NCCLS) (See National Committee for Clinical Laboratories Standards. 1995, Proposed Standard M27T. Villanova, Pa., all of which is incorporated herein by reference in its entirety) and other methods known to those skilled in the art (Pfaller et al., 1993, *Infectious Dis. Clin. N. Am.* 7: 435-444) The invention encompasses determining anti-fungal activities of the lead compounds of the invention using macrodilution methods and/or microdilution methods using protocols known to those skilled in the art (See, Clancy et al., 1997 *Journal of Clinical Microbiology*, 35(11): 2878-82; Ryder et al., 1998, *Antimicrobial Agents and Chemotherapy*, 42(5): 1057-61; U.S. Pat. No. 5,521,153; U.S. Pat. No. 5,883,120, U.S. Pat. No. 5,521,169, all of which are incorporated by reference in their entirety). Briefly, a fungal strain is cultured in an appropriate liquid media, and grown at an appropriate temperature, depending on the particular fungal strain used for a determined amount of time, which is also depends on the particular fungal strain used. An innoculum is then prepared photometrically and the turbidity of the suspension is matched to that of a standard, e.g., a McFarland standard. The effect of the lead compound on the turbidity of the inoculum is determined visually or spectrophotometrically. The minimal inhibitory concentration of the lead compound (MIC) is determined, which is defined as the lowest concentration of the lead compound which prevents visible growth of an inoculum as measured by determining the culture turbidity.

The invention also encompasses colorimetric based assays for determining the anti-fungal activity of the lead compounds of the invention. One exemplary colorimetric assay for use in the methods of the invention is described by Pfaller et al. (1994, *Journal of Clinical Microbiology*, 32(8): 1993-6, which is incorporated herein by reference in its entirety; also see Tiballi et al., 1995, *Journal of Clinical Microbiology*, 33(4): 915-7). This assay employs a colorimetric endpoint using an oxidation-reduction indicator (Alamar Biosciences, Inc., Sacramento Calif.).

The invention encompasses photometric assays for determining the anti-fungal activity of the lead compounds of the invention using previously described methodology (See Clancy et al., 1997 *Journal of Clinical Microbiology*, 35(11): 2878-82; Jahn et al., 1995, Journal of Clinical Microbiology, 33(3): 661-667 which is incorporated herein by reference in its entirety). This photometric assay is based on quantifying mitochondrial respiration by viable fungi through the reduction of 3-(4,5-dimethyl-2thiazolyl)-2,5,-diphenyl-2H-tetrazolium bromide (MTT) to formazan. MIC's determined by this assay are defined as the highest concentration of the lead compound associated with the first precipitous drop in optical density. In some embodiments, the compounds of the invention are assayed for anti-fungal activity using macrodilution, microdilution and MTT assays in parallel.

The antifungal properties of the lead compounds of the present invention may be determined from a fungal lysis assay, as well as by other methods, including, inter alia, growth inhibition assays, fluorescence-based fungal viability assays, flow cytometry analyses, and other standard assays known to those skilled in the art. The fungi tested in accordance with the invention include, but are not limited to fungi in the genus *Blastomyces*, including *Blastomyces dermatitidis*; *Paracoccidiodes*, including *Paracoccidioides brasiliensis*; *Sporothrix*, including *Sporothrix schenckii*; *Cryptococcus*; *Candida*, including *Candida albicans*, *Candida tropicalis* and *Candida glabrala*; *Aspergillus*, including *Aspergillus fumigarus* and *Aspergillus flavus*; *Histoplasma*, including *Histoplasma capsulatum*; *Cryptococcus*, including *Cryptococcus neoformans*; *Bipolaris*; *Cladophialophora*; *Cladosporium*; *Drechslera*; *Exophiala*; *Fonsecaea*; *Phialophora*; *Xylohypha*; *Ochroconis*; *Rhinocladiella*; *Scolecobasidium*; and *Wangiella*.

4.6.5 Mutagenesis Studies

The subunit(s) of an animalia tRNA splicing endonuclease and/or the nucleotide sequence of a substrate for an animalia tRNA splicing endonuclease that are necessary for a compound identified in accordance with the methods of the invention to modulate the activity of an animalia tRNA splicing endonuclease can be determined utilizing standard mutagenesis techniques well-known to one of skill in the art. One or more mutations (e.g., deletions, additions and/or substitutions) may be introduced into an animalia tRNA splicing endonuclease subunit and the effect of the mutations on the activity of the animalia tRNA splicing endonuclease in the presence or absence of a compound can be determined using an assay described herein. In particular, one or more mutations (e.g., deletions, additions, and/or substitutions) may also be introduced into a substrate for animalia tRNA endonuclease and the effect of the mutations on the activity of the animalia tRNA splicing endonuclease in the presence or absence of a compound can be determined using an assay described herein. For example, one or more mutations (e.g., deletions, additions and/or substitutions) may be introduced into the nucleotide sequence for a tRNA intron within the open frame reading of a reporter gene and the effect on the expression of a reporter gene in a reporter gene-based assay described herein can be determined. If the mutation in the tRNA intron affects the ability of the compound to modulate the expression of the reporter gene, then the mutated sequence plays a role in the activity of the tRNA splicing endonuclease.

Standard techniques known to those of skill in the art can be used to introduce mutations in the nucleotide sequence of an animalia tRNA splicing endonuclease and/or the nucleotide sequence of a substrate for an animalia tRNA splicing endonuclease, including, for example, site-directed mutagenesis and PCR-mediated mutagenesis. In a specific embodiment, less than 75 nucleic acid residue substitutions, less than 50 nucleic acid residue substitutions, less than 45 nucleic acid residue substitutions, less than 40 nucleic acid residue substitutions, less than 35 nucleic acid residue substitutions, less than 30 nucleic acid residue substitutions, less than 25 nucleic acid residue substitutions, less than 20 nucleic acid residue substitutions, less than 15 nucleic acid residue substitutions, less than 10 nucleic acid residue substitutions, or less than 5 nucleic acid residue substitutions are introduced into the nucleotide sequence of an animalia tRNA splicing endonuclease and/or the nucleotide sequence of a substrate for an animalia tRNA splicing endonuclease.

4.7 Use of Identified Compounds to Treat/Prevent a Proliferative Disorder

The present invention provides methods of preventing, treating, managing or ameliorating a proliferative disorder or one or more symptoms thereof, said methods comprising administering to a subject in need thereof one or more compounds identified in accordance with the methods of the invention. In one embodiment, the invention provides a method of preventing, treating, managing or ameliorating a proliferative disorder or one or more symptoms thereof, said method comprising administering to a subject in need thereof a dose of a prophylactically or therapeutically effective amount of one or more compounds identified in accordance with the methods of the invention. In another embodiment, a compound identified in accordance with the methods of the invention is not administered to prevent, treat, or ameliorate a proliferative disorder or one or more symptoms thereof, if such compound has been used previously to prevent, treat, manage or ameliorate said proliferative disorder.

The invention also provides methods of preventing, treating, managing or ameliorating a proliferative disorder or one or more symptoms thereof, said methods comprising administering to a subject in need thereof one or more of the compounds identified utilizing the screening methods described herein, and one or more other therapies (e.g., prophylactic or therapeutic agents), which therapies are currently being used, have been used or are known to be useful in the prevention, treatment, management or amelioration of one or more symptoms associated with said proliferative disorder (including, but not limited to the prophylactic or therapeutic agents listed in Section 4.6.1 hereinbelow). The therapies (e.g., prophylactic or therapeutic agents) of the combination therapies of the invention can be administered sequentially or concurrently. In a specific embodiment, the combination therapies of the invention comprise a compound identified in accordance with the invention and at least one other therapy that has the same mechanism of action as said compound. In another specific embodiment, the combination therapies of the invention comprise a compound identified in accordance with the methods of the invention and at least one other therapy (e.g., prophylactic or therapeutic agent) which has a different mechanism of action than said compound. The combination therapies of the present invention improve the prophylactic or therapeutic effect of a compound of the invention by functioning together with the compound to have an additive or synergistic effect. The combination therapies of the present invention reduce the side effects associated with the therapies (e.g., prophylactic or therapeutic agents).

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In specific embodiment, a pharmaceutical composition comprising one or more compounds identified in a screening assay described herein is administered to a subject, preferably a human, to prevent, treat, manage or ameliorate a proliferative disorder or one or more symptoms thereof. In accordance with the invention, the pharmaceutical composition may also comprise one or more prophylactic or therapeutic agents which are currently being used, have been used or are known to be useful in the prevention, treatment, management or amelioration of a proliferative disorder or one or more symptoms thereof.

A compound identified in accordance with the methods of the invention may be used as a first, second, third, fourth or fifth line of therapy for a proliferative disorder. The invention provides methods for treating, managing or ameliorating a proliferative disorder or one or more symptoms thereof in a subject refractory to conventional therapies for such proliferative disorder, said methods comprising administering to said subject a dose of a prophylactically or therapeutically effective amount of a compound identified in accordance with the methods of the invention. In particular, a cancer may be determined to be refractory to a therapy means when at least some significant portion of the cancer cells are not killed or their cell division arrested in response to the therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced, or has increased.

The invention provides methods for treating, managing or ameliorating one or more symptoms of a proliferative disorder in a subject refractory to existing single agent therapies for such proliferative disorder, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating or managing a proliferative disorder by administering a compound identified in accordance with the methods of the invention in combination with any other therapy (e.g., radiation therapy, chemotherapy or surgery) to patients who have proven refractory to other therapies but are no longer on these therapies. The invention also provides methods for the treatment or management of a patient having a proliferative disorder and immunosuppressed by reason of having previously undergone other therapies. The invention also provides alternative methods for the treatment or management of a proliferative disorder such as cancer where chemotherapy, radiation therapy, hormonal therapy, and/or biological therapy/immunotherapy has proven or may prove too toxic, i.e., results in unacceptable or unbearable side effects, for the subject being treated or managed. Further, the invention provides methods for preventing the recurrence of a proliferative disorder such as cancer in patients that have been treated and have no disease activity by administering a compound identified in accordance with the methods of the invention.

Proliferative disorders that can be treated by the methods encompassed by the invention include, but are not limited to, neoplasms, tumors, metastases, or any disease or disorder characterized by uncontrolled cell growth (e.g., psoriasis and pulmonary fibrosis). The cancer may be a primary or metastatic cancer. Specific examples of cancers that can be treated by the methods encompassed by the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America). It is also contemplated that cancers caused by aberrations in apoptosis can also be treated by the methods and compositions of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

4.7.1 Other Anti-Cancer Therapies

The present invention provides methods of preventing, treating, managing or ameliorating cancer or one or more symptoms thereof, said methods comprising administering to a subject in need thereof one or more compounds identified in accordance with the methods of the invention and one or more therapies (e.g., prophylactic or therapeutic agents). Therapeutic or prophylactic agents include, but are not limited to, peptides, polypeptides, fusion proteins, nucleic acid molecules, small molecules, mimetic agents, synthetic drugs, inorganic molecules, and organic molecules. Any therapy (e.g., chemotherapies, radiation therapies, hormonal therapies, and/or biological therapies/immunotherapies) which is known to be useful, or which has been used or is currently being used for the prevention, treatment, management or amelioration of cancer or one or more symptoms thereof can be used in combination with a compound identified in accordance with the methods of the invention. Examples of such agents (i.e., anti-cancer agents) include, but are not limited to, angiogenesis inhibitors, topoisomerase inhibitors and immunomodulatory agents (such as chemotherapeutic agents). Angiogenesis inhibitors (i.e., anti-angiogenic agents) include, but are not limited to, angiostatin (plasminogen fragment); antiangiogenic antithrombin III; angiozyme; ABT-627; Bay 12-9566; Benefin; Bevacizumab; BMS-275291; cartilage-derived inhibitor (CDI); CAI; CD59 complement fragment; CEP-7055; Col 3; combretastatin A-4; endostatin (collagen XVIII fragment); fibronectin fragment; Gro-beta; Halofuginone; Heparinases; Heparin hexasaccharide fragment; HMV833; human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-methoxyestradiol; MMI 270 (CGS 27023A); MoAb IMC-1C11; Neovastat; NM-3; Panzem; PI-88; Placental ribonuclease inhibitor; plasminogen activator inhibitor; platelet factor-4 (PF4); Prinomastat; Prolactin 16 kD fragment; Proliferin-related protein (PRP); PTK 787/ZK 222594; retinoids; solimastat; squalamine; SS 3304; SU 5416; SU6668; SU11248; tetrahydrocortisol-S; tetrathiomolybdate; thalidomide; thrombospondin-1 (TSP-1); TNP-470; transforming growth factor-beta; vasculostatin; vasostatin (calreticulin fragment); ZD6126; ZD 6474; farnesyl transferase inhibitors (FTI); and bisphosphonates. In a specific embodiment, anti-angiogenic agents do not include antibodies or fragments thereof that immunospecifically bind to integrin $\alpha_v\beta_3$.

Specific examples of anti-cancer agents which can be used in accordance with the methods of the invention include, but not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel;

docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; and zinostatin stimalamer.

The invention also encompasses the administration of one or more compounds identified in accordance with the methods of the invention in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the Physician's Desk Reference (56$^{th}$ ed., 2002).

4.8 Compositions and Methods of Administering Compounds

Biologically active compounds identified using the methods of the invention or a pharmaceutically acceptable salt thereof can be administered to a patient, preferably a mammal, more preferably a human, suffering from a proliferative disorder. In a specific embodiment, a compound or a pharmaceutically acceptable salt thereof is administered to a patient, preferably a mammal, more preferably a human, as a preventative measure against a proliferative disorder.

When administered to a patient, the compound or a pharmaceutically acceptable salt thereof is preferably administered as component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the compound and pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of the compound or a pharmaceutically acceptable salt thereof into the bloodstream.

In specific embodiments, it may be desirable to administer the compound or a pharmaceutically acceptable salt thereof locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce the compound or a pharmaceutically acceptable salt thereof into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound and pharmaceutically acceptable salts thereof can be formulated as a suppository, with traditional binders and vehicles such as triglycerides.

In another embodiment, the compound and pharmaceutically acceptable salts thereof can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compound and pharmaceutically acceptable salts thereof can be delivered in a controlled release system (see, e.g., Goodson, in Medical Applications of Controlled Release, supra, vol. 2, pp. 115-138 (1984)). Other controlled-release systems discussed in the review by Langer, 1990, Science 249:1527-1533 may be used. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of a target RNA of the compound or a pharmaceutically acceptable salt thereof, thus requiring only a fraction of the systemic dose.

Compositions comprising the compound or a pharmaceutically acceptable salt thereof ("compound compositions") can additionally comprise a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Compound compositions, if desired, can also contain minor amounts of wetting or emulsifying agents, or pH buffering agents.

Compound compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Pharmaceutical Sciences, Alfonso R. Gennaro, ed., Mack Publishing Co. Easton, Pa., 19th ed., 1995, pp. 1447 to 1676, incorporated herein by reference.

In a preferred embodiment, the compound or a pharmaceutically acceptable salt thereof is formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, and the like. Such vehicles are preferably of pharmaceutical grade. Typically, compositions for intravenous administration comprise sterile isotonic aqueous buffer. Where necessary, the compositions may also include a solubilizing agent.

In another embodiment, the compound or a pharmaceutically acceptable salt thereof can be formulated for intravenous administration. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the compound or a pharmaceutically acceptable salt thereof is to be administered by infusion, it can be dispensed, for example, with an infusion bottle containing sterile pharmaceutical grade water or saline. Where the compound or a pharmaceutically acceptable salt thereof is administered by injection, an ampoule of sterile water for injection or saline can be provided so that the ingredients may be mixed prior to administration.

The amount of a compound or a pharmaceutically acceptable salt thereof that will be effective in the treatment of a particular disease will depend on the nature of the disease, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of the practitioner and each patient's circumstances. However, suitable dosage ranges for oral administration are generally about 0.001 milligram to about 500 milligrams of a compound or a pharmaceutically acceptable salt thereof per kilogram body weight per day. In specific preferred embodiments of the invention, the oral dose is about 0.01 milligram to about 100 milligrams per kilogram body weight per day, more preferably about 0.1 milligram to about 75 milligrams per kilogram body weight per day, more preferably about 0.5 milligram to 5 milligrams per kilogram body weight per day. The dosage amounts described herein refer to total amounts administered; that is, if more than one compound is administered, or if a compound is administered with a therapeutic agent, then the preferred dosages correspond to the total amount administered. Oral compositions preferably contain about 10% to about 95% active ingredient by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. Suitable dosage ranges for intranasal administration are generally about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight per day. Suitable doses for topical administration are in the range of about 0.001 milligram to about 1 milligram, depending on the area of administration. Effective doses may be extrapolated from dose-response curves derived from in vitro or animal model test systems. Such animal models and systems are well known in the art.

The compound and pharmaceutically acceptable salts thereof are preferably assayed in vitro and in vivo, for the desired therapeutic or prophylactic activity, prior to use in humans. For example, in vitro assays can be used to determine whether it is preferable to administer the compound, a pharmaceutically acceptable salt thereof, and/or another therapeutic agent. Animal model systems can be used to demonstrate safety and efficacy.

EQUIVALENTS

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

---

What is claimed is:

1. A method for identifying a compound that modulates the ability of animalia tRNA splicing endonuclease to produce mature tRNA, the method comprising:
   (a) contacting a compound or a compound from a library of compounds with an animalia cell that contains the animalia tRNA splicing endonuclease and expresses a full-length protein encoded by the coding region of a reporter gene of a nucleic acid substrate, wherein the nucleic acid substrate comprises the coding region of a reporter gene and a tRNA intron in a mature domain of a precursor tRNA, and wherein the tRNA intron is contained within the nucleic acid substrate such that the transcribed mRNA from the coding region of the reporter gene is out of frame; and
   (b) detecting the amount of full-length protein expressed, wherein an alteration in the amount of the full-length protein expressed in the presence of the compound or the compound from the library of compounds relative to the amount of the full-length protein expressed in the absence of the compound or the compound from a library of compounds, or in the presence of a negative control indicates that the compound or the compound from the library of compounds modulates the ability of animalia tRNA splicing endonuclease to produce mature tRNA.

2. The method of claim 1, wherein a decrease in the amount of the full-length protein expressed in the presence of the compound or the compound from the library of compounds relative to the amount of the full-length protein expressed in the absence of the compound or the compound from the library of compounds, or the presence of a negative control indicates that the compound or the compound from the library of compounds reduces the ability of animalia tRNA splicing endonuclease to produce mature tRNA.

3. The method of claim 1, wherein an increase in the amount of the full-length protein expressed in the presence of the compound or the compound from the library of compounds relative to the amount of the full-length protein expressed in the absence of the compound or the compound from the library of compounds, or the presence of a negative control indicates that the compound or the compound from the library of compounds increases the ability of animalia tRNA splicing endonuclease to produce mature tRNA.

4. The method of claim 1, 2 or 3, wherein the coding region of the reporter gene encodes at least one or more coding regions of the reporter genes from the group consisting of firefly luciferase, renilla luciferase, click beetle luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase, and alkaline phosphatase.

5. The method of claim 1, 2 or 3, wherein the animalia cell is a human cell.

6. The method of claim 4, wherein the animalia cell is a human cell.

7. The method of claim 1, 2 or 3, wherein the animalia tRNA splicing endonuclease is a human tRNA splicing endonuclease.

8. The method of claim 4, wherein the animalia tRNA splicing endonuclease is a human tRNA splicing endonuclease.

9. The method of claim 5, wherein the animalia tRNA splicing endonuclease is a human tRNA splicing endonuclease.

10. The method of claim 1, 2 or 3, wherein the tRNA intron is in the coding region of the reporter gene.

11. The method of claim 4, wherein the tRNA intron is in the coding region of the reporter gene.

12. The method of claim 5, wherein the tRNA intron is in the coding region of the reporter gene.

* * * * *

SEQUENCE LISTING

```
<160> NUMBER OF SEQ ID NOS: 4

<210> SEQ ID NO 1
<211> LENGTH: 465
<212> TYPE: PRT
<213> ORGANISM: Homo sapiens
<220> FEATURE:
<221> NAME/KEY: HsSen2p

<400> SEQUENCE: 1

Met Ala Glu Ala Val Phe His Ala Pro Lys Arg Lys Arg Arg Val Tyr
 1               5                  10                  15

Glu Thr Tyr Glu Ser Pro Leu Pro Ile Pro Phe Gly Gln Asp His Gly
                20                  25                  30

Pro Leu Lys Glu Phe Lys Ile Phe Arg Ala Glu Met Ile Asn Asn Asn
            35                  40                  45
```

```
Val Ile Val Arg Asn Ala Glu Asp Ile Glu Gln Leu Tyr Gly Lys Gly
 50                  55                  60

Tyr Phe Gly Lys Gly Ile Leu Ser Arg Ser Arg Pro Ser Phe Thr Ile
 65                  70                  75                  80

Ser Asp Pro Lys Leu Val Ala Lys Trp Lys Asp Met Lys Thr Asn Met
                 85                  90                  95

Pro Ile Ile Thr Ser Lys Arg Tyr Gln His Ser Val Glu Trp Ala Ala
             100                 105                 110

Glu Leu Met Arg Arg Gln Gly Gln Asp Glu Ser Thr Val Arg Arg Ile
         115                 120                 125

Leu Lys Asp Tyr Thr Lys Pro Leu Glu His Pro Val Lys Arg Asn
     130                 135                 140

Glu Glu Ala Gln Val His Asp Lys Leu Asn Ser Gly Met Val Ser Asn
145                 150                 155                 160

Met Glu Gly Thr Ala Gly Gly Glu Arg Pro Ser Val Val Asn Gly Asp
                 165                 170                 175

Ser Gly Lys Ser Gly Gly Val Gly Asp Pro Arg Glu Pro Leu Gly Cys
             180                 185                 190

Leu Gln Glu Gly Ser Gly Cys His Pro Thr Thr Glu Ser Phe Glu Lys
         195                 200                 205

Ser Val Arg Glu Asp Ala Ser Pro Leu Pro His Val Cys Cys Cys Lys
     210                 215                 220

Gln Asp Ala Leu Ile Leu Gln Arg Gly Leu His His Glu Asp Gly Ser
225                 230                 235                 240

Gln His Ile Gly Leu Leu His Pro Gly Asp Arg Gly Pro Asp His Glu
                 245                 250                 255

Tyr Val Leu Val Glu Glu Ala Glu Cys Ala Met Ser Glu Arg Glu Ala
             260                 265                 270

Ala Pro Asn Glu Glu Leu Val Gln Arg Asn Arg Leu Ile Cys Arg Arg
         275                 280                 285

Asn Pro Tyr Arg Ile Phe Glu Tyr Leu Gln Leu Ser Leu Glu Glu Ala
     290                 295                 300

Phe Phe Leu Val Tyr Ala Leu Gly Cys Leu Ser Ile Tyr Tyr Glu Lys
305                 310                 315                 320

Glu Pro Leu Thr Ile Val Lys Leu Trp Lys Ala Phe Thr Val Val Gln
                 325                 330                 335

Pro Thr Phe Arg Thr Thr Tyr Met Ala Tyr His Tyr Phe Arg Ser Lys
             340                 345                 350

Gly Trp Val Pro Lys Val Gly Leu Lys Tyr Gly Thr Asp Leu Leu Leu
         355                 360                 365

Tyr Arg Lys Gly Pro Pro Phe Tyr His Ala Ser Tyr Ser Val Ile Ile
     370                 375                 380

Glu Leu Val Asp Asp His Phe Glu Gly Ser Leu Arg Arg Pro Leu Ser
385                 390                 395                 400

Trp Lys Ser Leu Ala Ala Leu Ser Arg Val Ser Val Asn Val Ser Lys
                 405                 410                 415

Glu Leu Met Leu Cys Tyr Leu Ile Lys Pro Ser Thr Met Thr Asp Lys
             420                 425                 430

Glu Met Glu Ser Pro Glu Cys Met Lys Arg Ile Lys Val Gln Glu Val
         435                 440                 445

Ile Leu Ser Arg Trp Val Ser Ser Arg Glu Arg Ser Asp Gln Asp Asp
     450                 455                 460

Leu
465
```

```
<210> SEQ ID NO 2
<211> LENGTH: 448
<212> TYPE: PRT
<213> ORGANISM: Homo sapiens
<220> FEATURE:
<221> NAME/KEY: HsSen2 variant

<400> SEQUENCE: 2
```

Met Ala Glu Ala Val Phe His Ala Pro Lys Arg Lys Arg Arg Val Tyr
 1               5                  10                  15

Glu Thr Tyr Glu Ser Pro Leu Pro Ile Pro Phe Gly Gln Asp His Gly
            20                  25                  30

Pro Leu Lys Glu Phe Lys Ile Phe Arg Ala Glu Met Ile Asn Asn Asn
        35                  40                  45

Val Ile Val Arg Asn Ala Glu Asp Ile Glu Gln Leu Tyr Gly Lys Gly
    50                  55                  60

Tyr Phe Gly Lys Gly Ile Leu Ser Arg Ser Arg Pro Ser Phe Thr Ile
65                  70                  75                  80

Ser Asp Pro Lys Leu Val Ala Lys Trp Lys Asp Met Lys Thr Asn Met
                85                  90                  95

Pro Ile Ile Thr Ser Lys Arg Tyr Gln His Ser Val Glu Trp Ala Ala
            100                 105                 110

Glu Leu Met Arg Arg Gln Gly Gln Asp Glu Ser Thr Val Arg Arg Ile
        115                 120                 125

Leu Lys Asp Tyr Thr Lys Pro Leu Glu His Pro Pro Val Lys Arg Asn
    130                 135                 140

Glu Glu Ala Gln Val His Asp Lys Leu Asn Ser Gly Met Val Ser Asn
145                 150                 155                 160

Met Glu Gly Thr Ala Gly Gly Glu Arg Pro Ser Val Val Asn Gly Asp
                165                 170                 175

Ser Gly Lys Ser Gly Val Gly Asp Pro Arg Glu Pro Leu Gly Cys
            180                 185                 190

Leu Gln Glu Gly Ser Gly Cys His Pro Thr Thr Glu Ser Phe Glu Lys
        195                 200                 205

Ser Val Arg Glu Asp Ala Ser Pro Leu Pro His Val Cys Cys Cys Lys
    210                 215                 220

Gln Asp Ala Leu Ile Leu Gln Arg Gly Leu His Glu Asp Gly Ser
225                 230                 235                 240

Gln His Ile Gly Leu Leu His Pro Gly Asp Arg Gly Pro Asp His Glu
                245                 250                 255

Tyr Val Leu Val Glu Glu Ala Glu Cys Ala Met Ser Glu Arg Glu Ala
            260                 265                 270

Ala Pro Asn Glu Glu Leu Val Gln Arg Asn Arg Leu Ile Cys Arg Arg
        275                 280                 285

Asn Pro Tyr Arg Ile Phe Glu Tyr Leu Gln Leu Ser Leu Glu Glu Glu
    290                 295                 300

Pro Leu Thr Ile Val Lys Leu Trp Lys Ala Phe Thr Val Val Gln Pro
305                 310                 315                 320

Thr Phe Arg Thr Thr Tyr Met Ala Tyr His Tyr Phe Arg Ser Lys Gly
                325                 330                 335

Trp Val Pro Lys Val Gly Leu Lys Tyr Gly Thr Asp Leu Leu Leu Tyr
            340                 345                 350

Arg Lys Gly Pro Pro Phe Tyr His Ala Ser Tyr Ser Val Ile Ile Glu
        355                 360                 365

```
Leu Val Asp Asp His Phe Glu Gly Ser Leu Arg Arg Pro Leu Ser Trp
        370                 375                 380

Lys Ser Leu Ala Ala Leu Ser Arg Val Ser Val Asn Val Ser Lys Glu
385                 390                 395                 400

Leu Met Leu Cys Tyr Leu Ile Lys Pro Ser Thr Met Thr Asp Lys Glu
                405                 410                 415

Met Glu Ser Pro Glu Cys Met Lys Arg Ile Lys Val Gln Glu Val Ile
            420                 425                 430

Leu Ser Arg Trp Val Ser Ser Arg Glu Arg Ser Asp Gln Asp Asp Leu
435                 440                 445

<210> SEQ ID NO 3
<211> LENGTH: 377
<212> TYPE: PRT
<213> ORGANISM: Saccharomyces cerevisiae
<220> FEATURE:
<221> NAME/KEY: Sc Sen2p

<400> SEQUENCE: 3

Met Ser Lys Gly Arg Val Asn Gln Lys Arg Tyr Lys Tyr Pro Leu Pro
1               5                   10                  15

Ile His Pro Val Asp Asp Leu Pro Glu Leu Ile Leu Asn Pro Leu
            20                  25                  30

Ser Trp Leu Tyr Trp Ala Tyr Arg Tyr Tyr Lys Ser Thr Asn Ala Leu
        35                  40                  45

Asn Asp Lys Val His Val Asp Phe Ile Gly Asp Thr Thr Leu His Ile
    50                  55                  60

Thr Val Gln Asp Asp Lys Gln Met Leu Tyr Leu Trp Asn Asn Gly Phe
65              70                  75                  80

Phe Gly Thr Gly Gln Phe Ser Arg Ser Glu Pro Thr Trp Lys Ala Arg
                85                  90                  95

Thr Glu Ala Arg Leu Gly Leu Asn Asp Thr Pro Leu His Asn Arg Gly
            100                 105                 110

Gly Thr Lys Ser Asn Thr Glu Thr Glu Met Thr Leu Glu Lys Val Thr
        115                 120                 125

Gln Gln Arg Arg Leu Gln Arg Leu Glu Phe Lys Lys Glu Arg Ala Lys
    130                 135                 140

Leu Glu Arg Glu Leu Leu Glu Leu Arg Lys Lys Gly Gly His Ile Asp
145                 150                 155                 160

Glu Glu Asn Ile Leu Leu Glu Lys Gln Arg Glu Ser Leu Arg Lys Phe
                165                 170                 175

Lys Leu Lys Gln Thr Glu Asp Val Gly Ile Val Ala Gln Gln Gln Asp
            180                 185                 190

Ile Ser Glu Ser Asn Leu Arg Asp Glu Asp Asn Asn Leu Leu Asp Glu
        195                 200                 205

Asn Gly Asp Leu Leu Pro Leu Glu Ser Leu Glu Leu Met Pro Val Glu
    210                 215                 220

Ala Met Phe Leu Thr Phe Ala Leu Pro Val Leu Asp Ile Ser Pro Ala
225                 230                 235                 240

Cys Leu Ala Gly Lys Leu Phe Gln Phe Asp Ala Lys Tyr Lys Asp Ile
                245                 250                 255

His Ser Phe Val Arg Ser Tyr Val Ile Tyr His His Tyr Arg Ser His
            260                 265                 270

Gly Trp Cys Val Arg Ser Gly Ile Lys Phe Gly Cys Asp Tyr Leu Leu
        275                 280                 285

Tyr Lys Arg Gly Pro Pro Phe Gln His Ala Glu Phe Cys Val Met Gly
```

```
                    290                 295                 300
Leu Asp His Asp Val Ser Lys Asp Tyr Thr Trp Tyr Ser Ser Ile Ala
305                 310                 315                 320

Arg Val Val Gly Gly Ala Lys Lys Thr Phe Val Leu Cys Tyr Val Glu
                325                 330                 335

Arg Leu Ile Ser Glu Gln Glu Ala Ile Ala Leu Trp Lys Ser Asn Asn
                340                 345                 350

Phe Thr Lys Leu Phe Asn Ser Phe Gln Val Gly Glu Val Leu Tyr Lys
            355                 360                 365

Arg Trp Val Pro Gly Arg Asn Arg Asp
    370                 375

<210> SEQ ID NO 4
<211> LENGTH: 5
<212> TYPE: PRT
<213> ORGANISM: Artificial Sequence
<220> FEATURE:
<223> OTHER INFORMATION: Motif of the active site for the 5 prime
      splice site of yeast and archael tRNA splicing endounclease

<400> SEQUENCE: 4

Tyr Arg Gly Gly Tyr
1               5
```